(12) United States Patent
Deem et al.

(10) Patent No.: US 10,463,429 B2
(45) Date of Patent: Nov. 5, 2019

(54) METHODS, DEVICES, AND SYSTEMS FOR NON-INVASIVE DELIVERY OF MICROWAVE THERAPY

(71) Applicant: MIRADRY, INC., Santa Clara, CA (US)

(72) Inventors: Mark E. Deem, Mountain View, CA (US); Daniel E. Francis, Mountain View, CA (US); Jessi Ernest Johnson, Sunnyvale, CA (US); Steven W. Kim, Los Altos, CA (US); Alexey Salamini, San Francisco, CA (US)

(73) Assignee: MIRADRY, INC., Santa Clara, CA (US)

( * ) Notice: Subject to any disclaimer, the term of this patent is extended or adjusted under 35 U.S.C. 154(b) by 91 days.

(21) Appl. No.: 15/288,949

(22) Filed: Oct. 7, 2016

(65) Prior Publication Data
US 2017/0245929 A1 Aug. 31, 2017

Related U.S. Application Data

(63) Continuation of application No. 12/450,860, filed as application No. PCT/US2008/060929 on Apr. 18, 2008, now abandoned.
(Continued)

(51) Int. Cl.
*A61B 18/18* (2006.01)
*A61N 5/02* (2006.01)
(Continued)

(52) U.S. Cl.
CPC .......... *A61B 18/1815* (2013.01); *A61B 18/18* (2013.01); *A61B 34/10* (2016.02);
(Continued)

(58) Field of Classification Search
CPC ................ A61B 18/18; A61B 18/1815; A61B 2018/00005; A61B 2018/00017;
(Continued)

(56) References Cited

U.S. PATENT DOCUMENTS

| 2,407,690 A | 9/1946 | Southworth |
| 3,307,553 A | 3/1967 | Liebner |

(Continued)

FOREIGN PATENT DOCUMENTS

| AU | 297299 A | 9/1999 |
| CN | 1688363 A | 10/2005 |

(Continued)

OTHER PUBLICATIONS

Abraham et al.; Monopolar radiofrequency skin tightening; Facial Plast Surg Clin N Am; 15(2); pp. 169-177; May 2007.
(Continued)

*Primary Examiner* — Michael F Peffley
(74) *Attorney, Agent, or Firm* — Shay Glenn LLP

(57) ABSTRACT

Methods, apparatuses and systems are provided for non-invasive delivery of microwave therapy. Microwave energy may be applied to epidermal, dermal and subdermal tissue of a patient to achieve various therapeutic and/or aesthetic results. In one embodiment, the microwave energy is applied to a target tissue via an energy delivery applicator connected to an energy generator. The energy delivery applicator may comprise one or more antennas, including monopole, dipole, slot and/or waveguide antennas (among others) that are used to direct the microwave energy to the target tissue. The energy delivery applicator may also comprise a cooling element for avoiding thermal destruction to non-target tissue and/or a suction device to localize thermal treatment at specific portions of a skin fold.

8 Claims, 36 Drawing Sheets

Related U.S. Application Data

(60) Provisional application No. 60/912,899, filed on Apr. 19, 2007, provisional application No. 61/013,274, filed on Dec. 12, 2007, provisional application No. 61/045,937, filed on Apr. 17, 2008.

(51) Int. Cl.
*A61B 34/10* (2016.01)
*A61B 18/00* (2006.01)
*A61B 90/00* (2016.01)
*A61N 5/00* (2006.01)

(52) U.S. Cl.
CPC .............. *A61N 5/02* (2013.01); *A61N 5/025* (2013.01); *A61B 90/37* (2016.02); *A61B 2018/00005* (2013.01); *A61B 2018/00017* (2013.01); *A61B 2018/00023* (2013.01); *A61B 2018/00029* (2013.01); *A61B 2018/00041* (2013.01); *A61B 2018/00452* (2013.01); *A61B 2034/104* (2016.02); *A61N 2005/007* (2013.01)

(58) Field of Classification Search
CPC ........... A61B 2018/00023; A61B 2018/00029; A61B 2018/00041; A61B 2018/00452
See application file for complete search history.

(56) References Cited

U.S. PATENT DOCUMENTS

| | | |
|---|---|---|
| 3,527,227 A | 9/1970 | Fritz |
| 3,693,623 A | 9/1972 | Harte et al. |
| 3,845,267 A | 10/1974 | Fitzmayer |
| 4,069,827 A | 1/1978 | Dominy |
| 4,095,602 A | 6/1978 | Leveen |
| 4,108,147 A * | 8/1978 | Kantor ............. A61N 5/02 219/695 |
| 4,140,130 A | 2/1979 | Storm, III |
| 4,174,713 A | 11/1979 | Mehl |
| 4,190,053 A | 2/1980 | Sterzer |
| 4,190,056 A | 2/1980 | Tapper et al. |
| 4,197,860 A | 4/1980 | Sterzer |
| 4,228,809 A | 10/1980 | Paglione |
| 4,292,960 A | 10/1981 | Paglione |
| 4,332,260 A | 6/1982 | Bicher et al. |
| 4,375,220 A | 3/1983 | Matvias |
| 4,378,806 A | 4/1983 | Henley Cohn |
| 4,388,924 A | 6/1983 | Weissman et al. |
| 4,397,313 A * | 8/1983 | Vaguine ............ A61N 5/02 607/104 |
| 4,397,314 A | 8/1983 | Vaguine |
| 4,446,874 A | 5/1984 | Vaguine |
| 4,528,991 A | 7/1985 | Dittmar et al. |
| 4,589,424 A | 5/1986 | Vaguine |
| 4,597,379 A | 7/1986 | Kihn et al. |
| 4,614,191 A | 9/1986 | Perler |
| 4,617,926 A | 10/1986 | Sutton |
| 4,632,128 A | 12/1986 | Paglione et al. |
| 4,641,649 A | 2/1987 | Walinsky et al. |
| 4,669,475 A | 6/1987 | Turner |
| 4,672,980 A | 6/1987 | Turner |
| 4,690,156 A | 9/1987 | Kikuchi et al. |
| 4,702,262 A | 10/1987 | Andersen et al. |
| 4,744,372 A | 5/1988 | Kikuchi et al. |
| 4,747,416 A | 5/1988 | Kikuchi et al. |
| 4,794,930 A | 1/1989 | Machida et al. |
| 4,798,215 A | 1/1989 | Turner |
| 4,800,899 A | 1/1989 | Elliott |
| 4,825,880 A | 5/1989 | Stauffer et al. |
| 4,841,989 A | 6/1989 | Kikuchi et al. |
| 4,841,990 A | 6/1989 | Kikuchi et al. |
| 4,860,752 A | 8/1989 | Turner |
| 4,881,543 A | 11/1989 | Trembly et al. |
| 4,891,483 A | 1/1990 | Kikuchi et al. |
| 4,945,912 A | 8/1990 | Langberg |
| 4,974,587 A | 12/1990 | Turner et al. |
| 5,059,192 A | 10/1991 | Zaias |
| 5,097,846 A | 3/1992 | Larsen |
| 5,101,836 A | 4/1992 | Lee |
| 5,107,832 A | 4/1992 | Guibert et al. |
| 5,143,063 A | 9/1992 | Fellner |
| 5,186,181 A | 2/1993 | Franconi et al. |
| 5,190,518 A | 3/1993 | Takasu |
| 5,198,776 A | 3/1993 | Carr |
| 5,226,907 A | 7/1993 | Tankovich |
| 5,234,004 A | 8/1993 | Hascoet et al. |
| 5,246,438 A | 9/1993 | Langberg |
| 5,272,301 A | 12/1993 | Finger et al. |
| 5,295,955 A | 3/1994 | Rosen et al. |
| 5,301,692 A | 4/1994 | Knowlton |
| 5,305,748 A | 4/1994 | Wilk |
| 5,315,994 A | 5/1994 | Guibert et al. |
| 5,316,000 A | 5/1994 | Chapelon et al. |
| 5,364,336 A | 11/1994 | Carr |
| 5,364,394 A | 11/1994 | Mehl |
| 5,383,917 A | 1/1995 | Desai et al. |
| 5,385,544 A | 1/1995 | Edwards et al. |
| 5,405,346 A | 4/1995 | Grundy et al. |
| 5,407,440 A | 4/1995 | Zinreich et al. |
| 5,409,484 A | 4/1995 | Erlich et al. |
| 5,421,819 A | 6/1995 | Edwards et al. |
| 5,425,728 A | 6/1995 | Tankovich |
| 5,431,650 A | 7/1995 | Cosmescu |
| 5,433,740 A | 7/1995 | Yamaguchi |
| 5,441,532 A | 8/1995 | Fenn |
| 5,443,487 A | 8/1995 | Guibert et al. |
| 5,462,521 A | 10/1995 | Brucker et al. |
| 5,474,071 A | 12/1995 | Chapelon et al. |
| 5,503,150 A | 4/1996 | Evans |
| 5,507,741 A | 4/1996 | L'Esperance, Jr. |
| 5,507,790 A | 4/1996 | Weiss |
| 5,509,929 A | 4/1996 | Hascoet et al. |
| 5,522,814 A | 6/1996 | Bernaz |
| 5,531,662 A | 7/1996 | Carr |
| 5,540,681 A | 7/1996 | Strul et al. |
| 5,549,639 A | 8/1996 | Ross |
| 5,553,612 A | 9/1996 | Lundback |
| 5,569,237 A | 10/1996 | Beckenstein |
| 5,571,154 A | 11/1996 | Ren |
| 5,575,789 A | 11/1996 | Bell et al. |
| 5,584,830 A | 12/1996 | Ladd et al. |
| 5,586,981 A | 12/1996 | Hu |
| 5,595,568 A | 1/1997 | Anderson et al. |
| 5,649,973 A | 7/1997 | Tierney et al. |
| 5,660,836 A | 8/1997 | Knowlton |
| 5,662,110 A | 9/1997 | Carr |
| 5,669,916 A | 9/1997 | Anderson |
| 5,674,219 A | 10/1997 | Monson et al. |
| 5,683,381 A | 11/1997 | Carr et al. |
| 5,683,382 A | 11/1997 | Lenihan et al. |
| 5,690,614 A | 11/1997 | Carr et al. |
| 5,707,403 A | 1/1998 | Grove et al. |
| 5,724,966 A | 3/1998 | Lundback |
| 5,733,269 A | 3/1998 | Fuisz |
| 5,735,844 A | 4/1998 | Anderson et al. |
| 5,742,392 A | 4/1998 | Anderson et al. |
| 5,743,899 A | 4/1998 | Zinreich |
| 5,755,753 A | 5/1998 | Knowlton |
| 5,769,879 A | 6/1998 | Richards et al. |
| 5,776,127 A | 7/1998 | Anderson et al. |
| 5,782,897 A | 7/1998 | Carr |
| 5,810,801 A | 9/1998 | Anderson et al. |
| 5,810,804 A | 9/1998 | Gough et al. |
| 5,814,996 A | 9/1998 | Winter |
| 5,824,023 A | 10/1998 | Anderson |
| 5,830,208 A | 11/1998 | Muller |
| 5,836,999 A | 11/1998 | Eckhouse et al. |
| 5,868,732 A | 2/1999 | Waldman et al. |
| 5,879,346 A | 3/1999 | Waldman et al. |
| 5,891,094 A | 4/1999 | Masterson et al. |
| 5,897,549 A | 4/1999 | Tankovich |
| 5,902,263 A | 5/1999 | Patterson et al. |
| 5,904,709 A | 5/1999 | Arndt et al. |
| 5,919,218 A | 7/1999 | Carr |

(56) References Cited

U.S. PATENT DOCUMENTS

| | | | |
|---|---|---|---|
| 5,928,797 A | 7/1999 | Vineberg |
| 5,931,860 A | 8/1999 | Reid et al. |
| 5,949,845 A | 9/1999 | Sterzer |
| 5,971,982 A | 10/1999 | Betsill et al. |
| 5,979,454 A | 11/1999 | Anvari et al. |
| 5,983,124 A | 11/1999 | Carr |
| 5,983,900 A | 11/1999 | Clement et al. |
| 5,989,245 A | 11/1999 | Pescott |
| 6,015,404 A | 1/2000 | Altshuler et al. |
| 6,024,095 A | 2/2000 | Stanley, III |
| 6,026,331 A | 2/2000 | Feldberg et al. |
| 6,026,816 A | 2/2000 | McMillan et al. |
| 6,030,378 A | 2/2000 | Stewart |
| 6,036,632 A | 3/2000 | Whitmore, III et al. |
| 6,047,215 A | 4/2000 | McClure et al. |
| 6,050,990 A | 4/2000 | Tankovich et al. |
| 6,077,294 A | 6/2000 | Cho et al. |
| 6,080,146 A | 6/2000 | Altshuler et al. |
| 6,093,186 A | 7/2000 | Goble |
| 6,097,985 A | 8/2000 | Kasevich et al. |
| 6,104,959 A | 8/2000 | Spertell |
| 6,106,514 A | 8/2000 | O'Donnell, Jr. |
| 6,113,559 A | 9/2000 | Klopotek |
| 6,113,593 A | 9/2000 | Tu et al. |
| 6,126,636 A | 10/2000 | Naka |
| 6,129,696 A | 10/2000 | Sibalis |
| 6,139,569 A | 10/2000 | Ingle et al. |
| 6,149,644 A | 11/2000 | Xie |
| 6,162,212 A | 12/2000 | Kreindel et al. |
| 6,162,218 A | 12/2000 | Elbrecht et al. |
| 6,171,301 B1 | 1/2001 | Nelson et al. |
| 6,175,768 B1 | 1/2001 | Arndt et al. |
| 6,181,970 B1 | 1/2001 | Kasevich |
| 6,183,773 B1 | 2/2001 | Anderson |
| 6,187,001 B1 | 2/2001 | Azar et al. |
| 6,197,020 B1 | 3/2001 | O'Donnell, Jr. |
| 6,208,903 B1 | 3/2001 | Richards et al. |
| 6,210,367 B1 | 4/2001 | Carr |
| 6,214,034 B1 | 4/2001 | Azar |
| 6,223,076 B1 | 4/2001 | Tapper |
| 6,231,569 B1 | 5/2001 | Bek et al. |
| 6,235,016 B1 | 5/2001 | Stewart |
| 6,241,753 B1 | 6/2001 | Knowlton |
| 6,245,062 B1 | 6/2001 | Berube et al. |
| 6,264,652 B1 | 7/2001 | Eggers et al. |
| 6,273,884 B1 | 8/2001 | Altshuler et al. |
| 6,277,104 B1 | 8/2001 | Lasko et al. |
| 6,277,111 B1 | 8/2001 | Clement et al. |
| 6,277,116 B1 | 8/2001 | Utely et al. |
| 6,280,441 B1 | 8/2001 | Ryan |
| 6,283,956 B1 | 9/2001 | McDaniel |
| 6,283,987 B1 | 9/2001 | Laird et al. |
| 6,287,302 B1 | 9/2001 | Berube |
| 6,290,699 B1 | 9/2001 | Hall et al. |
| 6,293,941 B1 | 9/2001 | Strul et al. |
| 6,306,128 B1 | 10/2001 | Waldman et al. |
| 6,306,130 B1 | 10/2001 | Anderson et al. |
| 6,319,211 B1 | 11/2001 | Ito et al. |
| 6,322,584 B2 | 11/2001 | Ingle et al. |
| 6,325,769 B1 | 12/2001 | Klopotek |
| 6,325,796 B1 * | 12/2001 | Berube ................ A61B 18/18 606/33 |
| 6,330,479 B1 | 12/2001 | Stauffer |
| 6,334,074 B1 | 12/2001 | Spertell |
| 6,347,251 B1 | 2/2002 | Deng |
| 6,350,263 B1 | 2/2002 | Wetzig et al. |
| 6,350,276 B1 | 2/2002 | Knowlton |
| 6,361,531 B1 | 3/2002 | Hissong |
| 6,364,876 B1 | 4/2002 | Erb et al. |
| 6,383,176 B1 | 5/2002 | Connors et al. |
| 6,387,103 B2 | 5/2002 | Shadduck |
| 6,402,739 B1 | 6/2002 | Neev |
| 6,409,720 B1 | 6/2002 | Hissong et al. |
| 6,409,722 B1 | 6/2002 | Hoey et al. |
| 6,413,253 B1 | 7/2002 | Koop et al. |
| 6,413,254 B1 | 7/2002 | Hissong et al. |
| 6,413,255 B1 | 7/2002 | Stern |
| 6,427,089 B1 | 7/2002 | Knowlton |
| 6,428,532 B1 | 8/2002 | Doukas et al. |
| 6,430,446 B1 | 8/2002 | Knowlton |
| 6,436,094 B1 | 8/2002 | Reuter |
| 6,436,127 B1 | 8/2002 | Anderson et al. |
| 6,443,914 B1 | 9/2002 | Costantino |
| 6,443,946 B2 | 9/2002 | Clement et al. |
| 6,451,013 B1 | 9/2002 | Bays et al. |
| 6,451,015 B1 | 9/2002 | Rittman, III et al. |
| 6,457,476 B1 | 10/2002 | Elmer et al. |
| 6,461,378 B1 | 10/2002 | Knowlton |
| 6,468,235 B2 | 10/2002 | Ito et al. |
| 6,470,216 B1 | 10/2002 | Knowlton |
| 6,471,662 B1 | 10/2002 | Jaggy et al. |
| 6,471,696 B1 | 10/2002 | Berube et al. |
| 6,475,179 B1 | 11/2002 | Wang et al. |
| 6,475,211 B2 | 11/2002 | Chess et al. |
| 6,480,746 B1 | 11/2002 | Ingle et al. |
| 6,485,484 B1 | 11/2002 | Connors et al. |
| 6,485,703 B1 | 11/2002 | Coté et al. |
| 6,500,141 B1 | 12/2002 | Irion et al. |
| 6,508,813 B1 | 1/2003 | Altshuler |
| 6,514,250 B1 | 2/2003 | Jahns et al. |
| 6,517,532 B1 | 2/2003 | Altshuler et al. |
| 6,527,768 B2 * | 3/2003 | Berube ................ A61B 18/18 606/33 |
| 6,529,778 B2 | 3/2003 | Prutchi |
| 6,558,382 B2 | 5/2003 | Jahns et al. |
| 6,575,969 B1 | 6/2003 | Rittman, III et al. |
| 6,577,903 B1 | 6/2003 | Cronin et al. |
| 6,584,360 B2 | 6/2003 | Francischelli et al. |
| 6,585,733 B2 | 7/2003 | Wellman |
| 6,595,934 B1 | 7/2003 | Hissong et al. |
| 6,600,951 B1 | 7/2003 | Anderson |
| 6,605,080 B1 | 8/2003 | Altshuler et al. |
| 6,607,498 B2 | 8/2003 | Eshel |
| 6,626,854 B2 | 9/2003 | Friedman et al. |
| 6,628,990 B1 | 9/2003 | Habib et al. |
| 6,629,974 B2 | 10/2003 | Penny et al. |
| 6,645,162 B2 | 11/2003 | Friedman et al. |
| 6,648,904 B2 | 11/2003 | Altshuler et al. |
| 6,652,518 B2 | 11/2003 | Wellman et al. |
| 6,653,618 B2 | 11/2003 | Zenzie |
| 6,662,054 B2 | 12/2003 | Kreindel et al. |
| 6,663,659 B2 | 12/2003 | McDaniel |
| 6,676,654 B1 | 1/2004 | Balle Petersen et al. |
| 6,676,655 B2 | 1/2004 | McDaniel |
| 6,682,501 B1 | 1/2004 | Nelson et al. |
| 6,692,450 B1 | 2/2004 | Coleman |
| 6,723,090 B2 | 4/2004 | Altshuler et al. |
| 6,725,095 B2 | 4/2004 | Fenn et al. |
| 6,736,810 B2 | 5/2004 | Hoey et al. |
| 6,743,222 B2 | 6/2004 | Durkin et al. |
| 6,763,836 B2 | 7/2004 | Tasto et al. |
| 6,766,202 B2 | 7/2004 | Underwood et al. |
| 6,807,446 B2 | 10/2004 | Fenn et al. |
| 6,808,532 B2 | 10/2004 | Andersen et al. |
| 6,821,274 B2 | 11/2004 | McHale et al. |
| 6,823,216 B1 | 11/2004 | Salomir et al. |
| 6,824,542 B2 | 11/2004 | Jay |
| 6,856,839 B2 | 2/2005 | Litovitz |
| 6,861,954 B2 | 3/2005 | Levin |
| 6,878,144 B2 | 4/2005 | Altshuler et al. |
| 6,878,147 B2 | 4/2005 | Prakash et al. |
| 6,881,212 B2 | 4/2005 | Clement et al. |
| 6,887,239 B2 | 5/2005 | Elstrom et al. |
| 6,887,260 B1 | 5/2005 | McDaniel |
| 6,888,319 B2 | 5/2005 | Inochkin et al. |
| 6,897,238 B2 | 5/2005 | Anderson |
| 6,907,879 B2 | 6/2005 | Drinan et al. |
| 6,916,316 B2 | 7/2005 | Jay |
| 6,918,908 B2 | 7/2005 | Bonner et al. |
| 6,939,344 B2 | 9/2005 | Kreindel |
| 6,939,346 B2 | 9/2005 | Kannenberg et al. |
| 6,955,672 B2 | 10/2005 | Cense et al. |
| 6,974,415 B2 | 12/2005 | Cerwin et al. |
| 6,976,984 B2 | 12/2005 | Cense et al. |

(56) References Cited

U.S. PATENT DOCUMENTS

| | | |
|---|---|---|
| 6,997,923 B2 | 2/2006 | Anderson et al. |
| 7,006,874 B2 | 2/2006 | Knowlton et al. |
| 7,022,121 B2 | 4/2006 | Stern et al. |
| 7,029,469 B2 | 4/2006 | Vasily |
| 7,033,352 B1 | 4/2006 | Gauthier et al. |
| 7,044,959 B2 | 5/2006 | Anderson et al. |
| 7,056,318 B2 | 6/2006 | Black |
| 7,066,929 B1 | 6/2006 | Azar et al. |
| 7,074,218 B2 | 7/2006 | Washington et al. |
| 7,081,111 B2 | 7/2006 | Svaasand et al. |
| 7,089,054 B2 | 8/2006 | Palti |
| 7,107,997 B1 | 9/2006 | Moses et al. |
| 7,115,123 B2 | 10/2006 | Knowlton et al. |
| 7,118,590 B1 | 10/2006 | Cronin |
| 7,122,029 B2 | 10/2006 | Koop et al. |
| 7,128,739 B2 | 10/2006 | Prakash et al. |
| 7,135,033 B2 | 11/2006 | Altshuler et al. |
| 7,136,699 B2 | 11/2006 | Palti |
| 7,141,049 B2 | 11/2006 | Stern et al. |
| 7,151,964 B2 | 12/2006 | Desai et al. |
| 7,153,256 B2 | 12/2006 | Riehl et al. |
| 7,153,285 B2 | 12/2006 | Lauman et al. |
| 7,162,291 B1 | 1/2007 | Nachaliel |
| 7,163,536 B2 | 1/2007 | Godara |
| 7,175,950 B2 | 2/2007 | Anderson et al. |
| 7,189,230 B2 | 3/2007 | Knowlton |
| 7,192,429 B2 | 3/2007 | Trembly |
| 7,204,832 B2 | 4/2007 | Altshuler et al. |
| 7,217,265 B2 | 5/2007 | Hennings et al. |
| 7,220,254 B2 | 5/2007 | Altshuler et al. |
| 7,220,778 B2 | 5/2007 | Anderson et al. |
| 7,229,436 B2 | 6/2007 | Stern et al. |
| 7,234,739 B2 | 6/2007 | Saitoh et al. |
| 7,238,182 B2 | 7/2007 | Swoyer et al. |
| 7,241,291 B2 | 7/2007 | Kreindel et al. |
| 7,247,155 B2 | 7/2007 | Hoey et al. |
| 7,250,047 B2 | 7/2007 | Anderson et al. |
| 7,252,628 B2 | 8/2007 | Van Hal et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,290,326 B2 | 11/2007 | Dutton |
| 7,309,335 B2 | 12/2007 | Altshuler et al. |
| 7,311,674 B2 | 12/2007 | Gingrich et al. |
| 7,329,273 B2 | 2/2008 | Altshuler et al. |
| 7,329,274 B2 | 2/2008 | Altshuler et al. |
| 7,331,951 B2 | 2/2008 | Eshel et al. |
| 7,344,587 B2 | 3/2008 | Khan et al. |
| 7,347,855 B2 | 3/2008 | Eshel et al. |
| 7,351,252 B2 | 4/2008 | Altshuler et al. |
| 7,354,448 B2 | 4/2008 | Altshuler et al. |
| 7,367,341 B2 | 5/2008 | Anderson et al. |
| 7,377,917 B2 | 5/2008 | Trembly |
| 7,399,297 B2 | 7/2008 | Ikadai et al. |
| 7,422,586 B2 | 9/2008 | Morris et al. |
| 7,422,598 B2 | 9/2008 | Altshuler et al. |
| 7,431,718 B2 | 10/2008 | Ikadai |
| 7,470,270 B2 | 12/2008 | Azar et al. |
| 7,479,101 B2 | 1/2009 | Hunter et al. |
| 7,481,807 B2 | 1/2009 | Knudsen et al. |
| 7,491,171 B2 | 2/2009 | Barthe et al. |
| 7,524,328 B2 | 4/2009 | Connors et al. |
| 7,530,356 B2 | 5/2009 | Slayton et al. |
| 7,530,958 B2 | 5/2009 | Slayton et al. |
| 7,540,869 B2 | 6/2009 | Altshuler et al. |
| 7,544,204 B2 | 6/2009 | Krespi et al. |
| 7,565,207 B2 | 7/2009 | Turner et al. |
| 7,568,619 B2 | 8/2009 | Todd et al. |
| 7,588,547 B2 | 9/2009 | Deem et al. |
| 7,599,745 B2 | 10/2009 | Palti |
| 7,601,128 B2 | 10/2009 | Deem et al. |
| 7,613,523 B2 | 11/2009 | Eggers et al. |
| 7,630,774 B2 | 12/2009 | Karni et al. |
| 7,643,883 B2 | 1/2010 | Kreindel |
| 7,682,321 B2 | 3/2010 | Naldoni |
| 7,722,535 B2 | 5/2010 | Randlov et al. |
| 7,722,600 B2 | 5/2010 | Connors et al. |
| 7,722,656 B1 | 5/2010 | Segal |
| 7,736,360 B2 | 6/2010 | Mody et al. |
| 7,740,600 B2 | 6/2010 | Slatkine et al. |
| 7,740,651 B2 | 6/2010 | Barak et al. |
| 7,749,260 B2 | 7/2010 | Da Silva et al. |
| 7,758,524 B2 | 7/2010 | Barthe et al. |
| 7,758,537 B1 | 7/2010 | Brunell et al. |
| 7,762,964 B2 | 7/2010 | Slatkine |
| 7,763,060 B2 | 7/2010 | Baumann |
| 7,771,421 B2 | 8/2010 | Stewart et al. |
| 7,799,019 B2 | 9/2010 | Turovskiy et al. |
| 7,805,201 B2 | 9/2010 | Palti |
| 7,815,570 B2 | 10/2010 | Eshel et al. |
| 7,815,633 B2 | 10/2010 | Zanelli et al. |
| 7,824,394 B2 | 11/2010 | Manstein |
| 7,828,734 B2 | 11/2010 | Azhari et al. |
| 7,837,694 B2 | 11/2010 | Tethrake et al. |
| 7,842,029 B2 | 11/2010 | Anderson et al. |
| 7,854,754 B2 | 12/2010 | Ting et al. |
| 7,857,773 B2 | 12/2010 | Desilets et al. |
| 7,857,775 B2 | 12/2010 | Rosenberg et al. |
| 7,862,564 B2 | 1/2011 | Goble |
| 7,864,129 B2 | 1/2011 | Konishi |
| 7,891,362 B2 | 2/2011 | Domankevitz et al. |
| 7,905,844 B2 | 3/2011 | Desilets et al. |
| 8,073,550 B1 | 12/2011 | Spertell |
| 8,211,099 B2 | 7/2012 | Buysse et al. |
| 8,367,959 B2 | 2/2013 | Spertell |
| 8,401,668 B2 | 3/2013 | Deem et al. |
| 8,406,894 B2 | 3/2013 | Johnson et al. |
| 8,469,951 B2 | 6/2013 | Ben-Haim et al. |
| 8,535,302 B2 | 9/2013 | Ben-Haim et al. |
| 8,688,228 B2 | 4/2014 | Johnson et al. |
| 8,825,176 B2 | 9/2014 | Johnson et al. |
| 8,853,600 B2 | 10/2014 | Spertell |
| 9,028,477 B2 | 5/2015 | Ben-Haim et al. |
| 9,149,331 B2 | 10/2015 | Deem et al. |
| 9,216,058 B2 | 12/2015 | Spertell |
| 9,241,763 B2 | 1/2016 | Kim et al. |
| 9,314,301 B2 | 4/2016 | Ben-Haim et al. |
| 9,427,285 B2 | 8/2016 | Deem et al. |
| 2001/0005775 A1 | 6/2001 | Samson |
| 2001/0016761 A1 | 8/2001 | Rudie et al. |
| 2001/0050083 A1 | 12/2001 | Marchitto et al. |
| 2002/0062124 A1 | 5/2002 | Keane |
| 2002/0087151 A1 | 7/2002 | Mody et al. |
| 2002/0156471 A1 | 10/2002 | Stern et al. |
| 2002/0165529 A1 | 11/2002 | Danek |
| 2002/0193851 A1 | 12/2002 | Silverman et al. |
| 2003/0004082 A1 | 1/2003 | Masschelein et al. |
| 2003/0120269 A1 | 6/2003 | Bessette et al. |
| 2003/0130575 A1 | 7/2003 | Desai |
| 2003/0130711 A1 | 7/2003 | Pearson et al. |
| 2003/0158566 A1 | 8/2003 | Brett |
| 2003/0212393 A1 | 11/2003 | Knowlton et al. |
| 2003/0216728 A1 | 11/2003 | Stern et al. |
| 2003/0220639 A1 | 11/2003 | Chapelon et al. |
| 2004/0000316 A1 | 1/2004 | Knowlton et al. |
| 2004/0002705 A1 | 1/2004 | Knowlton et al. |
| 2004/0049251 A1 | 3/2004 | Knowlton |
| 2004/0073115 A1 | 4/2004 | Horzewski et al. |
| 2004/0092875 A1 | 5/2004 | Kochamba |
| 2004/0140028 A1 | 7/2004 | Clark et al. |
| 2004/0186535 A1 | 9/2004 | Knowlton |
| 2004/0206365 A1 | 10/2004 | Knowlton |
| 2004/0210214 A1* | 10/2004 | Knowlton ............... A61B 18/14 606/41 |
| 2004/0230260 A1 | 11/2004 | Macfarland et al. |
| 2004/0243182 A1 | 12/2004 | Cohen et al. |
| 2004/0243200 A1 | 12/2004 | Turner et al. |
| 2004/0249426 A1 | 12/2004 | Hoenig et al. |
| 2005/0010271 A1 | 1/2005 | Merchant |
| 2005/0137654 A1 | 6/2005 | Hoenig et al. |
| 2005/0215901 A1 | 9/2005 | Anderson et al. |
| 2005/0215987 A1 | 9/2005 | Slatkine |
| 2005/0251117 A1 | 11/2005 | Anderson et al. |
| 2005/0251120 A1 | 11/2005 | Anderson et al. |

(56) References Cited

U.S. PATENT DOCUMENTS

| | | |
|---|---|---|
| 2005/0288666 A1 | 12/2005 | Bertolero et al. |
| 2006/0020309 A1 | 1/2006 | Altshuler et al. |
| 2006/0036300 A1 | 2/2006 | Kreindel |
| 2006/0111744 A1 | 5/2006 | Makin et al. |
| 2006/0112698 A1 | 6/2006 | Cazzini et al. |
| 2006/0129209 A1 | 6/2006 | McDaniel |
| 2006/0151485 A1 | 7/2006 | Cronin |
| 2006/0161228 A1 | 7/2006 | Lach |
| 2006/0167498 A1 | 7/2006 | Dilorenzo |
| 2006/0184205 A1 | 8/2006 | Schuler et al. |
| 2006/0189964 A1 | 8/2006 | Anderson et al. |
| 2006/0206110 A1 | 9/2006 | Knowlton et al. |
| 2006/0259102 A1 | 11/2006 | Slatkine |
| 2006/0264926 A1 | 11/2006 | Kochamba |
| 2006/0265034 A1 | 11/2006 | Aknine et al. |
| 2006/0271028 A1 | 11/2006 | Altshuler et al. |
| 2006/0276860 A1 | 12/2006 | Ferren et al. |
| 2007/0010810 A1 | 1/2007 | Kochamba |
| 2007/0016032 A1 | 1/2007 | Aknine |
| 2007/0020355 A1 | 1/2007 | Schlebusch et al. |
| 2007/0049918 A1 | 3/2007 | Van Der Weide et al. |
| 2007/0060989 A1 | 3/2007 | Deem et al. |
| 2007/0078290 A1 | 4/2007 | Esenaliev |
| 2007/0078502 A1 | 4/2007 | Weber et al. |
| 2007/0088413 A1 | 4/2007 | Weber et al. |
| 2007/0179482 A1 | 8/2007 | Anderson |
| 2007/0179535 A1 | 8/2007 | Morrissey et al. |
| 2007/0208399 A1 | 9/2007 | Turner et al. |
| 2007/0233226 A1 | 10/2007 | Kochamba et al. |
| 2007/0237620 A1 | 10/2007 | Mühlhoff et al. |
| 2007/0239140 A1 | 10/2007 | Chechelski et al. |
| 2007/0255355 A1 | 11/2007 | Altshuler et al. |
| 2007/0255362 A1 | 11/2007 | Levinson et al. |
| 2007/0265585 A1 | 11/2007 | Joshi et al. |
| 2007/0270925 A1 | 11/2007 | Levinson |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0091183 A1 | 4/2008 | Knopp et al. |
| 2008/0119830 A1 | 5/2008 | Ramstad et al. |
| 2008/0154259 A1 | 6/2008 | Gough et al. |
| 2008/0167585 A1 | 7/2008 | Khen et al. |
| 2008/0195000 A1 | 8/2008 | Spooner et al. |
| 2008/0228526 A1 | 9/2008 | Locke et al. |
| 2008/0294152 A1 | 11/2008 | Altshuler et al. |
| 2008/0319437 A1 | 12/2008 | Turner et al. |
| 2009/0221999 A1 | 9/2009 | Shahidi |
| 2009/0299361 A1 | 12/2009 | Flyash et al. |
| 2009/0306659 A1 | 12/2009 | Buysse |
| 2010/0114086 A1 | 5/2010 | Deem et al. |
| 2010/0211059 A1 | 8/2010 | Deem et al. |
| 2011/0028898 A1 | 2/2011 | Clark, III et al. |
| 2011/0112520 A1 | 5/2011 | Kreindel |
| 2011/0196365 A1 | 8/2011 | Kim et al. |
| 2011/0313412 A1 | 12/2011 | Kim et al. |
| 2012/0078141 A1 | 3/2012 | Knowlton |
| 2013/0150844 A1 | 6/2013 | Deem et al. |
| 2014/0180271 A1 | 6/2014 | Johnson et al. |
| 2015/0148792 A1 | 5/2015 | Kim et al. |
| 2015/0351838 A1 | 12/2015 | Deem et al. |
| 2016/0045755 A1 | 2/2016 | Chun et al. |
| 2016/0135888 A1 | 5/2016 | Kim et al. |
| 2016/0157934 A1 | 6/2016 | Kim et al. |
| 2016/0213426 A1 | 7/2016 | Ben-Haim et al. |
| 2017/0252105 A1 | 9/2017 | Deem et al. |

FOREIGN PATENT DOCUMENTS

| | | |
|---|---|---|
| CN | 1781462 A | 6/2006 |
| EP | 0139607 B1 | 4/1990 |
| EP | 0370890 B1 | 11/1995 |
| EP | 1346753 A2 | 9/2003 |
| JP | 61-364 A | 1/1986 |
| JP | 62-149347 | 9/1987 |
| JP | S-63177856 A | 7/1988 |
| JP | 07-503874 A | 4/1995 |
| JP | H09-239040 A | 9/1997 |
| JP | 2001-514921 A | 9/2001 |
| JP | 2006503618 | 2/2006 |
| JP | 2006-289098 | 10/2006 |
| JP | 2007191192 A | 8/2007 |
| JP | 2010524587 A | 7/2010 |
| WO | WO 89/02292 A1 | 3/1989 |
| WO | WO 92/07622 A1 | 5/1992 |
| WO | WO 96/23447 A1 | 8/1996 |
| WO | WO 96/41579 A1 | 12/1996 |
| WO | WO 99/46005 A1 | 9/1999 |
| WO | WO 00/24463 A2 | 5/2000 |
| WO | WO 01/58361 A1 | 8/2001 |
| WO | WO 03/039385 A2 | 5/2003 |
| WO | WO 2004/034925 A2 | 4/2004 |
| WO | WO 2005/060354 A2 | 7/2005 |
| WO | WO 2005/099369 A2 | 10/2005 |
| WO | WO 2005/112807 A2 | 12/2005 |
| WO | WO 2005/120379 A2 | 12/2005 |
| WO | WO2005/122694 A2 | 12/2005 |
| WO | WO 2006/089227 A2 | 8/2006 |
| WO | WO 2006/090217 A1 | 8/2006 |
| WO | WO 2006/117682 A2 | 11/2006 |
| WO | WO 2006/122136 A2 | 11/2006 |
| WO | WO 2007/015247 A2 | 2/2007 |
| WO | WO 2007/030367 A2 | 3/2007 |
| WO | WO 2007/038567 A1 | 4/2007 |
| WO | WO 2007/050572 A2 | 5/2007 |
| WO | WO2007/093998 A1 | 8/2007 |
| WO | WO 2007/106339 A2 | 9/2007 |
| WO | WO 2007/108516 A1 | 9/2007 |
| WO | WO 2007/131112 A2 | 11/2007 |
| WO | WO 2007/140469 A2 | 12/2007 |
| WO | WO2008/068485 A2 | 6/2008 |
| WO | WO 2009/072108 A2 | 6/2009 |

OTHER PUBLICATIONS

Zhou et al.; Resection of Meningiomas with Implantable Microwave Coagulation; Bioelectromagnetics; vol. 17; No. 2; pp. 85-88; (year of publication is sufficiently earlier than the effective U.S. filing date and any foreign priority date) 1996.

Acculis; Microwave Ablation for Healthcare Professionals; 2 pgs.; accessed Jun. 24, 2008; (http://www.acculis.com/mta).

Aesthera US—How it Works; 2 pgs.; accessed Jul. 8, 2008 (http://www.aesthera.com/go/aestheralUS/patients/how_it_works/index.cfm).

Allergan Pharmaceuticals; Botox® (product insert); 16 pgs.; Oct. 2006.

Alster et al.; Improvement of neck and cheek laxity with a non-ablative radiofrequency device: a lifting experience; Dermatol Surg; 30(4); pp. 503-507; Apr. 2004.

Arneja et al.; Axillary hyperhidrosis: a 5-year review of treatment efficacy and recurrence rates using a new arthroscopic shaver technique; Plast. Reconstr. Surg.; vol. 119; pp. 562-567; Feb. 2007.

Ashby et al.; Cryosurgery for Axillary Hyperhidrosis; British Medical Journal Short Reports; London; pp. 1173-1174; Nov. 13, 1976.

Atkins et al.; Hyperhidrosis: A Review of Current Management; Plast Reconstr Surg; 110(1); pp. 222-228; Jul. 2002.

Ball, P.; Radio sweat gland—90 GHz; Nature; 452(7188); p. 676; Apr. 9, 2008; printed Jun. 18, 2012 from website (http://www.nature.com/news/2008/080409/full/452676a.html).

Zelickson et al.; Ultrastructural effects of an infrared handpiece on forehead and abdominal skin; Dermatol Surg; 32(7); pp. 897-901; Jul. 2006.

Zelickson et al.; Histological and ultrastructural evaluation of the effects of a radiofrequency-based nonablative dermal remodeling device; Arch Dermatol; 140; pp. 204-209; Feb. 2004.

Beer et al., Immunohistochemical Differentiation and Localization Analysis of Sweat Glands in the Adult Human Axilla, Plastic and Reconstructive Surgery, vol. 117, No. 6, pp. 2043-2049, May 2006.

Bentel et al.; Variability of the depth of supraclavicular and axillary lymph nodes in patients with breast cancer: is a posterior axillary boost field necessary?; Int J Radiation Oncology Biol Phys; vol. 47(3); pp. 755-758; Jun. 2000.

(56) References Cited

OTHER PUBLICATIONS

Bindu et al.; Microwave characterization of breast-phantom materials; Microwave and Optical Tech. Letters; 43(6); pp. 506-508; Dec. 20, 2004.
Bioportfolio; Tenex Health Receives FDA clearance for innovative TX1} tissue removal system; 2 pgs.; release dated Mar. 9, 2011; printed on Jun. 18, 2012 from website (http://www.bioportfolio.com/news/article/519143/Tenex-Health-Receives-Fda-Clearance-For-Innovative-Tx1-Tissue-Removal-System.html).
Blanchard et al.; Relapse and morbidity in patients undergoing sentinel lymph node biopsy alone or with axillary dissection for breast cancer; Arch Surg; vol. 138; pp. 482-488; May 2003.
Brace et al., Microwave Ablation with a Trixial Antenna: Results in ex vivo Bovine Liver, IEEE transactions on Microwave Theory and Techniques, vol. 53, No. 1, pp. 215-220 (Jan. 2005).
Yang et al.; A Floating Sleeve Antenna Yields Localized Hepatic Microwave Ablation; IEEE Transactions on Biomedical Engineering; 53(3); pp. 533-537; Mar. 2006.
Burns, Jay A.; Thermage: monopolar radiofrequency; Aesthetic Surg J; 25(6); pp. 638-642; Nov./Dec. 2005.
Campbell et al.; Dielectric properties of female human breast tissue measured in vitro at 3.2 GHz; Phys. Med. Biol.; 37(1); pp. 193-210; Jan. 1992.
Candela Corp.; The Candela SeleroPLUS Laser with Dynamic Cooling Device: The Benefits of Anesthesia without the Risks; Nov. 1998.
Chang et al.; A conductive plastic for simulating biological tissue at microwave frequencies; IEEE Trans on Electromagnetic Compatibility; 42(1); pp. 76-81; Feb. 2000.
Christ et al., Characterization of the Electromagnetic Near-Field Absorption in Layered Biological Tissue in the Frequency Range from 30 MHz to 6000 MHz, Phys. Med. Biol. 51, pp. 4951-4965; Oct. 2006.
Christ et al., The Dependence of Electromagnetic Far-Field Absorption on Body Tissue Composition in the Frequency Range from 300 MHz to 6 GHz, IEEE Transactions on Microwave Theory and Techniques, vol. 54, No. 5, pp. 2188-2195 (May 2006).
CK Electronic GmbH; Scientific Measurements of Skin and Hair (product information); 15 pgs.; published after Sep. 2006.
Cobham; Antenna & Radome Design Aids (product list); 1 pg.; Aug. 2001.
Copty et al., Low-power near-field microwave applicator for localized heating of soft matter, Applied Physics Letters, vol. 84, No. 25, pp. 5109-5111 (Jun. 21, 2004).
Wright et al.; Hepatic microwave ablation with multiple antennae results in synergistically larger zones of coagulation necrosis; Ann. Surg. Oncol.; 10(3); pp. 275-283; Apr. 2003.
Wikipedia; Bayonet mount; 6 pages; Dec. 18, 2014; retrieved from the internet (www.http://en.wikipedia.org/wiki/Bayonet mount).
De Bruijne et al., Effects of waterbolus size, shape and configuration on the SAR distribution pattern of the Lucite cone applicator, International Journal of Hyperthermia, 22(1): 15-28 (Feb. 2006).
Diederich et al.; Pre-clinical Evaluation of a Microwave Planar Array Applicator for Superficial Hyperthermia; International Journal of Hyperthermia; vol. 9, No. 2; pp. 227-246; Jan. 1993.
Drozd et al.; Comparison of Coaxial Dipole Antennas for Applications in the Near-Field and Far-Field Regions; MW Journal, vol. 47, No. 5 (May 2004), http://www.mwjournal.com/Journal, accessed Dec. 10, 2007.
Duparc et al.; Anatomical basis of the variable aspects of injuries of the axillary nerve (excluding the terminal branches in the deltoid muscle); Surg Radiol Anat; vol. 19(3); pp. 127-132; May 1997.
Eleiwa et al.; Accurate FDTD simulation of biological tissues for bio-electromagnetic applications; IEEE Proc. SoutheastCon 2001; Clemson, SC; Mar. 30-Apr. 1, 2001; pp. 174-178.
Farace et al.; An automated method for mapping human tissue permittivities by MRI in hyperthermia treatment planning; Phys. Med. Biol.; 42(11); pp. 2159-2174; Nov. 1997.

Fitzpatrick et al.; Multicenter study of noninvasive radiofrequency for periorbital tissue tightening; Lasers Surg Med; 33(4); pp. 232-242; Mar. 2003.
Gabriel et al.; Dielectric parameters relevant to microwave dielectric heating; Chem Soc Rev; 27(3); pp. 213-224; May-Jun. 1998.
Gabriel et al.; The dielectric properties of biological tissues: I. Literature survey; Phys Med Biol; 41(11); pp. 2231-2249; Nov. 1996.
Gabriel et al.; The dielectric properties of biological tissues: II. Measurements in the frequency range 10 Hz to 20 GHz; Phys Med Biol; 41(11); pp. 2251-2269; Nov. 1996.
Gabriel et al.; The dielectric properties of biological tissues: III. Parametric models for the dielectric spectrum of tissues; Phys Med Biol; 41(11); pp. 2271-2293; Nov. 1996.
Gabriel, et al.; Comparison of the Dielectric Properties of Normal and Wounded Human Skin Material; Bioelectromagnetics; 8; pp. 23-27; Jan. 1987.
Gabriel; Compilation of the dielectric properties of body tissues at RF and microwave frequencies (Technical Report); Armstrong Laboratory; Doc. No. AL/OE-TR-1996-004; pp. 1-16; Jan. 1996.
Galloway et al.; Ultrasound imaging of the axillary vein—anatomical basis for central venous access; British ournal of Anaesthesia; 90(5); pp. 589-595; May 2003.
Gandhi et al.; Electromagnetic Absorption in the Human Head and Neck for Mobile Telephones at 835 and 1900 MHz; IEEE Transactions on Microwave Theory and Techniques; 44(10); pp. 1884-1897; Oct. 1996.
Gandhi et al.; Electromagnetic Absorption in the Human Head from Experimental 6-GHz Handheld Transceivers; IEEE Trans. on Electromagnetic Compatibility; 37(4); pp. 547-558; Nov. 1995.
Garber, B. B.; Office microwave treatment of enlarged prostate symptoms; 2 pgs.; printed from website (http://www.garber-online.com/microwave-treatment.htm) on Jun. 18, 2012.
Gold et al.; Treatment of Wrinkles and Skin Tightening Using Aluma(TM) Skin Renewal System with Faces(TM)(Functional Aspiration Controlled Electrothermal Stimulation) Technology; Lumens, Inc. (Oct. 2005).
Wonnell et al.; Evaluation of microwave and radio frequency catheter ablation in a myocardium-equivalent phantom model; IEEE Trans. on Biomedical engineering; 39(10); pp. 1086-1095; Oct. 1992.
Guidant Corp.; Guidant microwave surgical ablation system; 1 pg.; © 2004; printed Jun. 18, 2012 from website (http://web.archive.org/web/20070306031424/http://www.ctsnet.org/file/vendors/872/pdf/MicrowaveAblationIFU.pdf).
Guy, Arthur; History of Biological Effects and Medical Applications of Microwave Energy; IEEE Transactions on Microwave Theory and Techniques; 32(9); pp. 1182-1200; Sep. 1984.
Guy, Arthur; Therapeutic Heat and Cold, Fourth Ed.; Chapter 5: Biophysics of High-Frequency Currents and Electromagnetic Radiation; pp. 179-236. Williams and Wilkins (publishers); Apr. 1990.
Guy; Analyses of electromagnetic fields induced in biological tissues by thermographic studies on equivalent phantom models; IEEE Trans on Microwave Theory and Techniques; MTT-19(2); pp. 205-214; Feb. 1971.
Haedersdal et al.; Evidence-based review of hair removal using lasers and light sources; JEADV; vol. 20; pp. 9-20; Jan. 2006.
Hey-Shipton, et al.; The Complex Permittivity of Human Tissue at Microwave Frequencies; Phys. Med. Biol.; 27(8); pp. 1067-1071; Aug. 1982.
Hisada et al.; Hereditary Hemorrhagic Telangiectasia Showing Severe Anemia which was successfully treated with estrogen; International Medicine; vol. 34; No. 6; pp. 589-592; Jun. 1995.
Hornberger et al.; Recognition, diagnosis, and treatment of primary focal hyperhidrosis; J Am Acad Dermatol; vol. 51; pp. 274-286; Aug. 2004.
Houzen et al.; Implanted antenna for an artificial cardiac pacemaker system; Progress in Electromagnetics Research Symposium 2007; Prague, CZ; pp. 51-54; Aug. 27-30, 2007.
Hu, Da Zhang, Electromagnetic Field in Organism of Skin-Fat-Muscle, China Research Institute of Radiowave Propagation IEEE, pp. 807-812 (Aug. 1998).

(56) References Cited

OTHER PUBLICATIONS

Jacobsen et al.; Characteristics of microstrip muscle-loaded single-arm archimedean spiral antennas as investigated by FDTD numerical computations; IEEE Trans. on Biomedical Engineering; 52(2); pp. 321-330; Feb. 2005.

Jacobsen et al.; Characterization of a tranceiving antenna concept for microwave heating and thermometry of superficial tumors; PIER; vol. 18; pp. 105-125; (year of publication is sufficiently earlier than the effective U.S. filing date and any foreign priority date) 1998.

Jacobsen et al.; Dual-mode antenna design for microwave heating and noninvasive thermometry of superficial tissue disease; IEEE Trans. on Biomedical Engineering; 47(11); pp. 1500-1509; Nov. 2000.

Jacobsen et al.; Multifrequency radiometric determination of temperature profiles in a lossy homogeneous phantom using a dual-mode antenna with integral water bolus; IEEE Trans. on Microwave Theory and Techniques; 50(7); pp. 1737-1746; Jul. 2002.

Jacobsen et al.; Nonparametric 1-D temperature restoration in lossy media using tikhonov regularization on sparse radiometry data; IEEE Trans. on Biomedical Engineering; 50(2); pp. 178-188; Feb. 2003.

Jacobsen et al.; Transceiving antenna for homogenious heating and radiometric thermometry during hyperthermia; Electronic Letters; 36(6); pp. 496-497; Mar. 16, 2000.

Johnson et al.; Automatic temperature controller for multielement array hyperthermia systems; IEEE Trans. on Biomedical Engineering; 53(6); pp. 1006-1015; Jun. 2006.

Johnson et al.; Evaluation of a dual-arm Archimedean spiral array for microwave hyperthermia; Int J Hyperthermia; 22(6); pp. 475-490; Sep. 2006.

Juang et al.; Construction of a conformal water bolus vest applicator for hyperthermia treatment of superficial skin cancer; Proc. of the 26th Ann. Int. Conf. of the IEEE EMBS; San Francisco, CA, USA; Sep. 1-5, 2004; pp. 3467-3470.

Kawoos et al., Issues in Wireless Intracranial Pressure Monitoring at Microwave Frequencies, PIERS Online, vol. 3, No. 6, pp. 927-931; (year of publication is sufficiently earlier than the effective U.S. filing date and any foreign priority date) 2007.

Kim et al.; Implanted antennas inside a human body: Simulations, designs, and characterizations; IEEE Trans on Microwave Theory and Techniques; 52(8); pp. 1934-1943; Aug. 2004.

Kirn, T. F.; Researchers seek to quantify thermage efficacy; Dermatologic Surgery; p. 36; Jan. 2007.

Kirsch et al.; Ultrastructure of collagen thermally denatured by microsecond domain pulsed carbon dioxide laser; Arch Dermatol; 134; pp. 1255-1259; Oct. 1998.

Klemm et al.; EM energy absorption in the human body tissues due to UWB antennas; Progress in Electromagnetics Research; PIER; 62; pp. 261-280; (year of pub. sufficiently earlier than effective US filing date and any foreign priority date) 2006.

Kobayashi, T.; Electrosurgery Using Insulated Needles: Treatment of Axillary Bromhidrosis and Hyperhidrosis; Journal of Dermatologic Surgery & Oncology; 14(7) pp. 749-752; Jul. 1988.

Krusen, Frank (M.D.); Samuel Hyde Memorial Lecture: Medical Applications of Microwave Diathermy: Laboratory and Clinical Studies. Proceedings of the Royal Society of Medicine; 43(8); pp. 641-658, May 10, 1950.

Kumaradas et al.; Optimization of a beam shaping bolus for superficial microwave hyperthermia waveguide applicators using a finite element method; Phys. Med. Biol.; 48(1); pp. 1-18; Jan. 7, 2003.

Lagendijk et al; Hyperthermia dough: a fat and bone equivalent phantom to test microwave/radiofrequency hyperthermia heating systems; Phys. Med. Biol.; 30(7); pp. 709-712; Jul. 1985.

Land et al.; A quick accurate method for measuring the microwave dielectric properties of small tissue samples; Phys. Med. Biol.; 37(1); pp. 183-192; Jan. 1992.

Lane et al.; Pressure-Induced Bullae and Sweat Gland Necrosis Following Chemotherapy Induction; The American Journal of Medicine; vol. 117; pp. 441-443; Sep. 15, 2004.

Larson et al.; Microwave treatments for enlarged prostate cause blood pressure surges, study shows; 2 pgs.; Apr. 11, 2008; printed on Jun. 18, 2012 from website (http://web.archive.org/web/20080415000815/http://www.sciencedaily.com/releases/2008/04/080408105820.htm).

Lawrence et al.; Selective Sweat Gland Removal with Minimal Skin Excision in the Treatment of Axillary Hyperhidrosis: A Retrospective Clinical and Histological Review of 15 Patients; British Journal of Dermatology; British Association of Dermatologists; 155(1), pp. 115-118; Jul. 2006.

Lehmann et al.; Therapeutic Heat; Therapeutic Heat and Cold, Fourth Ed.; Chapter 9; pp. 417-581; Williams & Wilkins (publishers), Baltimore, MD; Apr. 1990.

Lowe et al.; Botulinum toxin type A in the treatment of primary axillary hyperhidrosis: A 52-week multicenter double-blind, randomized, placebo-controlled study of efficacy and safety; J Am Acad Dermatol; vol. 56; pp. 604-611; Apr. 2007.

Lowe et al.; Microwave delivery system for lower leg telangiectasia; Journal of Cutaneous Laser Therapy; 2(1); pp. 3-7; Mar. 2000.

Lumenis Inc.; Aluma RF Skin Renewal System (product information); copyright 2007 (PB-1013670); 8 pgs.; Oct. 2007 (printed version).

Maccarini et al.; Advances in microwave hyperthermia of large superficial tumors; Microwave Symposium Digest, IEEE MTT-S International; pp. 1797-1800; Jun. 2005.

Maccarini et al.; Electromagnetic optimization of dual mode antennas for radiometry controlled heating of superficial tissue; Proceedings of SPIE; vol. 5698; Bellingham, WA; pp. 71-81; Jan. 2005.

Maccarini et al.; Optimization of a dual concentric conductor antenna for superficial hyperthermia applications; Proc. of the 26th Ann. Int. Conf. of the IEEE EMBS; San Francisco, CA, USA; Sep. 1-5, 2004; pp. 2518-2521.

Mazzurana et al.; A semi-automatic method for developing an anthropomorphic numerical model of dielectric anatomy by MRI; Phys. Med. Biol.; 48(19); pp. 3157-3170; Oct. 7, 2003.

Michel et al.; Design and Modeling of Microstrip—Microslot Applicators with Several Patches and Apertures for Microwave Hyperthermia; Microwave and Optical Technology Letters; vol. 14, No. 2; pp. 121-125; Feb. 5, 1997.

Mrozowski et al.; Parameterization of media dispersive properties for FDTD; IEEE Trans on Antennas and Propagation; 45(9); pp. 1438-1439; Sep. 1997.

Nagaoka et al.; Development of realistic high-resolution whole-body voxel models of Japanese adult males and females of average height and weight, and application of models to radio-frequency electromagnetic-field dosimetry; Phys. Med. Biol.; 49(1); pp. 1-15; Jan. 7, 2004.

Neuman; SAR pattern perturbations from resonance effects in water bolus layers used with superficial microwave hyperthermia applicators; Int. J. Hyperthermia; 18(3); pp. 180-193; May-Jun. 2002.

Park et al.; A Comparative Study of the Surgical Treatment of Axillary Osmidrosis by Instrument, Manual, and Combined Subcutaneous Shaving Procedures; 41(5); pp. 488-497; Nov. 1998.

Paulides et al.; A Patch Antenna Design for Application in a Phased-Array Head and Neck Hyperthermia Applicator; IEEE Transactions on Biomedical Engineering; 54(11); pp. 2057-2063; Nov. 2007.

Popovic et al.; Dielectric spectroscopy of breast tissue—improved model of the precision open-ended coaxial probe; Proc of the 25th Ann Int Conf of the IEEE EMBS; Cancun, Mexico; pp. 3791-3793; Sep. 17-21, 2003.

Popovic et al.; Response characterization of the precision open-ended coaxial probe for dielectric spectroscopy of breast tissue; 2003 IEEE—Anntennas and Propagation Soc. Int. Symp.; vol. 4; pp. 54-57; Jun. 22-27, 2003.

Pozar, David M.; Electromagnetic Theory (Introduction); Microwave Engineering, Second Edition; John Wiley & Sons, Inc.; p. 1; Aug. 1997.

(56) References Cited

OTHER PUBLICATIONS

Rappaport, C.; Treating Cardiac Disease with Catheter-Based Tissue Heating; IEEE Microwave Magazine; 3(1); pp. 57-64; Mar. 2002.
Riddle et al.; Complex permittivity measurements of common plastics over variable temperatures; IEEE Trans on Microwave Theory and Techniques; vol. 51(3); pp. 727-733; Mar. 2003.
Rolfsnes et al.; Design of spiral antennas for radiometric temperature measurement; Proc. of the 26th Ann. Int. Conf. of the IEEE EMBS; San Francisco, CA, USA; Sep. 1-5, 2004; pp. 2522-2525.
Rosen et al.; Microwaves treat heart disease; IEEE Microw Mag; 8(1); pp. 70-75; Feb. 2007.
Ross et al.; A pilot study of in vivo immediate tissue contraction with CO2 skin laser resurfacing in a live farm pig; Dermatol Surg; 25(11); pp. 851-856; Nov. 1999.
Ross et al.; Comparison of carbon dioxide laser, erbium: Yag laser, dermabrasion, and dermatome A study of thermal damage, wound contraction, and woundhealing in a live pig model: Implications for skin. resurfacing; J Am Acad Dermatol; 42(1); pp. 92-105; Jan. 2000.
Ross et al.; Use of a novel erbium laser in a yucatan minipig: A study of residual thermal damage, ablation, and wound healing as a function of pulse duration; Lasers Surg Med; 30(2); pp. 93-100; Feb. 2002.
Rossetto et al.; Effect of complex bolus-tissue load configurations on SAR distributions from dual concentric conductor applicators; IEEE Trans. on Biomedical Engineering; 46(11); pp. 1310-1319; Nov. 1999.
Saito et al.; Clinical Trials of Interstitual Microwave Hyperthermia by Use of Coaxial-Slot Antenna With Two Slots; IEEE Trans. on Microwave Theory and Techniques; vol. 52; No. 8; pp. 1987-1991; Aug. 2004.
Sherar et al.; Helical antenna arrays for interstitial microwave thermal therapy for prostate cancer: tissue phantom testing and simulations for treatment; Physics in Medicine and Biology; 46(7); pp. 1905-1918; Jul. 2001.
Shimm, D et al.; Hyperthermia in the Treatment of Malignancies; Therapeutic Heat and Cold Fourth Edition edited by Justin Lehmann M.D., Chapter 14, pp. 674-699, Williams & Wilkins Publishers, Baltimore, MD; Apr. 1990.
Sipahioglu et al.; Dielectric properties of vegetables and fruits as a function of temperature, ash, and moisture content; Journal of Food Science; 68(1); pp. 234-239; Jan. 2003.
Solish et al.; A comprehensive approach to the recognition, diagnosis, and severity-based treatment of focal hyperhidrosis: recommendations of the Canadian hyperhidrosis advisory committee; Dermatol Surg; vol. 33; pp. 908-923; Aug. 2007.
Solish et al.; Prospective open-label study of botulinum toxin type A in patients with axillary hyperhodrosis: effects on functional impairment and quality of life; Dermatol Surg; vol. 31(4); pp. 405-413; Apr. 2005.
Solta Medical, Inc.; Study Published in Facial Plastic Surgery Journal Finds Selective Heating of Fibrous Septae Key to Success and Safety of Thermage(R) ThermaCool(TM) System; Thermage® Press Release; 2 pgs.; Jun. 20, 2005.
Soontornpipit et al.; Design of implantable microstrip antenna for communication with medical implants; IEEE Trans on Microwave Theory and Techniques; 52(8); pp. 1944-1951; Aug. 2004.
Spertell et al.; Review of clinical data on hair removal using the MW 2000 microwave delivery system (promotional material); 2000; MW Medical, Inc.; printed from http://www.hairfacts.com/medpubs/mwave/spertell.html on Jun. 23, 2009; 5 pgs.
Spertell; Presentation at the American Academy of Dermatology; MW Medical, Inc.; Mar. 10, 2000; 21 pgs.
Spertell; The application of microwaves to the treatment of cosmetic skin conditions: a technical summary; MW Medical, Inc.; pp. 1-15; May 25, 1999.
SRLI Technologies; BTC-2000} (product information); printed from website: http://www.srli.com/technologies/BTC2000.html on Nov. 16, 2009; 1 pg.

Stauffer et al.; Combination applicator for simultaneous heat and radiation; Proc. of the 26th Ann. Int. Conf. of the IEEE EMBS; San Francisco, CA, USA; Sep. 1-5, 2004; pp. 2514-2517.
Stauffer et al.; Dual mode antenna array for microwave heating and non-invasive thermometry of superficial tissue disease; SPIE Conf. on Thermal Treatment of Tissue with Image Guidance; San Jose, CA; SPIE; vol. 3594; pp. 139-147; Jan. 1999.
Stauffer et al.; Microwave array applicator for rediometry controlled superficial hyperthermia; Proc. of the SPIE; vol. 4247; pp. 19-29; Jun. 2001.
Stauffer et al.; Phantom and animal tissues for modelling the electrical properties of human liver; Int. J. Hyperthermia; 19(1); pp. 89-101; Jan.-Feb. 2003.
Stauffer et al.; Practical induction heating coil designs for clinical hyperthermia with ferromagnetic implants; IEEE Trans. on Biomedical Engineering; 41(1); pp. 17-28; Jan. 1994.
Stauffer et al.; Progress on system for applying simultaneous heat and brachytherapy to large-area surface disease; Proceedings of SPIE; vol. 5698; Bellingham, WA; pp. 82-96; Jan. 2005.
Stauffer et al.; Progress toward radiometry controlled conformal microwave array hyperthermia applicator; Proc. of the 22nd Ann. EMBS Int. Conf.; Chicago, IL; Jul. 23-28, 2000; pp. 1613-1616.
Stauffer, Paul R.; Evolving technology for thermal therapy of cancer; International Journal of Hyperthermia; 21(8); pp. 731-744; Dec. 2005.
Stauffer, Paul R.; Thermal Therapy Techniques for Skin and Superficial Tissue Disease; Critical Reviews; SPIE Optical Engineering Press (Bellingham, WA); vol. CR75; pp. 327-367; Jan. 2000.
Sterzer, Fred, Microwave Medical Devices; IEEE Microwave Magazine, 3(1); pp. 65-70; Mar. 2002.
Stoy et al.; Dielectric properties of mammalian tissues from 0.1 to 100 MHz: a summary of recent data; Phys. Med. Bil.; 27(4); pp. 501-513; Apr. 1982.
Strutton et al.; US prevalence of hyperhidrosis and impact on individuals with axillary hyperhidrosis: Results from a national survey. J Am Acad Dermatol; 51(2); pp. 241-248; Feb. 2004.
Stuchly et al.; Diathermy applicators with circular aperture and corrugated flange; IEEE Trans on Microwave Theory and Techniques; MTT-28(3); pp. 267-271; Mar. 1980.
Stuchly et al.; Dielectric properties of animal tissues in vivo at frequencies 10 MHz-1 GHz; Bioelectromagnetics; 2(2); pp. 93-103; Apr. 1981.
Stuchly et al.; Dielectric properties of animal tissues in vivo at radio and microwave frequencies: comparison between species; Phys. Med. Biol.; 27(7); pp. 927-936; Jul. 1982.
Sullivan et al.; Comparison of measured and simulated data in an annular phased array using an inhomogeneous phantom; IEEE Trans on Microwave Theory and Techniques; 40(3); pp. 600-604; Mar. 1992.
Sullivan et al.; The pig as a model for human wound healing; Wound Repair Regen; 9(2); pp. 66-76; Mar. 2001.
Sunaga et al.; Development of a dielectric equivalent gel for better impedance matching for human skin; Bioelectromagnetics; 24; pp. 214-217; Apr. 2003.
Surowiec et al.; Dielectric properties of breast carcinoma ind the surrounding tissues; IEEE Trans on Biomedical Engineering; 35(4); pp. 257-263; Apr. 1988.
Tavernier et al.; Conductivity and dielectric permittivity of dermis and epidermis in nutrient liquid saturation; Engineering in Medicine and Biology Society; 1992 14th Annual Int. Conf of the IEEE; Paris, France; pp. 274-275; Oct. 29-Nov. 1, 1992.
Thermolase Corp.; 510K Pre-Market Notification (No. K950019) and Product User Manual ThermoLase Model LT100 Q-Switched Nd: YAG, Laser Hair Removal System, Jan. 3, 1995.
Trembly et al.; Combined Microwave Heating and Surface Cooling of the Cornea; IEEE Transactions on Biomedical Engineering; vol. 38; No. 1; pp. 85-91; Jan. 1991.
Urolgix, Inc.; Cooled Thermotherapy + Prostiva RF = Durability + Versatility; 1 pg.; printed Jun. 18, 2012 from website (http://wvvw.urologix.com/).

(56) References Cited

OTHER PUBLICATIONS

Uzunoglu et al.; A 432-MHz Local Hyperthermia System Using an Indirectly Cooled, Water-Loaded Waveguide Applicator; IEEE Trans. on Microwave Theory and Techniques; vol. 35, No. 2; pp. 106-111; Feb. 1987.

Valleylab; Cool-tip} RF Ablation System; (http://www.cool-tiprf.com/physics.html) accessed Jun. 24, 2008.

Van Rhoon et al.; A 433 MHz Lucite Cone Waveguide Applicator for Superficial Hyperthermia; International Journal of Hyperthermia; vol. 14, No. 1; pp. 13-27; Jan.-Feb. 1998.

Vander Vorst et al.; RF/microwave interaction with biological tissues; Hoboken, NJ; John Wiley & Sons, Inc.; pp. 264-305; Jan. 2006.

Vardaxis et al.; Confocal laser scanning microscopy of porcine skin: Implications for human wound healing studies; J Anat; 190(04); pp. 601-611; May 1997.

Virga et al.; Low-profile enhanced-bandwidth PIFA antennas for wireless communications packaging; IEEE Trans on Microwave Theory and Techniques; 45(10); pp. 1879-1888; Oct. 1997.

Vrba, et al.; Evanescent-Mode Applicators (EMA) for Superficial and Subcutaneous Hyperthermia; IEEE Trans. on Biomedical Engineering; vol. 40; No. 5; pp. 397-407; May 1993.

Wikipedia; ISM band; 5 pages; printed Jul. 22, 2014 from website (http://en.wikipedia.org/wiki/ISM_band).

Weiss et al.; Monopolar radiofrequency facial tightening: a retrospective analysis of efficacy and safety in over 600 treatments; J Drugs Dermatol; 5(8); pp. 707-712; Sep. 2006.

Deem et al.; U.S. Appl. No. 15/252,109 entitled "Systems and methods for creating an effect using microwave energy to specified tissue," filed Aug. 30, 2016.

Johnson et al.; U.S. Appl. No. 15/667,461 entitled "Systems, apparatus, methods and procedures for the non-invasive treatment of tissue using microwave energy," filed Aug. 2, 2017.

Deem et al.; U.S. Appl. No. 15/406,496 entitled "Systems and methods for creating an effect using microwave energy to specified tissue," filed Jan. 13, 2017.

Deem et al.; U.S. Appl. No. 16/237,494 entitled "Systems and methods for creating an effect using microwave energy to specified tissue," filed Dec. 31, 2018.

\* cited by examiner

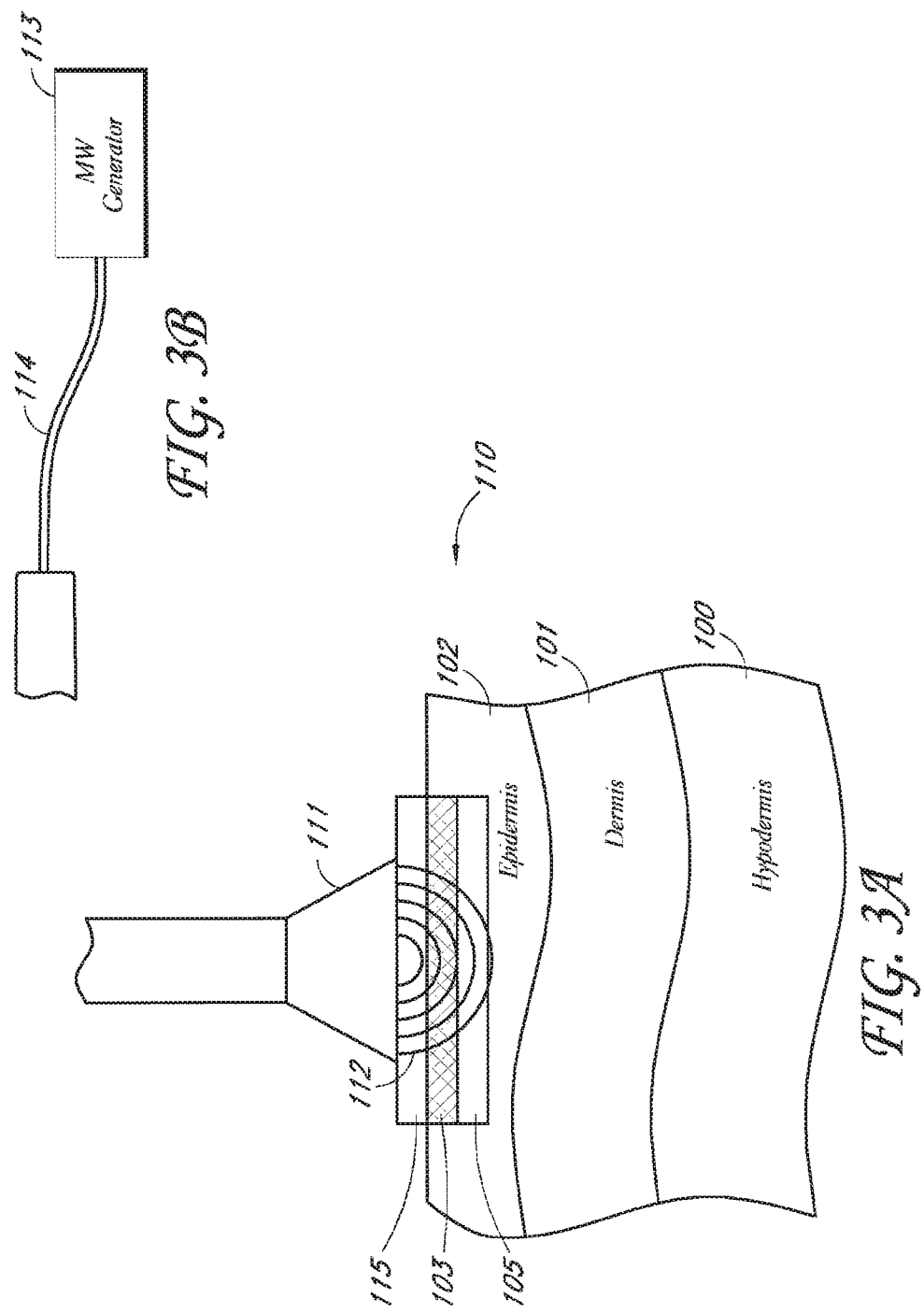

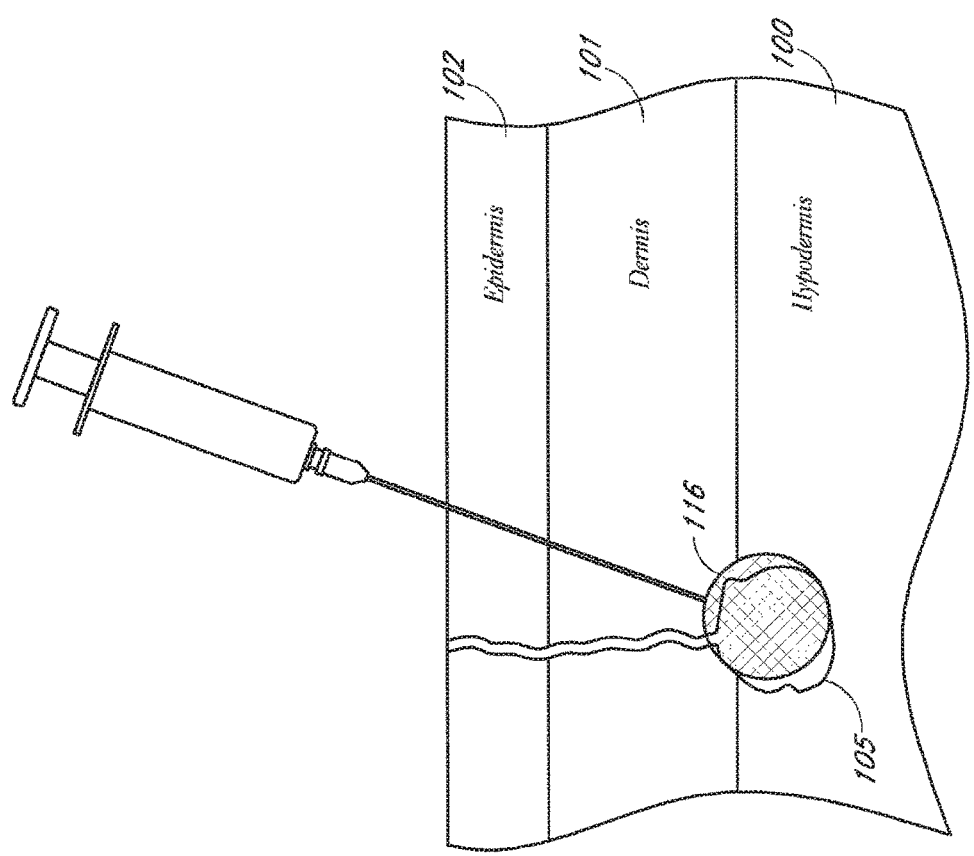

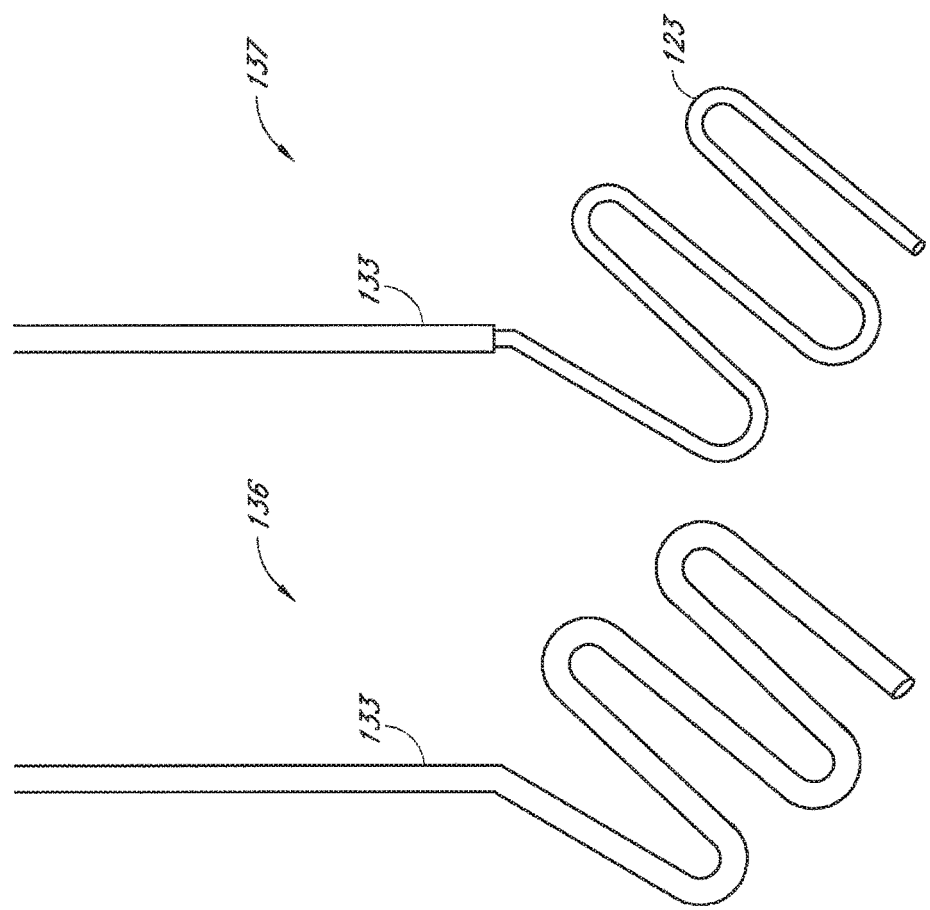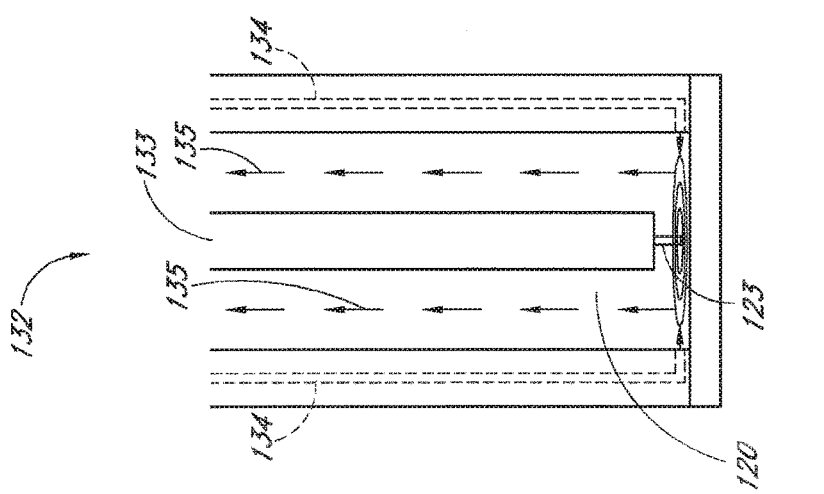

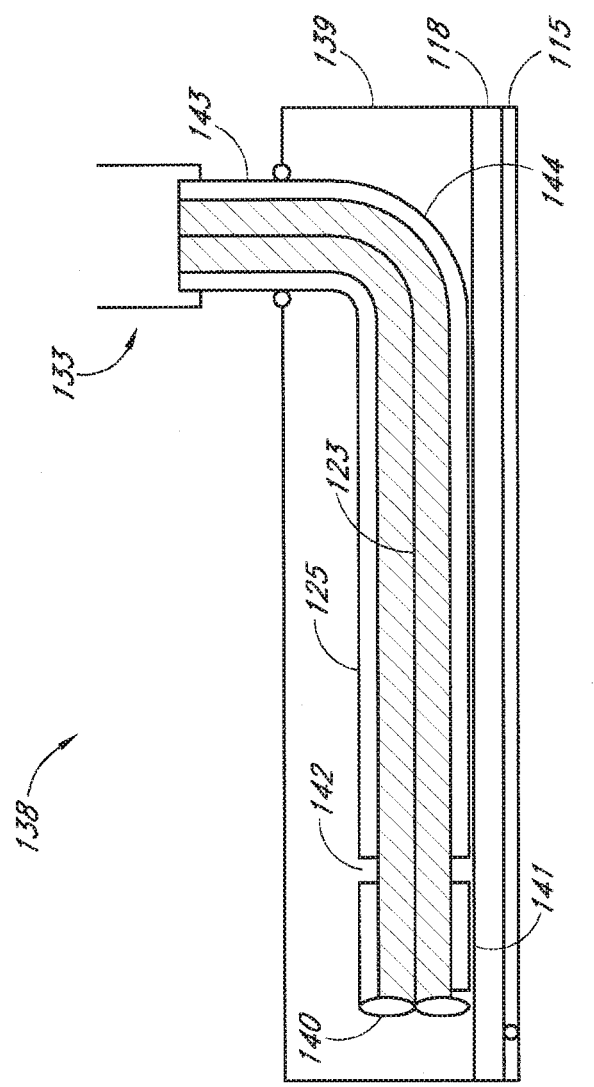

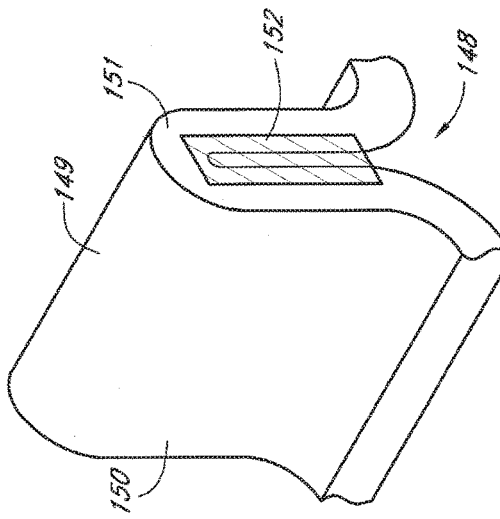
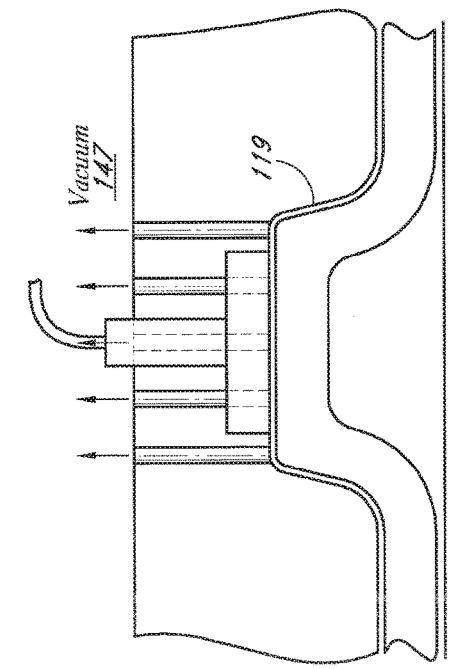
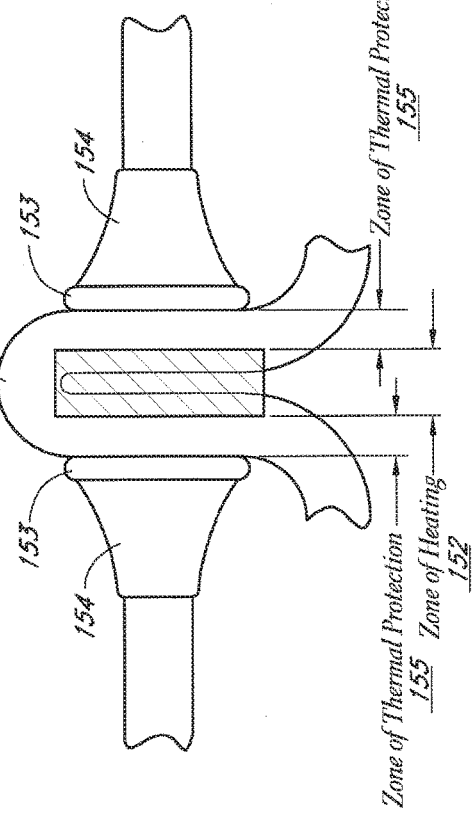

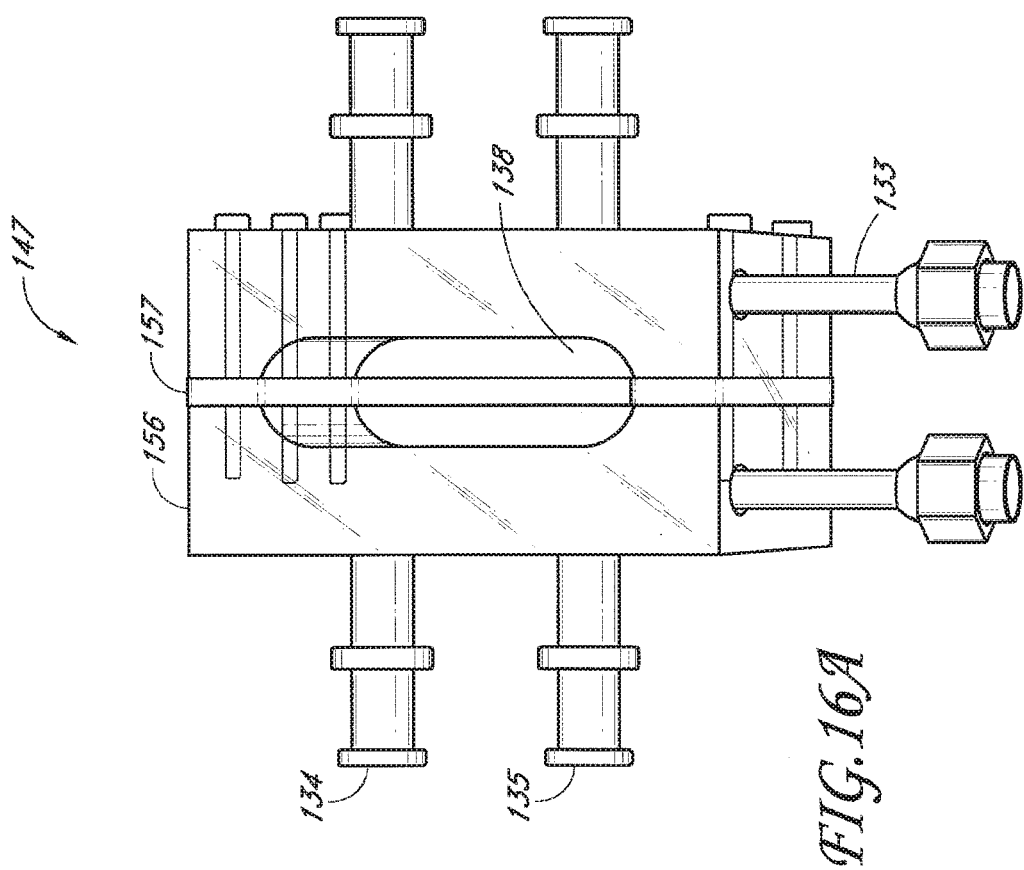

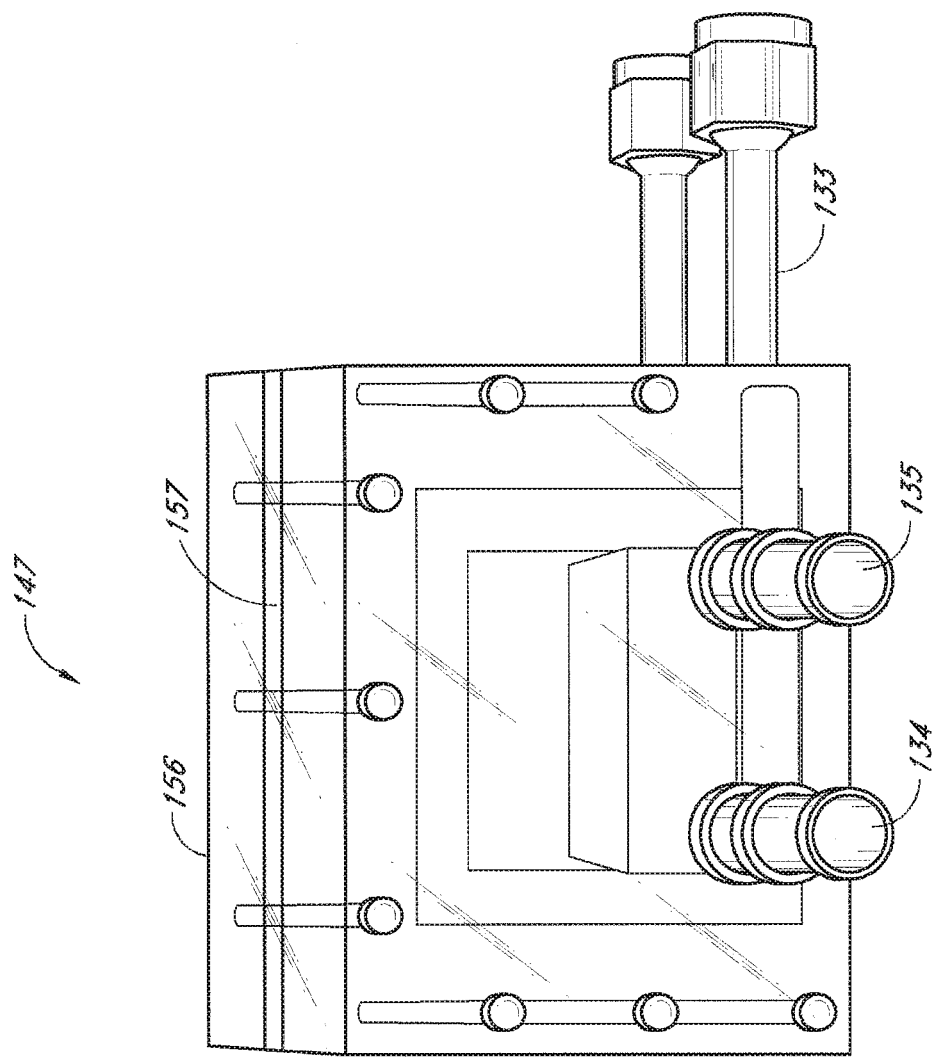

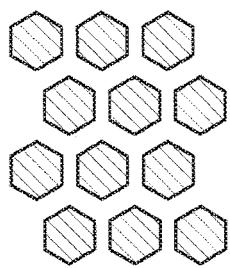
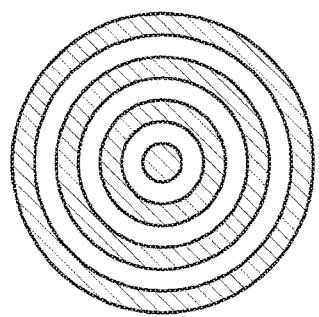
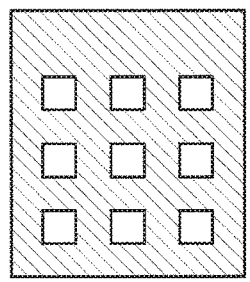
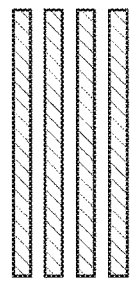
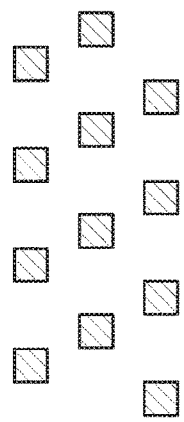
FIG. 18A
FIG. 18B
FIG. 18C
FIG. 18D
FIG. 18E

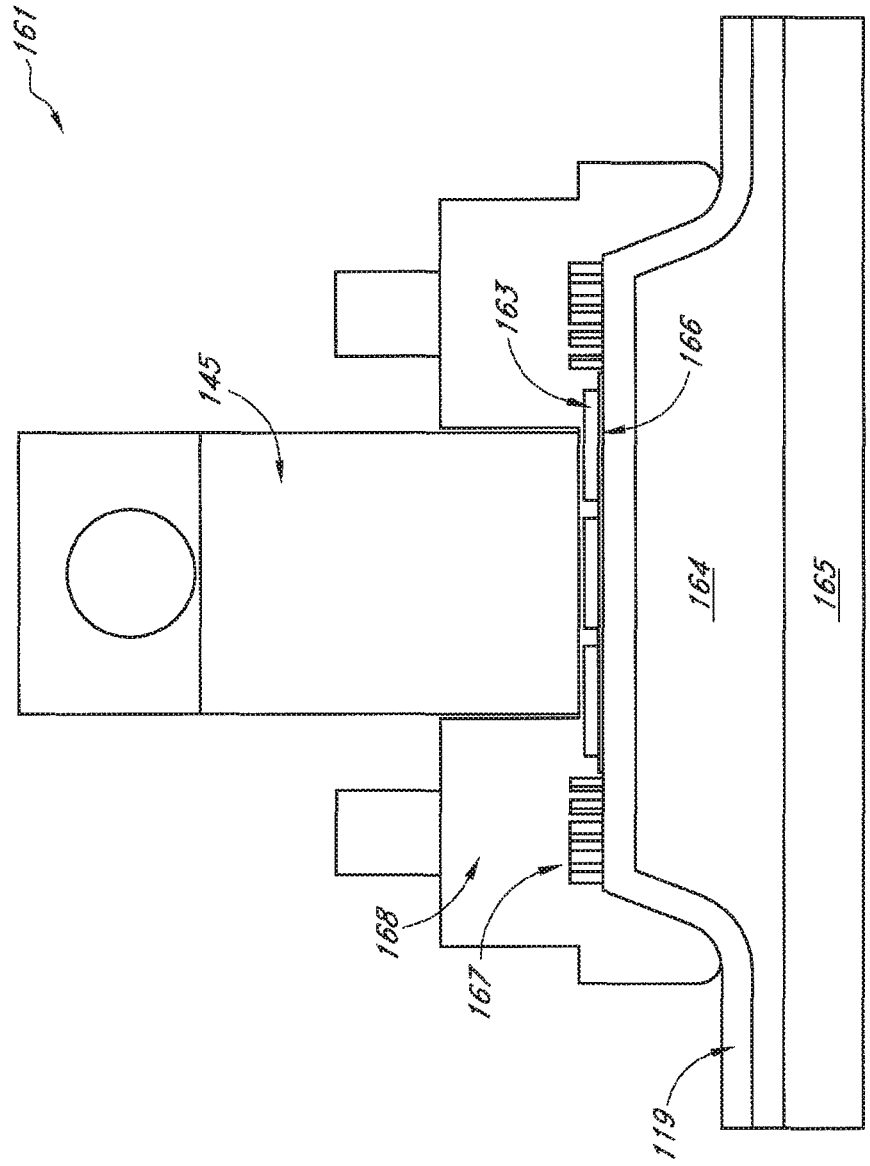

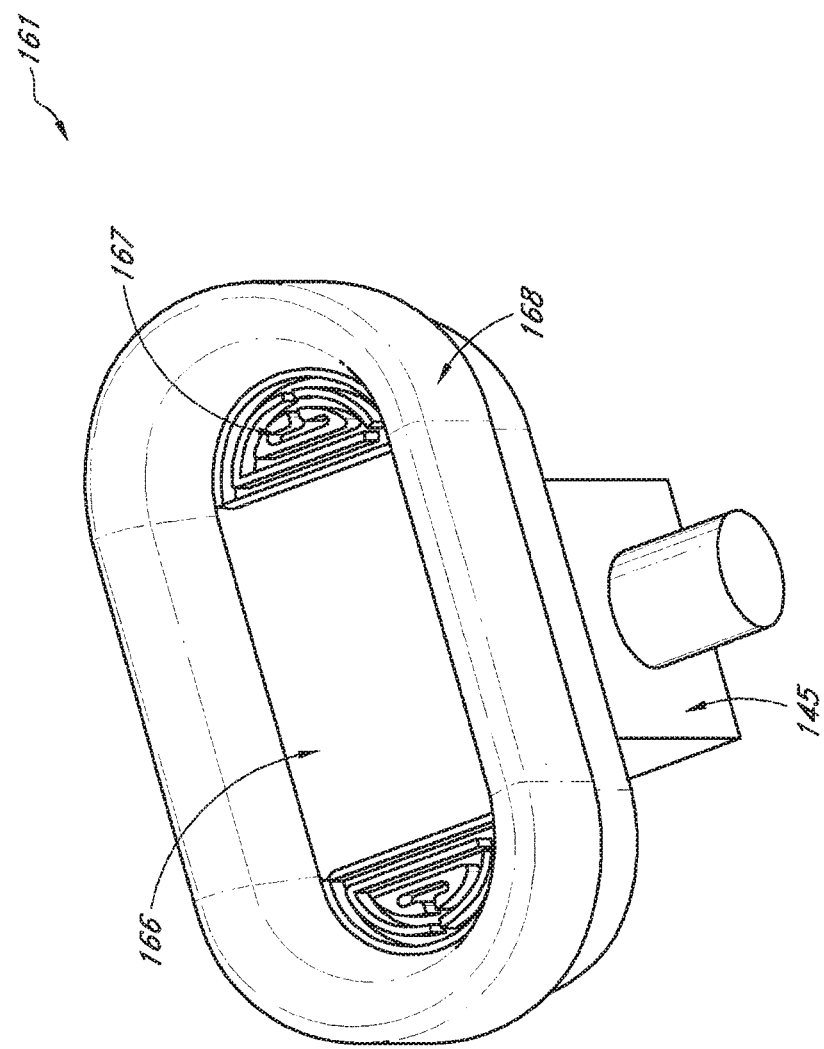

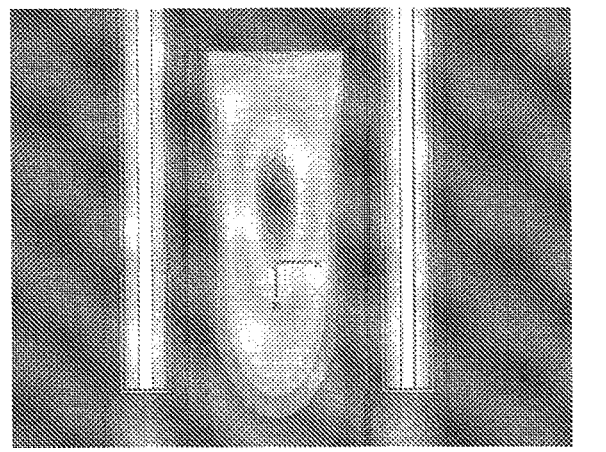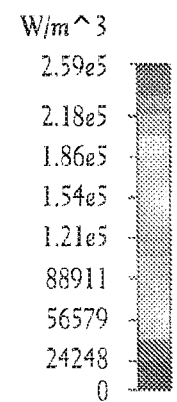
FIG. 24A
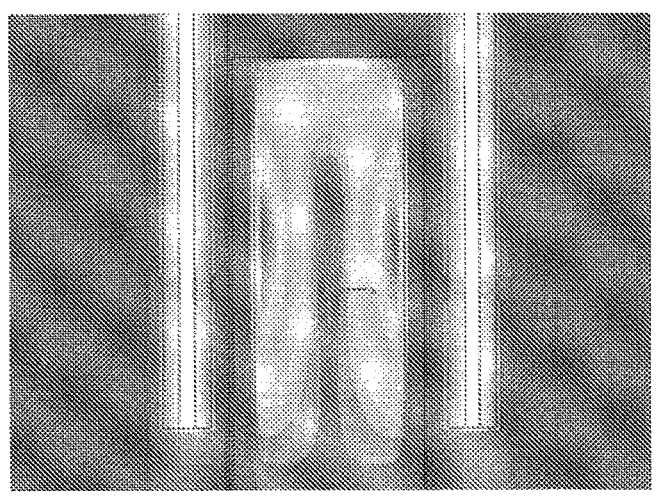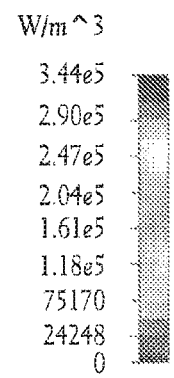
FIG. 24B

METHODS, DEVICES, AND SYSTEMS FOR NON-INVASIVE DELIVERY OF MICROWAVE THERAPY

CROSS-REFERENCE TO RELATED APPLICATIONS

This application is a continuation of U.S. application Ser. No. 12/450,860, filed Oct. 16, 2009, now abandoned, which is a national phase application under 35 USC 371 of PCT/US2008/060929, filed Apr. 18, 2008, which application claims priority under 35 USC 119(e) to U.S. Provisional Patent Application No. 60/912,899, entitled "Methods and Apparatus for Reducing Sweat Production," filed Apr. 19, 2007, U.S. Provisional Patent Application No. 61/013,274, entitled "Methods, Delivery and Systems for Non-Invasive Delivery of Microwave Therapy," filed Dec. 12, 2007, and U.S. Provisional Patent Application No. 61/045,937, entitled "Systems and Methods for Creating an Effect Using Microwave Energy in Specified Tissue," filed Apr. 17, 2008. The entire disclosures of all of the priority applications are hereby expressly incorporated by reference in their entireties.

BACKGROUND

Field of the Invention

The present application relates to methods, apparatuses and systems for non-invasive delivery of microwave therapy. In particular, the present application relates to methods, apparatuses and systems for non-invasively delivering microwave energy to the epidermal, dermal and sub-dermal tissue of a patient to achieve various therapeutic and/or aesthetic results.

Description of the Related Art

It is known that energy-based therapies can be applied to tissue throughout the body to achieve numerous therapeutic and/or aesthetic results. There remains a continual need to improve on the effectiveness of these energy-based therapies and provide enhanced therapeutic results with minimal adverse side effects or discomfort.

BRIEF DESCRIPTION OF THE DRAWINGS

These and other features, aspects and advantages of the various devices, systems and methods presented herein are described with reference to drawings of certain embodiments, which are intended to illustrate, but not to limit, such devices, systems, and methods. It is to be understood that the attached drawings are for the purpose of illustrating concepts of the embodiments discussed herein and may not be to scale.

FIG. 3A shows a device having an energy applicator according to one embodiment.

FIG. 3B shows a microwave generator for supplying the applicator with microwave energy according to one embodiment.

FIG. 4 shows a needle injecting fluid near the base of a sweat gland and target tissue according to one embodiment.

FIG. 8A shows a cross-sectional view of an antenna having an inner conductor disposed within a coaxial cable according to one embodiment.

FIG. 8B shows a coiled antenna having a coiled conductor element formed entirely from a coaxial cable according to one embodiment.

FIG. 8C shows a coiled antenna having a coiled conductor element formed from an inner conductor according to one embodiment.

FIG. 9 shows a cross-sectional view of a slot antenna according to one embodiment.

FIG. 12 shows a side view of a vacuum pulling and holding skin according to one embodiment.

FIG. 13 shows an example of a typical skin fold.

FIG. 14 shows a skin fold being treated by an energy delivery device comprising two energy delivery elements according to one embodiment.

FIG. 16A shows a perspective view of a suction element according to one embodiment.

FIG. 16B shows an alternate perspective view of the suction element of FIG. 16A.

FIGS. 18A, 18B, 18C, 18D and 18E show a variety of patterns illustrating specific areas of treatment and non-treatment sites that could be used over an area of skin.

FIG. 20 shows a schematic of a microwave applicator system including waveguide antenna and tissue capture according to one embodiment.

FIG. 21 shows a schematic of an underside of a waveguide applicator system including waveguide antenna and tissue capture according to one embodiment.

FIG. 24A shows a computer generated image created by simulating two antennas having an in-phase drive operation and focused on treatment of a single area.

FIG. 24B shows a computer generated image created by simulating two antennas having an in-phase drive operation with a 103 degree phase shift between drive signals of a first antenna and a second antenna.

DETAILED DESCRIPTION OF PREFERRED EMBODIMENTS

Overview of Treatments

Disclosed herein are methods, apparatuses and systems for non-invasive delivery of energy-based therapy, which in one embodiment is microwave therapy. The energy-based therapy can be delivered to various target tissues to achieve numerous therapeutic and/or aesthetic results. The terms treatment, treatment effect, treating area/region may relate to the treatment of the target tissue and/or any target structures, wherein the treatment itself may impact the target tissue and/or target structures in one or more of the following ways: modification, deactivation, disablement, denervation, damage, electroporation, apoptosis, necrosis, coagulation, ablation, thermal alteration and destruction. More specifically, reaching a temperature in the target tissue and/or target structures therein of at least about 50° C. or more in one embodiment can be used to achieve a desired treatment effect. Additionally, in one embodiment delivering thermal energy sufficient to heat the target tissue to about 60° C. or more can be used to result in thermal ablation of the target tissue.

Figure 1:
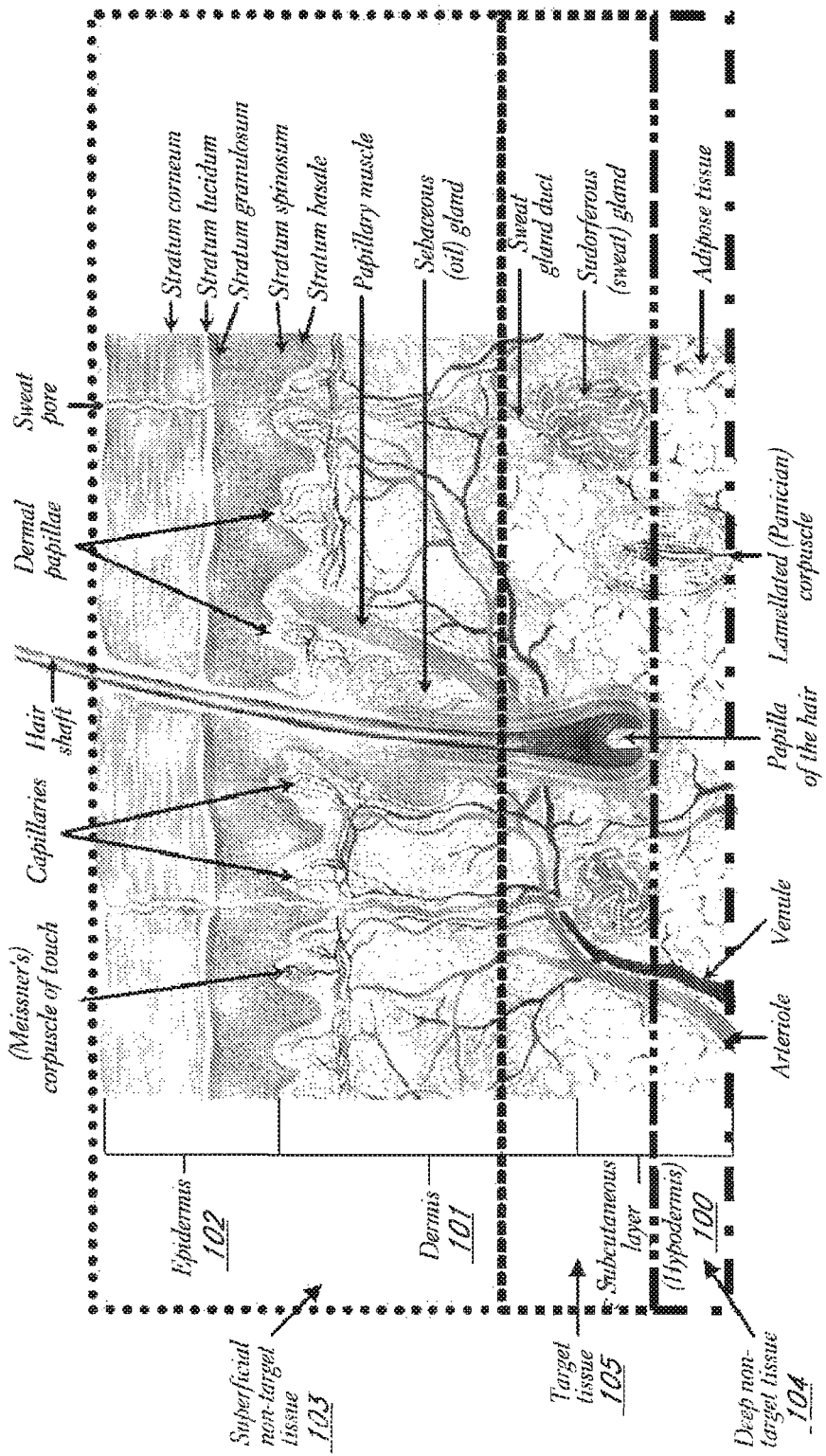
FIG. 1 shows a cross-sectional view of the skin, including schematically demarcated target and non-target tissues, according to one embodiment.

FIG. 1 shows a cross-sectional view of the skin, its three primary layers, the hypodermis 100, dermis 101, and epidermis 102, and internal structures. In certain embodiments it may be desirable to concentrate the treatment within a particular region of dermal 101 and subcutaneous 100 tissue (also referred to herein as the hypodermis) in which the target histological structures reside (e.g., "target tissue"), while doing minimal damage to the tissue above the target tissue in the epidermis 102 and dermis 101 (e.g., "superficial non-target tissue" 103) and tissue structures within the hypodermis 100 (e.g., "deep non-target tissue" 104) as illustrated in FIG. 1 with the various demarcated areas in dotted lines. One or more of the structures may be targeted by the methods and devices disclosed herein.

Figure 2A:
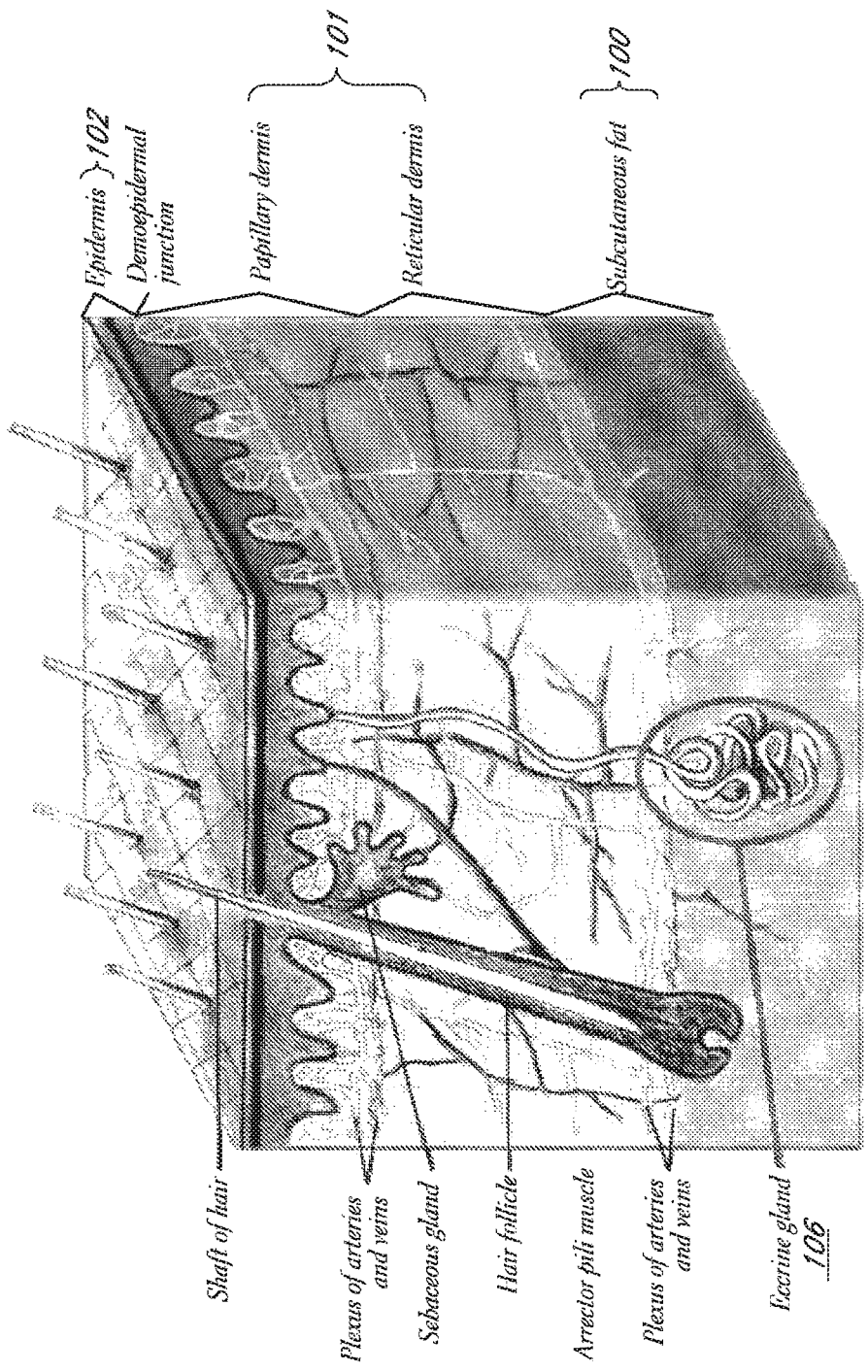
FIG. 2A shows another cross-sectional view of the skin including additional features of interest.

FIG. 2A is another cross-sectional view of the skin, additionally illustrating other body structures, including an eccrine gland 106. As will be discussed further below, eccrine glands 106 are coiled tubular glands which can be found in the deep dermal 101 layers and/or the upper portion of the hypodermis 100. Several million glands are generally present over the surface of the skin, particularly the palms and soles, hairless areas, and axillae. While one gland 106 may have a single duct 109 with a corresponding opening to the surface of the skin, some types of gland variations include twin glands having a common terminal excretory duct, or a single gland having a plurality of excretory ducts (not shown).

Figure 2B:
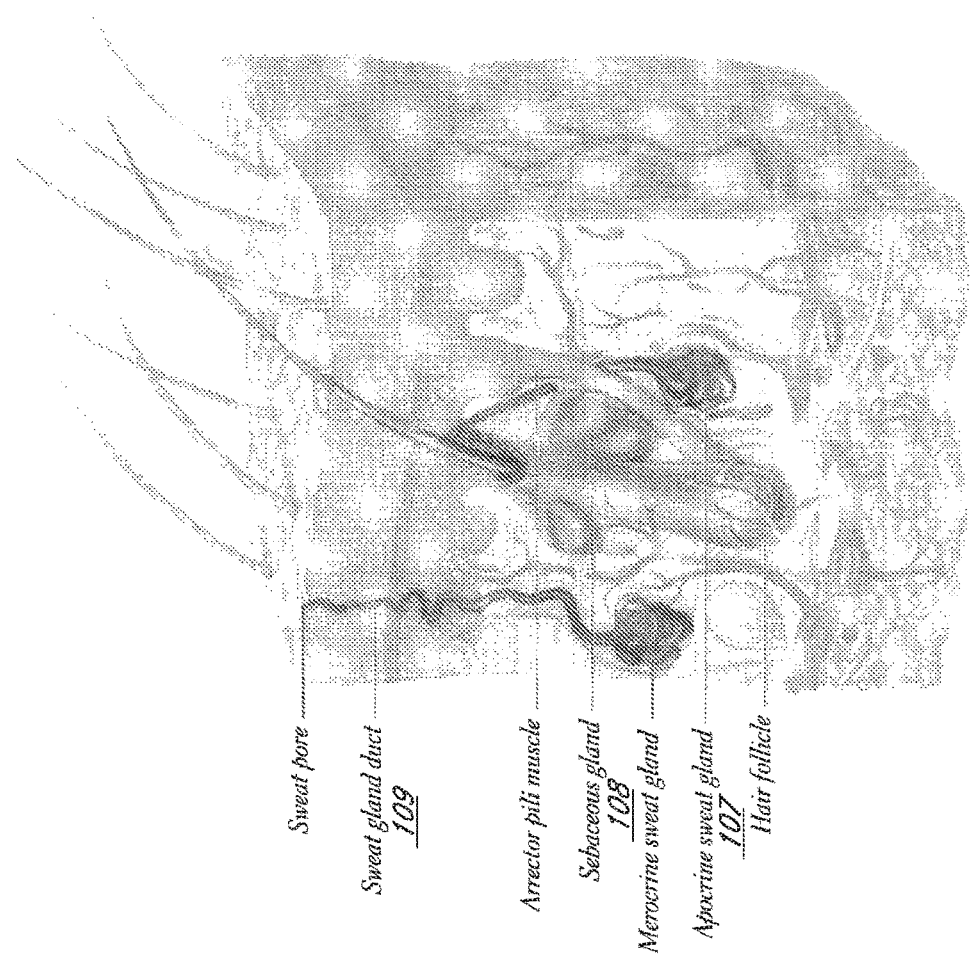
FIG. 2B shows a cross-sectional view of the skin with apocrine and eccrine sweat glands.

FIG. 2B illustrates a cross-sectional view of the skin with both apocrine 107 and eccrine 106 (merocrine) sweat glands. As will be discussed further below, eccrine sweat glands 106 are long tubular extensions from the epidermis 102 which coil into a ball-shaped mass generally in the dermis 101. Apocrine glands 107 are in, for example, the axilla, perianal and pubic areas, scrotum, labia majora and around the nipples. They lie generally in the deep dermis 101 and hypodermis 100 and their ducts 102 terminate in hair follicles. There are myoepithelial cells between the secretory cells of eccrine 106 and apocrine 107 glands and their basement membrane.

Sebaceous glands 108 are pear-shaped glands which empty their oily product, sebum, into the upper portion of hair follicles. Even where several glands open into the same follicle, they are situated at the same level, in the superficial region of the dermis 101. Some sebaceous glands 108 exist independently of hair follicles, opening directly on the skin surface: the lips, the eyelid, the glans penis, the internal fold of the prepuce, the labia minora, and the nipple, for example.

Figure 2C:
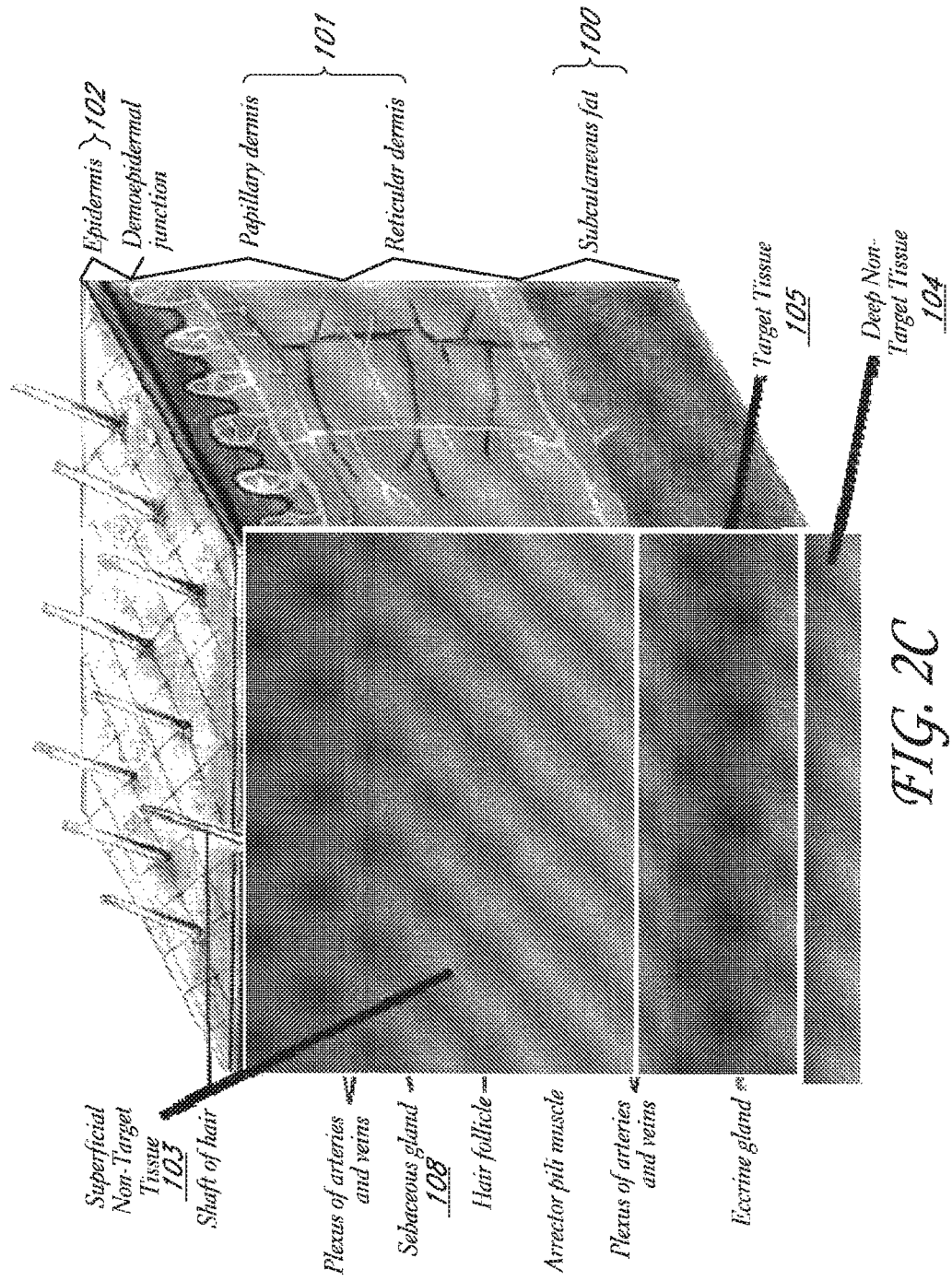
FIG. 2C shows a cross-sectional view of the skin and particular regions of the skin where treatment may be desired.

FIG. 2C shows a cross-sectional view of the skin (as in FIG. 2A) illustrating that in certain embodiments it may be desirable to concentrate the treatment within a particular region of dermal 101 and hypodermis 100 tissue in which the target histological structures reside (e.g., "target tissue" 105) while doing minimal damage to the tissue above the target tissue 105 in the epidermis 102 and dermis 101 (e.g., "superficial non-target tissue" 103) and tissue structures within the hypodermis 100 (e.g., "deep non-target tissue" 104), as shown above to target the eccrine glands 107.

Depending on the area of the body, the target tissue 105 region may begin anywhere from about 0.5 mm to about 4 mm beneath the skin's surface and end anywhere from about 1 mm to about 10 mm beneath the skin's surface in some embodiments. Depending on the area of the body, the superficial non-target tissue 103 region may begin at the skin surface and end anywhere from about 0.5 mm to about 4 mm beneath the skin's surface in some embodiments. Depending on the area of the body, the deep non-target tissue 104 region may begin anywhere from about 1 mm to about 10 mm beneath the skin's surface in some embodiments.

The specific types of tissue structures that will be selected for therapy will depend on the specific therapy or therapies desired. For example, microwave energy can be delivered to the eccrine 106 or apocrine 107 sweat glands to reduce sweating in a patient. Additionally, apocrine glands 107 can be treated to achieve a reduction in body odor. In another embodiment, microwave therapy can be used to shrink collagen in the skin for the purposes of skin tightening, wrinkle reduction and/or body sculpting. In other embodiments, microwave therapy can be used to treat hair follicles, acne, cellulite, vasculature such as varicose veins and telangiectasias, and various other structures disclosed in the application. Accordingly, the location of the target tissue 105 and non-target tissues 103, 104 may require adjustment based on the specific therapy desired.

Clinical Indications

Various non-limiting examples of anatomical structures and clinical indications that can be treated by the systems and methods disclosed herein are listed. In some embodiments, a plurality of structures/disorders can be treated in the same treatment session.

Hyperhidrosis

Hyperhidrosis is a clinically diagnosed disorder in which there is excessive secretion of sweat from the sweat glands. The excessive sweating, which is thought to result from the over activity of the sympathetic nervous system, usually occurs in the palms, soles, and axillae. Palmar hyperhidrosis is a condition of excessive sweating in the hand. This condition is often exhibited in cold, wet handshakes. Plantar hyperhidrosis is a condition of excessive sweating in the foot. This condition may cause blisters and fungal infections. Axillary hyperhidrosis is a condition of excessive sweating in the armpit. Such excessive sweating is not only socially embarrassing but may even cause staining and rotting of clothes.

The sweat glands in the body are comprised of the apocrine 107 and eccrine 106 glands. Eccrine sweat glands 106, which lie superficially in the dermis layer 101 of the skin, are located all over the body so that they can secrete sweat to regulate body heat and temperature. Apocrine glands 107, which exist within the hypodermis 100 and border on the interface between the hypodermis 100 and dermal layer 101, secrete an oily, milky, protein-rich product into the follicles. Bacterial digestion of apocrine sweat is largely responsible for osmidrosis or bromohidrosis (i.e., body odor), which can be most pronounced in the foot and underarm area.

There are various treatments used for treating hyperhidrosis. For example, chemical antiperspirants and deodorants are commonly used as a matter of personal hygiene. Antiperspirants are aluminum based salts that mechanically block the sweat gland ducts, thereby preventing sweat from reaching the skin surface. Deodorants change the pH of the skin surface, thereby minimizing the presence of smell inducing bacteria. Because the effects of both of these products are temporary and can irritate the skin in some users, these products are suboptimal solutions to cases of excessive sweating.

In addition to antiperspirants and deodorants, other topical preparations have been used to treat hyperhidrosis. For example, glutaraldehyde and tannic acid have been used in the treatment of plantar and palmar hyperhidrosis. However, these treatments have generally lost favor because they may cause an unsightly browning of the skin.

Anticholinergic drugs have also been applied both topically and systemically to treat hyperhidrosis. These agents block the sympathetic stimulation of the eccrine glands 148 by inhibiting the action of acetylcholine at the nerve synapse. Use of these drugs is limited because of the systemic side effects they cause, including dry mouth, urinary retention, constipation, and visual disturbances such as mydriasis and cycloplegia. Moreover, topical anticholinergics sometimes have difficulty absorbing into the skin in sufficient quantities to affect the cholinergic nerve endings.

Some patients with hyperhidrosis have resorted to surgical treatments such as sweat gland excision and thoracic sympathectomy. For example, U.S. Pat. No. 5,190,518 to Takasu, which is herein incorporated by reference in its entirety, discloses an ultrasonic surgical device for disabling and excising sweat glands. These treatments may provide for a longer duration of alleviation from hyperhidrosis. However, these treatments are rarely utilized due to their invasive nature, adverse consequences and cost. For example, surgery may cause contractures of the skin, muscle or other surrounding tissue. Sympathectomy may result in complications including infection, pneumothorax, Horner's syndrome, and compensatory hyperhidrosis of the trunk, back and thighs.

Recently, botulinum type-A neurotoxin (e.g., BOTOX™) has proved effective in treating hyperhidrosis in some patients. BOTOX is commonly used by dermatologists to denervate the neuroglandular junctions between the autonomic nerves and the sweat glands. With the nerve connections disabled, acetylcholine is prevented from reaching the eccrine sweat glands 106, thereby disabling a component of the hyperhidrosis patient's overactive sympathetic nervous system. This treatment, however, is not without its downsides. Botulinum toxin is one of the most lethal substances on earth and, consequently, injecting it in a patient's body is full of risk. Additionally, since the apocrine sweat glands 107 are innervated by adrenergic nerves, which are not blocked by botulinum toxin, injections of botulinum toxin do not have a clinical impact on the body odor caused by the secretions from apocrine glands. Botulinum toxin treatment also requires multiple, painful injections with a needle. Furthermore, the results of this treatment last only a few months, thereby necessitating repeated costly and painful treatments.

In light of the shortcomings of the aforementioned approaches, a minimally-invasive, convenient, effective, long-lasting treatment with few side effects would be a desirable alternative for treating hyperhidrosis.

Wrinkles

Wrinkles are also a very common skin condition precipitated by factors including the aging process, UV light exposure, and smoking. As a person ages, the epidermal cells become thinner and less adherent to each other. The thinner cells make the skin look noticeably thinner. The decreased adherency of the cells decreases the effectiveness of the barrier function allowing moisture to be released instead of being kept in the skin, causing dryness. The number of epidermal cells decreases by approximately 10% per decade in some patients and divide more slowly as we age making the skin less able to repair itself quickly.

The effects of aging on the dermal layer 101 are significant. Not only does the dermal layer 101 thin, but also less collagen is produced, and the elastin fibers that provide elasticity wear out. These changes in the scaffolding of the skin cause the skin to wrinkle and sag. Also, over time, sebaceous glands 108 get bigger but produce less sebum, and the number of sweat glands decreases. Both of these changes lead to skin dryness.

The rete-ridges of the dermal-epidermal junction flatten out in the aging process, making the skin more fragile and easier to shear. This process also decreases the amount of nutrients available to the epidermis 102 by decreasing the surface area in contact with the dermis 101, also interfering with the skin's normal repair process.

In the subcutaneous layer 100, fat cells get smaller with age. This leads to more noticeable wrinkles and sagging, as fat cells cannot "fill in" the damage from the other layers.

Ablation of the epidermis 102 can destroy older, damaged epidermal cells, bringing to the surface newer epidermal cells and stimulating collagen formation. Additionally, thermal contracture of deeper collagen fibers can induce overall skin contracture. For instance, contracture of deep dermal collagen and subcutaneous fibrous septae has been suggested as a potential mechanism of action for another thermal wrinkle treatment system marketed by Thermage, Inc. (Hayward, Calif.).

Bromohidrosis

Especially malodorous sweat (bromohidrosis) can occur, especially in the axilla and feet. Bromohidrosis, which is often associated with hyperhidrosis, may occur due to one or more of the following: apocrine gland 107 dysfunction, bacterial and fungal infections, fatty acid decomposition producing a distinctive odor, ingestion of certain foods, and arsenic ingestion. Various treatments are available but are not always ideal or practical, including general cleaning of the body and frequent bathing, changing socks and underwear repeatedly, wearing light clothes, avoidance of excessive sweating, avoidance of excessive consumption of certain types of food such as proteins, garlic, and spices, aeration of the problematic area, using dusting powders particularly for the feet before dressing the socks, using soaks for the feet such as potassium permanganate 1:2000 or formaldehyde solution, and using deodorants and antibacterial antiseptic soap.

Chromohidrosis

Chromohidrosis is abnormally colored sweat due to dysfunction of the apocrine glands 107. Common sites include the face, where the color of sweat may be black, green, blue or yellow in some cases.

Acne

Acne is a disorder of the pilosebaceous unit, which is made up of a hair follicle, sebaceous gland, and a hair. These units are found everywhere on the body except on the palms, soles, top of the feet, and the lower lip. The number of pilosebaceous units is greatest on the face, upper neck, and chest. Sebaceous glands 108 produce a substance called sebum, which is responsible for keeping the skin and hair moisturized. During adolescence, sebaceous glands 108 enlarge and produce more sebum under the influence of hormones called androgens. After about age 20, sebum production begins to decrease. A bacteria, known as *Propionibacterium acnes*, is a normal inhabitant of the skin. It uses sebum as a nutrient for growth, and therefore increases in follicles during puberty.

People with acne may have more *Propionibacterium acnes* in their follicles than people without acne. The presence of bacteria attracts white blood cells to the follicle. These white blood cells produce an enzyme that damages the wall of the follicle, allowing the contents of the follicle to enter the dermis. This process causes an inflammatory response seen as papules (red bumps), pustules, and nodules. The bacteria also cause the formation of free fatty acids, which are irritants, increasing the inflammatory process in the follicle.

Sebum produced by the sebaceous gland 108 combines with cells being sloughed off within the hair follicle and "fills up" the hair follicle. When the follicle is "full", the sebum spreads over the skin surface giving the skin an oily appearance. When this process works correctly, the skin is moisturized and remains healthy.

Problems arise when the sebum is trapped in the hair follicle. For reasons that are still unclear, some hair follicles become obstructed. The sebum is produced but gets trapped on the way out, and the cells that are normally sloughed off become "sticky", plugging up the follicle. The process of obstructing follicles is called comedogenesis. It causes some follicles to form a type of acne called comedones, also known as blackheads and whiteheads.

Various medications have been used for the treatment of acne, including oral and topical retinoids, antibiotics, exfoliants, and surgical dermabrasion, which results in ablation of the stratum corneum layer of the epidermis. More recently, focal thermal therapy has been introduced. Heating individual sites of obstructed follicles and sebaceous glands 108 kills the bacteria within the gland, resulting in reduced inflammation.

Cellulite

Cellulite is the dimpling of the skin, especially in the thigh and buttock regions. Cellulite generally affects women much more frequently than men. Although many therapies that presume cellulite is caused by an abnormality of adipose tissue have gained recent popularity, the basic pathophysiology of cellulite has not been clearly identified. Histopathologic samples have shown cellulite may be the result of irregular extrusion of adipose tissue from the hypodermis 100 into the dermis 101. Traditional therapies such as diet and exercise, and more invasive therapies such as panniculectomy or liposuction each have several disadvantages. A non-invasive way to target dermal adipose tissue without significantly affecting other structures is thus very desirable.

Hair Growth

Unwanted hair growth may be caused by a number of factors including a genetic predisposition in the individual, endocrinologic diseases such as hypertrichosis and androgen-influenced hirsuitism, as well as certain types of malignancies. Individuals suffering from facial hirsuitism can be burdened to an extent that interferes with both social and professional activities and causes a great amount of distress. Consequently, methods and devices for treating unwanted hair and other subcutaneous histological features in a manner that effects a permanent pathological change are very desirable.

Traditional treatments for excessive hair growth such as depilatory solutions, waxing and electrolysis suffer from a number of drawbacks. Depilatory solutions are impermanent, requiring repeated applications that may not be appropriate for sensitive skin. Although wax epilation is a generally safe technique, it too is impermanent and requires repetitive, often painful repeat treatments. In addition, wax epilation has been reported to result in severe folliculitis, followed by permanent keloid scars. While electrolysis satisfactorily removes hair from individuals with static hair growth, this method of targeting individual hairs is both painful and time consuming. In addition, proper electrolysis techniques are demanding, requiring both accurate needle insertion and appropriate intensities and duration. As with wax epilation, if electrolysis techniques are not performed properly, folliculitis and scarring may result.

Recently developed depilatory techniques, utilizing high intensity broad band lights, lasers or photochemical expedients, also suffer from a number of shortcomings. In most of these procedures, the skin is illuminated with light at sufficient intensity and duration to kill the follicles or the skin tissue feeding the hair. The impinging light targets the skin as well as the hair follicles, and can burn the skin, causing discomfort and the potential for scarring. Further, laser and other treatments are not necessarily permanent and may require repeated applications to effect a lasting depilation. Finally, efficacy of these light based therapies relies on a differential between the melanin in the skin and the melanin in the hair. Heat is generated to kill the hair follicles by light absorption of melanin. Thus, in patients with light hair, not enough melanin is present in the hair follicle to generate ablative heat. Conversely, in dark skinned patients, melanin in the skin may absorb so much light that skin ablation occurs simultaneously with hair follicle ablation.

Varicose Veins and Telangiectasias

Like hair follicles, spider veins are subcutaneous features. They exist as small capillary flow paths, largely lateral to the skin surface, which have been somewhat engorged by excessive pressure, producing the characteristic venous patterns visible at the skin surface. Apart from the unsightly cosmetic aspect, telangiecstasia can further have more serious medical implications. Therefore, methods and devices for treating spider veins and other subcutaneous histological features in a manner that effects a permanent pathological change to the appropriate tissues are highly desirable.

The classical treatment for spider veins is sclerotherapy, wherein an injection needle is used to infuse at least a part of the vessel with a sclerotic solution that causes blood coagulation and blockage of the blood path. With time, the spider veins disappear as the blood flow finds other capillary paths. Since there can be a multitude of spider veins to be treated over a substantial area, this procedure is time-consuming, tedious, and often painful. It is also of uncertain effectiveness in any given application and requires a substantial delay before results can be observed.

Another procedure for the treatment of shallow visible veins, which is similar to techniques used in depilation, involves the application of intense light energy for a brief interval. This technique exposes the skin surface and underlying tissue to concentrated wave energy, heating the vein structure to a level at which thermocoagulation occurs. In particular, these energy levels are so high that they cause discomfort to some patients, and can also be dangerous to those in the vicinity, unless special precautions are taken. In addition, some patients can be singed or burned, even though the exposure lasts only a fraction of a second.

Due to the serious problems that the subcutaneous abnormalities can create in individuals, there is a general need to be able to treat such features in a manner that effects beneficial pathological change without adverse side effects or discomfort. An optimal therapeutic technique should effect a permanent pathological change without requiring repeated applications to reach the desired effect. Moreover, these procedures should be non-invasive, should cover a substantial target area that is not limited to a single hair follicle or spider vein, and should make optimum use of the energy available. Finally, pathological changes should occur only in the targeted feature, and not in intervening or underlying layers.

Benign and Malignant Skin Lesions and Infections

Numerous malignant and pre-malignant skin lesions, including actinic keratosis, basal cell carcinoma, squamous cell carcinoma, and melanoma, and benign skin lesions such as cysts, warts, nevi, café au lait spots, and vascular lesions would also benefit from a non-invasive localized treatment. Furthermore, skin and nail infections from bacteria, viruses, fungi, or parasites, could also benefit from a non-invasive local treatment method.

Neurologic Disorders

The hypodermis layer 100 is innervated by sensory nerve endings. A non-invasive local treatment for hyperesthesia, e.g., from neurologic disorders such as, for example, multiple sclerosis and herpes zoster, would also be desirable.

In combination with the thermal treatments disclosed herein, protective treatments can be employed to prevent damage or pain to non-target tissue. In one embodiment, thermal protective treatments may be used. For example, surface cooling can be applied to protect the epidermal layer 102 and portions of the dermal layer 101 of the skin while deeper regions of skin tissue are heated via energy delivery. Various types of active and passive cooling can be configured to provide this thermal protection to non-target tissue 103, 104.

While the above clinical indications have generally focused on the integumentary system (i.e., the skin and associated structures), one of ordinary skill in the art will appreciate that various other anatomical structures can be treated using the disclosed systems and methods. For example, visceral tissues and organs such as the brain, lungs, heart, kidneys, stomach, intestines, gallbladder, pancreas, aorta and other arteries, veins, bladder, prostate, ovaries, uterus, fallopian tubes can also be treated using the embodiments of the present application.

The delivery of therapy may also be facilitated by administering many of the treatments disclosed herein in one or more spatial configurations or skin geometries. For example, treatment can be directed perpendicular to the skin surface, parallel to the skin plane or at some angle in between. Additionally, the skin can be oriented in various configurations to achieve the desired energy delivery. For example, energy can be delivered to the skin in a flat, planar configuration, in an elevated orientation or in a folded geometry. Additionally, suction can be applied to the skin to achieve a particular orientation or geometry.

Microwave therapy may also be facilitated by administering treatment over multiple stages and in a patterned arrangement. This approach can enhance the body's healing response, making for a quicker recovery with fewer complications. Various templates are disclosed to assist in administering a staged and patterned treatment. Microwave therapy may also be facilitated by the introduction into the treatment zone or directly into the target tissues of exogenous microwave absorbers. Some substances, such as graphite, carbon black, or ferrite will preferentially absorb microwaves and increase the local thermal effect.

With reference to the drawings disclosed in this specification, the particulars shown are by way of example and for purposes of illustrative discussion of certain embodiments. In this regard, not all structural details may be shown in detail. Accordingly, it should be understood that the application is not limited to the details of construction and the arrangement of components set forth in the descriptions or illustrations provided herein. Additionally, it should be understood that the terminology used herein is for the purpose of description and should not be regarded as limiting.

The embodiments disclosed herein relate to the treatment of dermal and sub-dermal tissue structures via the transcutaneous delivery of energy. While microwave energy is generally preferred, it should be understood that many other energy modalities can be used to achieve the intended therapy. For example, it may be possible for the apparatuses and systems disclosed herein to be configured to deliver one or more of the following modalities: electromagnetic, x-ray, RF, DC, AC, microwave, ultrasound, including high-intensity focused ultrasound (HIFU), radiation, near infrared, infrared, and light/laser. Non-limiting examples of embodiments directed to non-microwave as well as microwave treatment of the skin and other organs can be found for example, in U.S. Provisional Patent Application No. 60/912,899, entitled "Methods and Apparatus for Reducing Sweat Production," filed Apr. 19, 2007 and U.S. Provisional Patent Application No. 61/013,274, entitled "Methods, Delivery and Systems for Non-Invasive Delivery of Microwave Therapy," filed Dec. 12, 2007, both of which are incorporated by reference in their entireties, particularly seen for example, in FIGS. 8-32 and pp. 14-40 of Application No. 60/912,899. Further microwave systems and methods that can be used with embodiments of the invention are disclosed in, for example, FIGS. 2-25 of App. No. 61/045,937 and the accompanying description at pp. 11-18. The 61/045,937 application has also been previously incorporated by reference in its entirety. Various tissue structures may be targeted as listed above, including sweat glands, sebaceous glands, collagen, hair follicles, cellulite, and vasculature that supplies blood to any of the above.

The system illustrated in FIGS. 3A-B shows a device 110 having an energy applicator 111 for non-invasively delivering microwave energy 112 to the target tissue layer 105 and a microwave generator 113 for supplying the applicator 111 with microwave energy 112 via conduit 114 as shown in FIG. 3B. In this embodiment, the energy applicator 111 comprises at least one antenna for delivering microwave energy 112 to the target tissue 105. The antennas would be configured, when the device is placed against or near the patient's skin, to heat and treat the target tissue 105 and target structures within the target tissue 105. The treated target tissue 105 could either be left in place to be resorbed by the body's immune system and wound healing response or be extracted using any number of minimally invasive techniques. Also illustrated is cooling plate 115 for preventing damage to superficial non-target tissue 103.

Microwave energy 112 is absorbed by the target tissue 105 by a process called dielectric heating. Molecules in the tissue, such as water molecules, are electric dipoles, wherein they have a positive charge at one end and a negative charge at the other. As the microwave energy 112 induces an alternating electric field, the dipoles rotate in an attempt to align themselves with the field. This molecular rotation generates heat as the molecules hit one another and cause additional motion. The heating is particularly efficient with liquid water molecules, which have a relatively high dipole moment.

Since microwave heating is particularly efficient when water molecules are present in tissue, it may be desirable to have a relatively high water content or molecule density at the target tissue or within the target structures. This high water content would result in greater microwave energy absorption and consequent heating at the point of treatment. Moreover, this phenomenon will allow the preferential heating of target tissue 105, thereby minimizing the impact to non-target tissue 103, 104.

There are numerous ways in which water content in the target tissue 105 can be achieved. For example, injecting a bolus of fluid 116 (e.g., water, saline, etc.) into or near the target tissue 105 or target structures would render such areas more susceptible to microwave treatment. FIG. 4 shows one embodiment of the injection of fluid 116 proximate to the base of a sweat gland and target tissue 105. When targeting sweat glands, the patient can be induced to sweat in the area of treatment (such as by raising the ambient temperature or the temperature in the target area) in order to achieve higher water content in the target structures. In any of these cases, the water dense sweat glands can be plugged to prevent any of the water/sweat from escaping through the sweat ducts. Sealing the gland ducts can be achieved by using aluminum ion based topical products such as antiperspirants or any type of biocompatible polymer coating. The addition of external water is not required in some embodiments. Not to be limited by a particular theory, sweat glands naturally have a relatively high water content compared to surrounding tissue which can allow the sweat glands to preferentially absorb microwave energy 112. Furthermore, sweat glands generally have a higher concentration of ions (e.g., a greater ionic potential) relative to surrounding tissue which also advantageously can allow for the preferential absorption of microwave energy with respect to the surrounding tissue.

One of ordinary skill in the art will also appreciate that tissue of relatively low water content (e.g., cellulite) can also be preferentially targeted by microwave energy by aligning the e-field of the radiated signal to preferentially heat the low water content fat layer. Further details regarding controlling the effect of microwave energy on target tissue are found in U.S. Provisional Patent Application No. 60/912,899, entitled "Methods and Apparatus for Reducing Sweat Production," filed Apr. 19, 2007, U.S. Provisional Patent Application No. 61/013,274, entitled "Methods, Delivery and Systems for Non-Invasive Delivery of Microwave Therapy," and U.S. Provisional Patent Application Ser. No. 61/045,937, entitled "Systems and Methods for Creating an Effect Using Microwave Energy in Specified Tissue," filed Apr. 17, 2008, particularly seen for example, in FIGS. 26-51 and pp. 18-33 of Application No. 61/045,937.

Figure 5:
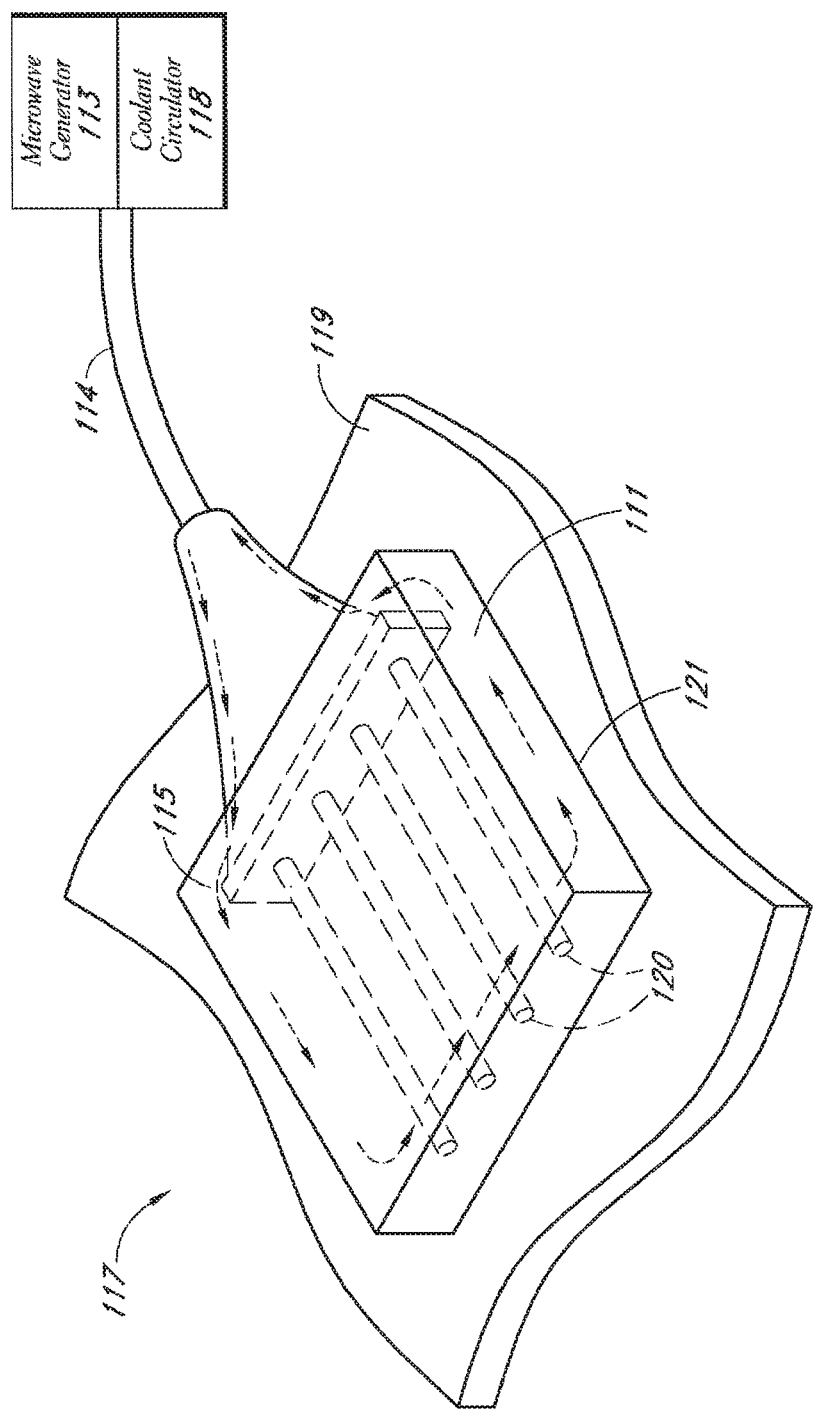
FIG. 5 shows an isometric view of a non-invasive energy delivery device comprising multiple microwave antennas electrically connected to a microwave generator according to one embodiment.

As shown in FIG. 5, an apparatus for treating target tissue 105 with microwave energy can be configured to include a processor (not shown), an energy generator 113 connected to the processor, and a device 117 operatively coupled to the generator. The device 117 can further include an energy delivery applicator 111 or energy delivery element such as an antenna for delivering energy to the target tissue. In an exemplifying embodiment, a cable 114 (e.g., feedline) electrically connects the device to an energy generator 113. In other embodiments, the processor, the device, and/or the energy generator 113 can be connected wirelessly via, for example, radio frequency signals. In a preferred embodiment, the energy generator 113 is remotely located from the energy applicator 111, wherein the generator 113 can be either stationary or mobile. Alternatively, the applicator 111 and generator 113 can be coupled such that they comprise a portable unit. Still alternatively, the applicator 111 and generator 113 can be combined into a single unit.

FIG. 5 is an isometric view depicting one embodiment of a non-invasive energy delivery device 117 comprising multiple microwave antennas 120 that are electrically connected to a microwave generator 113. In one embodiment, the antennas 120 are contained in a substantially planar applicator plate 121 sized for application against a target area of a patient's skin 119. In one embodiment, the device 117 and the applicator plate 121 therein, can be sized and configured to substantially match the area of tissue being treated. Additionally, the applicator plate 121 may be flexible to help the device 117 conform to the contours of the patient's skin.

Figure 6:
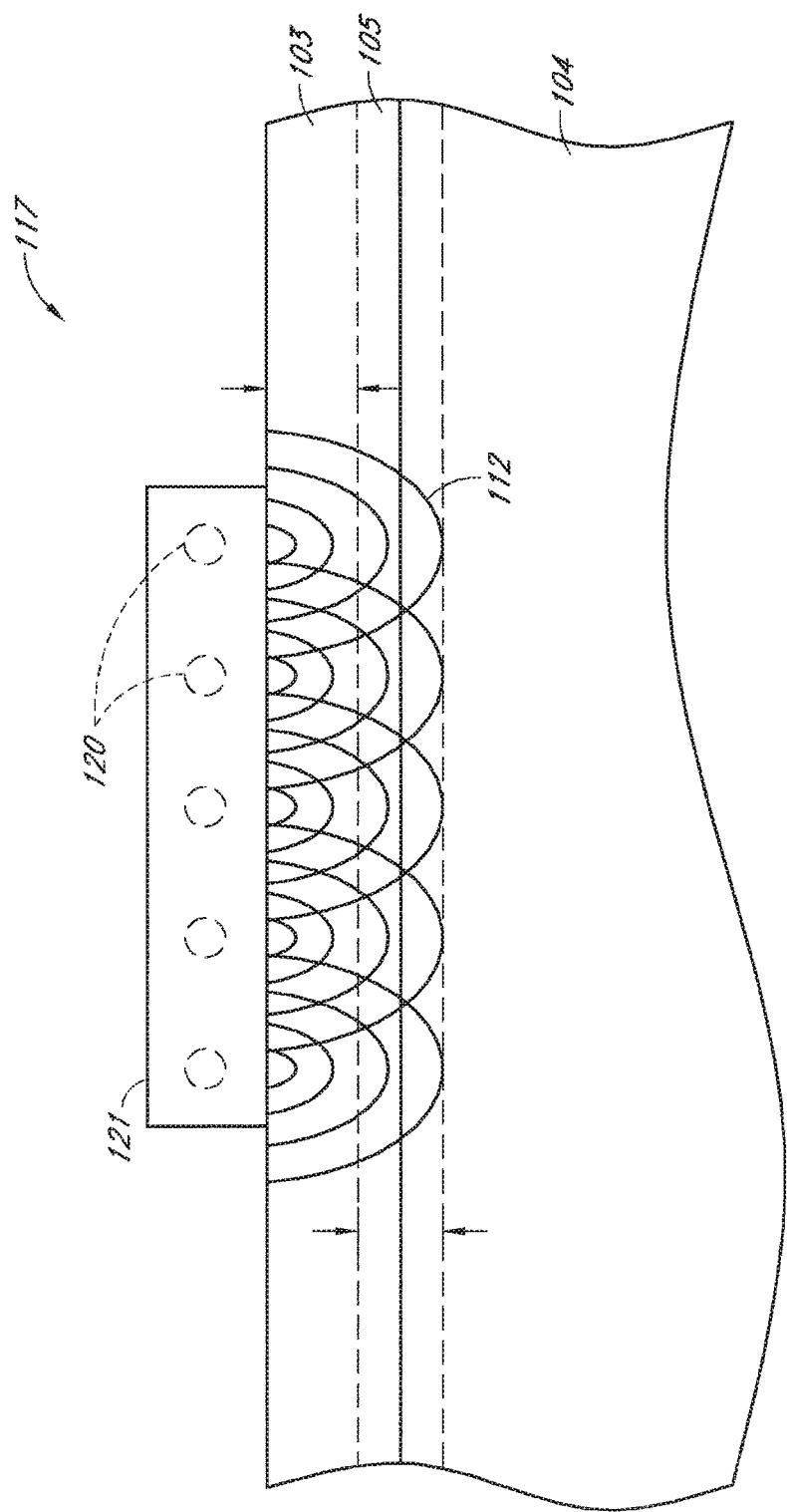
FIG. 6 shows a cross-sectional side view of the non-invasive energy delivery device of FIG. 5 delivering energy into the skin.

FIG. 6 is a cross-sectional side view of the device 117 of FIG. 5 showing the delivery of energy 112 into the skin. In such multi-antenna embodiments, it may be useful to orient the antennas 120 along the same plane in the same longitudinal direction to deliver energy in a planar fashion. As shown in FIGS. 5 and 6, four or five microwave antennas 120 are positioned parallel to each other. In other embodiments, fewer or greater microwave antennas 120 may be provided, for example, one, two, three, or at least four, five, six, seven, eight, nine, ten or more. With this planar configuration, energy 112 can be delivered to a larger area of tissue in one treatment and in a more consistent fashion. In some embodiments, the antenna(s) 120 may be similar to that described in U.S. Pat. Nos. 4,825,880 to Stauffer et al. or U.S. Pat. No. 6,330,479 to Stauffer, which are both hereby incorporated by reference in their entirety.

As discussed later in this specification, thermal protective measures can be employed in conjunction with thermal treatments. As shown in FIGS. 5 and 6, the applicator plate 121 containing the antennas 120 may be connected by a conduit 114 to the microwave generator 113, with cooling fluid passing through the conduit to and from the applicator plate 121 from a coolant circulator 118. The cooling fluid creates a protected zone 103 in the epidermis 102 of the patient, so that target tissue 105 below the protected zone is treated. Protected zone 104 deep to target tissue 105 is also illustrated.

The amount of energy 112 delivered to the target tissue 105 and consequent extent of treatment effect can be adjusted based on the number of antennas 120, their specific configuration and the power delivered to each antenna 120. In one embodiment, a microwave energy output frequency ranging from 300 MHz to 20 GHz would be suitable for feeding the energy delivery device with power. In one embodiment, a microwave signal of anywhere from about 915 MHz to about 2450 MHz would be preferential for yielding a treatment effect on tissue. Alternatively, a signal having a frequency ranging from about 2.5 GHz to about 10 GHz may also be preferential in some embodiments. Additionally, solid state, traveling wave tube and/or magnetron components can optionally be used to facilitate the delivery of microwave energy.

The delivery of energy 112 to the target tissue 105 can be facilitated by antenna 120 designs that incorporate a low-loss dielectric element that can take the form of a stand-off between the antenna 120 and tissue, and/or also a fill-material (e.g., a dielectric filled waveguide). Unlike other forms of electrical energy delivery, such as radiofrequency, where energy is typically transmitted through direct electrical contact between a metal conductor and body tissue, microwave energy can be delivered through a low-loss dielectric material. A properly configured dielectric element will not impede the microwave energy from radiating to adjacent tissue and can be utilized as a design tool to help optimize the delivery of energy to the target tissue over the course of the treatment. Since the dielectric properties (permittivity and conductivity) of skin and underlying tissue can change over the course of a treatment (e.g., as temperature rises) due to loss of moisture, a dielectric element that removes the antenna from direct contact with the skin can help maintain consistent energy delivery to the target tissue by ensuring a consistent load. This is achieved since the dielectric properties of the load in closest proximity to the antenna (i.e., the dielectric element) remain relatively consistent during a treatment compared to that of the skin and underlying tissue. In addition to improving consistency, a low-loss dielectric (e.g., ceramic, PTFE, polyimid, etc.) placed between the tissue and antenna can be utilized to maximize power transfer into the tissue. The dielectric could be incorporated into the antenna itself (e.g., as a fill material), as an external component of the energy delivery device or system (e.g., as a dielectric "block" between the antenna and tissue), or as a combination of both. Further details regarding antenna designs are discussed below.

With respect to antenna design, several possible antenna designs can be implemented to achieve the energy delivery function disclosed herein. In some embodiments, the antenna is built using a section of semi-rigid coaxial cable—with the antenna at one end and a microwave generator at the other end. The antenna is then connected to the generator with a long section of flexible microwave cable. Also, in certain waveguide antenna embodiments, the waveguide antenna can include a section of waveguide tubing with an appropriate shape or geometry depending on the desired clinical result.

Figure 7A:
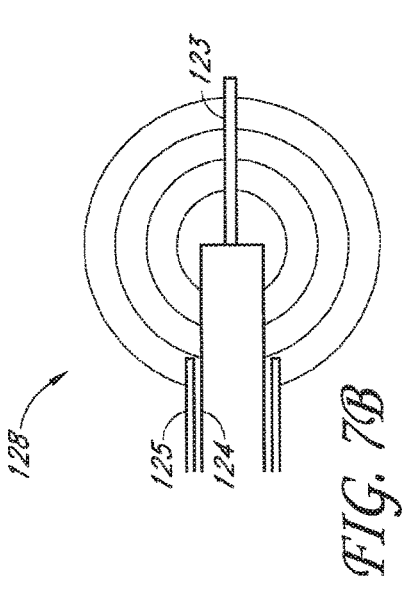
FIG. 7A shows a monopole antenna according to one embodiment.
Figure 7B:
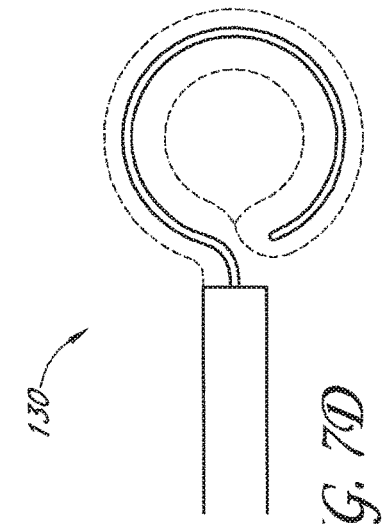
FIG. 7B shows a dipole antenna according to one embodiment.

The coaxial cable further comprises an inner conductor shaft and outer conductor. In configurations comprising a monopole antenna 122, as illustrated in FIG. 7A, an inner conductor element 123 extends from the inner conductor shaft 124 and beyond the outer conductor 125. Electromagnetic energy is radiated from the antenna 122 with an omnidirectional radiation pattern 126 around the circumference of the wire 125. In another embodiment shown in FIG. 7E, a conductive shield or sleeve 127 is added to the antenna 122 to choke off unwanted current flow down the outer conductor 125 of the coaxial line, thus limiting proximally radiating electromagnetic fields. In dipole antenna 128 configurations, as illustrated in FIG. 7B, the outer conductor 125 is exposed in such a manner that electric field lines stretch from the inner conductor element 123 to the outer conductor 125.

Figure 7C:
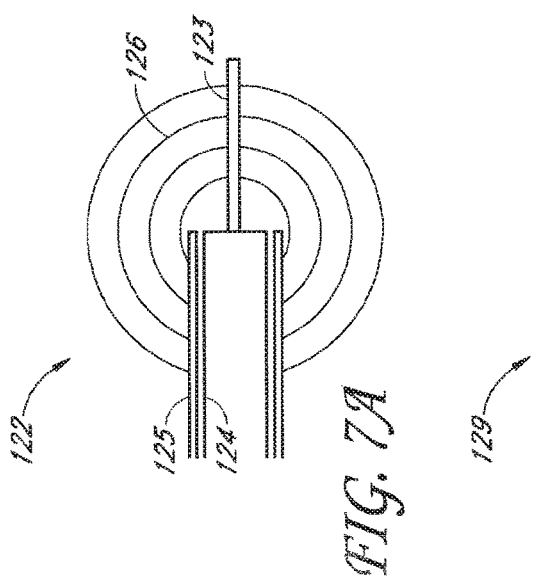
FIG. 7C shows a helical antenna according to one embodiment.
Figure 7D:
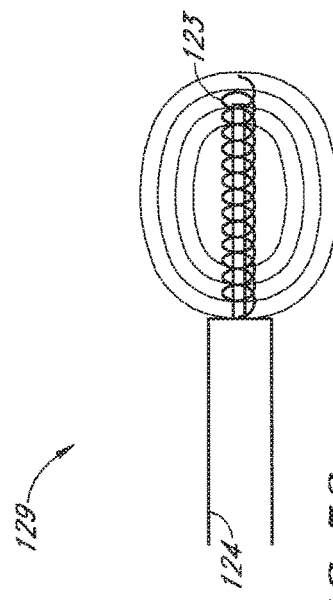
FIG. 7D shows a loop antenna according to one embodiment.
Figure 7E:
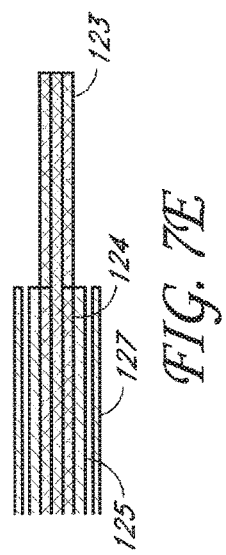
FIG. 7E shows an antenna having a shaped outer conductor according to one embodiment.
Figure 7F:
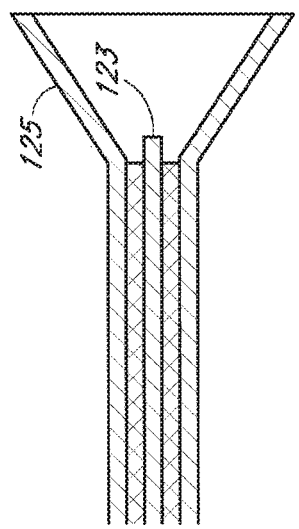
FIG. 7F-7G illustrate a horn antenna according to one embodiment.
Figure 7G:
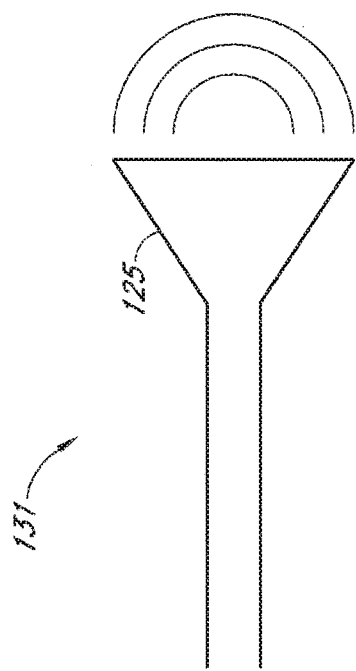

Depending on the performance desired of the antenna 120, the antenna may optionally comprise a helical antenna 129 shown in FIG. 7C, a loop antenna 130 shown in FIG. 7D, or a horn antenna 131 shown in FIGS. 7F-G. These alternative antenna configurations provide geometric radiating patterns. For example, as illustrated in FIG. 7E, the outer conductor 125 may comprise a shaped element, such as a horn shape, to provide a directional component to the field created between the inner conductor element 123 and outer conductor 125. Optionally, as shown in FIG. 7G, the outer conductor element 125 and/or inner conductor element 123 may be bordered by, coupled to or coated by a dielectric element to optimize the energy delivery capabilities of the antenna.

In another embodiment relating to energy delivery to target tissue, the applicator 312 comprises an antenna 132 connected to a coaxial cable 133 that is coupled to a microwave power source (not shown). As illustrated in FIG. 8A, the antenna 132 further comprises an inner conductor 123 disposed within the coaxial cable 133, wherein an inner conductor element 123 extends beyond the distal end of the coaxial cable 133 to form a coiled conductor element. Also shown are cooling inlets 134 and outlets 135 demarcated by arrows. The coiled conductor element provides a relatively flat structure which can be aligned with the skin surface to deliver an even amount of energy to a plane of target tissue. The applicator may optionally further comprise at its distal end a thin shield comprised of a polymer or ceramic. FIGS. 8B and 8C respectively illustrate additional embodiments 136, 137 of the coiled antenna configuration, wherein the coiled conductor element may comprise the entire coaxial cable 133 (FIG. 8B) or just the inner conductor 123 (FIG. 8C).

In addition to the antenna designs disclosed above, several other antenna designs may be employed in an apparatus for delivering microwave therapy. FIG. 9 depicts a cross-sectional view of one embodiment of slot antenna 138 comprised of coaxial cable 133 and shielding 139. The coaxial cable 133, which is connected to a microwave generator (not shown), is comprised of an inner conductor 123 and outer conductor 125, wherein the inner conductor 123 and outer conductor 125 are coupled together with solder 140 at the distal portion 141 of the antenna 138. The outer conductor 125 comprises a circumferential slot 142 through which the electromagnetic field of the antenna 138 radiates in an omnidirectional pattern. The shielding component 139 is used to direct the electromagnetic field toward the treatment area, thereby minimizing loss and maximizing efficiency, and to prevent stray radiation of electromagnetic fields. Since coaxial slot antennas 138 are fed in an unbalanced configuration, and are subject to proximal current flow down the outer conductor, a proximally radiated electromagnetic field can propagate longitudinally down the coaxial antenna, and may result in an undesirable treatment effect to the superficial non-target tissue 103, 104 that sits adjacent to the antenna. To avoid this outcome, the proximal portion 143 of the antenna 138 can be bent away from the treatment area such as at 144 such that the surface currents and accompanying fields are directed away from the non-target tissue 103, 104. Additionally, the electromagnetic field is prevented from migrating further along the coaxial cable and outside the antenna by electrically coupling the shielding to the coaxial cable using conductive epoxy or solder. These fields are retained within the housing of the antenna 138 so that they can be redirected via the shielding to the treatment area. The slot antenna system may also include a cooling circuit 118 and cooling plate 115 as shown.

Various other types of microwave antennas can also be used with the present application, for example, waveguide, single or multiple slot antennas, printed slot antennas, patch antennas, and Vivaldi antennas.

Microwave Generator

The microwave generator 113 preferably includes a generator head, a power supply, and an isolator. The generator 113 may be configured to have a frequency of between about 915 MHz to 15 GHz, more preferably between about 2.4 GHz to 9.2 GHz, such as about 2.45 GHz and 5.8 GHz, and have an output power maximum, in some embodiments, of no more than about 300 W, 200 W, 100 W, 75 W, or less.

Waveguide Antenna

In some embodiments, the system includes a waveguide antenna 145 (as shown, for example, in FIG. 20). The antenna preferably has a resonant frequency of between about 915 MHz to 15 GHz, more preferably between about 2.4 GHz to 9.2 GHz, such as about 2.45 GHz and 5.8 GHz in some embodiments.

The waveguide antenna 145 preferably has a cross-sectional size configured to the desired operational frequency and field configuration of the waveguide 145. Generally, lowest-order Transverse Electric (TE) modes are utilized (e.g., $TE_{10}$), although others are possible, such as Transverse Magnetic (TM), Transverse ElectroMagnetic (TEM), evanescent, or a hybrid mode. For example, the width and height (rectangular) or diameter (circular) waveguide geometry correlate with the operational frequency and field configuration of the waveguide 145. Additional parameters, such as the fill material, the type and placement of feed, and the use of mode filtering affect the operational frequency and field configuration of a waveguide 145. As will be appreciated by one of ordinary skill in the art, a transverse mode of a beam of electromagnetic radiation is a particular intensity pattern of radiation measured in a plane perpendicular (i.e., transverse) to the propagation direction of the beam. Transverse modes occur in microwaves confined to a waveguide 145.

Transverse modes occur because of boundary conditions imposed on the wave by the waveguide 145. The allowed modes can be found by solving Maxwell's equations for the boundary conditions of a given waveguide 145. Transverse modes are classified into different types. TE modes (Transverse Electric) have no electric field in the direction of propagation. TM modes (Transverse Magnetic) have no magnetic field in the direction of propagation. TEM modes (Transverse ElectroMagnetic) have no electric or magnetic field in the direction of propagation. Hybrid modes are those which have both electric and magnetic field components in the direction of propagation. An evanescent field is a time-varying field having an amplitude that decreases monotonically as a function of transverse radial distance from the waveguide 145, but without an accompanying phase shift. The evanescent field is coupled, i.e., bound, to an electromagnetic wave or mode propagating inside the waveguide 145.

The length of the waveguide 145 can be adjusted such that the physical length of the waveguide 145 corresponds to an electrical length that is a half-wavelength multiple of the guided wavelength 145 at the desired operational frequency. This allows an efficient match from the waveguide 145 feed into the load.

The waveguide 145 can have a wide variety of cross-sectional geometries depending on the desired clinical objective and geometry of the particular anatomical area to be treated. In some embodiments, the waveguide 145 has a rectangular, circular, elliptical, or hexagonal cross-sectional geometry.

In some embodiments, the coaxial feed can be placed between about 0 mm to a distance equal to the guided wavelength ($\lambda_g$) with an insertion depth of 1 mm to 100 mm. The placement is most preferably optimized for efficient transfer of power from coaxial feed to waveguide. In some embodiments, the coaxial feed has an insertion depth of between about 5% to 95% of the depth of the waveguide 145. In some embodiments, the coaxial feed has an insertion depth of at least about 80% of the depth of the waveguide 145.

To have the desired energy density in the region of target tissue 105, the antenna 120 can be within 0.5-5 mm of the skin (e.g., between about 1.5-2 mm, such as about 1.75 mm) in some embodiments, or within several wavelengths of the skin at a given operational frequency in other embodiments. This distance may be referred to herein as the antenna standoff height. Variation of the standoff height affects the spread of the microwave radiation. With a very large standoff, a reduced energy density over a larger volume is achieved. Conversely, with little to no standoff height the energy density is generally much higher over a smaller volume. To achieve therapeutic energy density levels with a large standoff, significantly increased input power levels are necessary. The absorption pattern of the microwave energy at depth in tissue, strongly influenced by the standoff, directly influences the relative safety margin between target 175 and non-target (deep) tissues 104. Finally, standoff height causes large variation in the loading conditions for the waveguide, with reflected power levels observed by the waveguide antenna 145 changing with standoff changes. In some embodiments, if a coded waveguide 145 is used, the standoff height could be about zero or even negative (e.g., the skin could be within the waveguide 145).

Dielectric Filler

Choice of dielectric filler material allows waveguides 145 of various cross-sectional area to be utilized and propagated at a specific desired frequency. Cutoff frequency of a fixed size waveguide can be decreased by utilizing larger dielectric constant materials. For a desired treatment size and specified frequency range of 2.4-9.2 GHz, dielectric filler materials with a dielectric constant of K=2 to 30 are utilized. In some embodiments, a preferred dielectric constant is K=10.

Larger K value dielectric filler materials have a permittivity that is closer to that of tissue, giving the potential for lower reflection in general between the applicator/tissue interface. Some examples of dielectric constants include the skin (K=35-40), fat (K=5-10), muscle (K=50), or water (K=80). In embodiments involving a cooling element 115 or other barrier, the dielectric filler material may be selected based on having a dielectric constant that matches well to the cooling element 115 and skin.

Tuning Stub

In some embodiments, a microwave antenna system, e.g., a waveguide system, includes a metal, adjustable tuning stub that can be utilized for optimal power transfer into a given tissue to further minimize reflections for a given tissue load at a specific frequency. This enhancement can help account for variations in manufacturing and tolerance. Instead of having high tolerance requirements, which might be cost prohibitive, each antenna can be tuned to achieve desired functional characteristics. In some embodiments, the metal tuning stub can be secured to a wall of the antenna (e.g., the waveguide 145) by a suitable means such as adhesion, a rivet, soldering, or the like. The stub can be a cylindrical member depending from the top wall transversely to the waveguide 145 path and located substantially on the longitudinal centerline of the waveguide. The stub can extend to various depths in the waveguide 145 and is sized and located accurately so as to optimally match the impedance that the waveguide antenna 145 presents to the generator 113, allowing efficient power transfer. The tuning stub advantageously provides a reactive impedance substantially without a resistance component.

Array of Waveguides

Waveguide applicators can be placed in an array configuration for simultaneous or sequential treatment of multiple sites. Additionally, the possibility exists for beneficial phased (constructive effect of in-phase fields) operation of a waveguide array (similar to the twin coaxial slot antennas), as discussed elsewhere in the application.

Horn Antenna

In some embodiments, the aperture of the waveguide antenna can be flared outward in a distal direction to form a horn antenna configuration. This can spread the energy dispersion more widely, as well as increase the robustness of the antenna to varying tissue loads (i.e., the antenna will match well with patient to patient variation in tissue composition). The wider footprint created by a flared antenna provides the potential for an increased treatment size. The flare can also advantageously increase the manufacturing tolerance for the waveguide. For example, a horn antenna with a desired frequency of 5.8 GHz may have a frequency range of about 5.5 to 6 GHz in some embodiments.

Enhancements

Protective Cooling

In thermal treatments of tissue, it may be beneficial to protect against the unnecessary and potentially deleterious thermal destruction of non-target tissue. This is particularly the case in sub-dermal treatments since excess energy delivered to the epidermal 102 and dermal 101 layers of the skin can result in pain, discomfort, drying, charring and edge effects. Moreover, drying, charring and edge effects to surrounding tissue can impair a treatment's efficacy in some cases as the impedance of desiccated tissue may be too high to allow energy to travel into deeper regions of tissue.

Figure 10A:
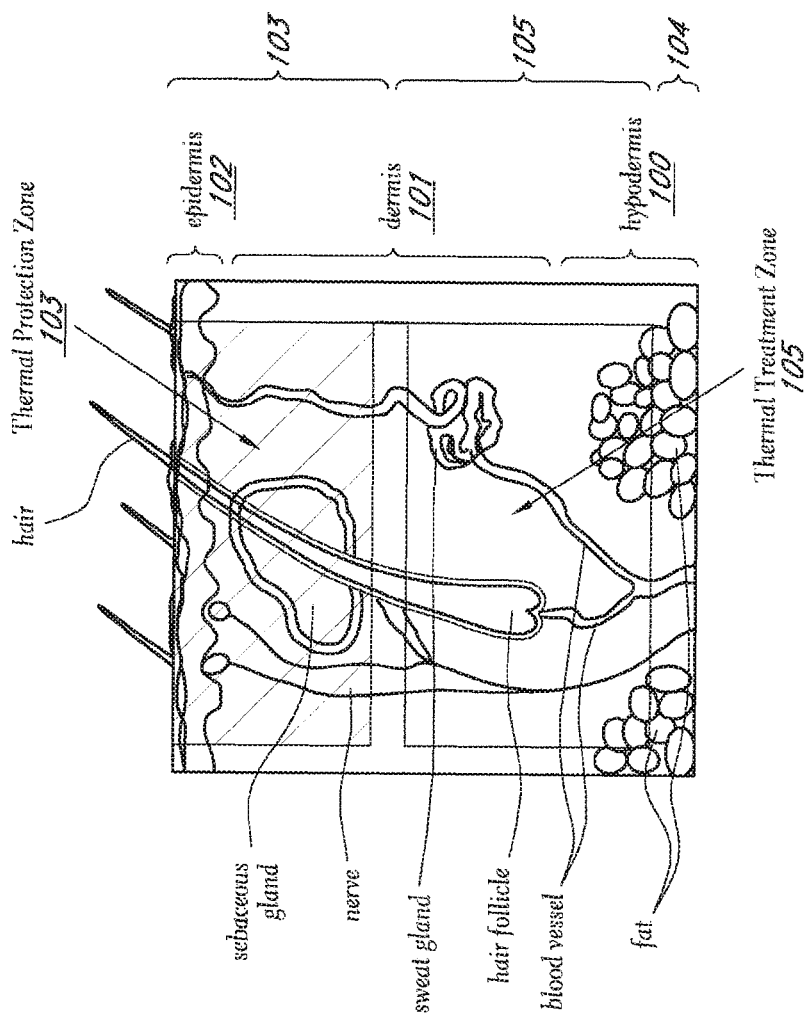
FIG. 10A shows a cross-sectional view of a target tissue having a zone of thermal treatment according to one embodiment.

To avoid thermal destruction to non-target tissue and any complications associated therewith, an energy delivery device can include a cooling element 115 for providing a cooling effect to the superficial non-target tissue 103 (e.g., the epidermis 102 and portions of the dermis 101). By conductively and/or convectively cooling the epidermis 102 and allowing the cooling effect to penetrate into the dermis 102, the cooling element 115 will establish a zone of thermal protection 103 for the superficial non-target tissue as illustrated in FIG. 10A. With the cooling element 115 providing this zone of protection 103, the target tissue 105 (e.g., zone of thermal treatment 105 in FIG. 10A) can be treated with minimal risk of thermal damage to non-target tissues 103, 104.

Figure 10B:
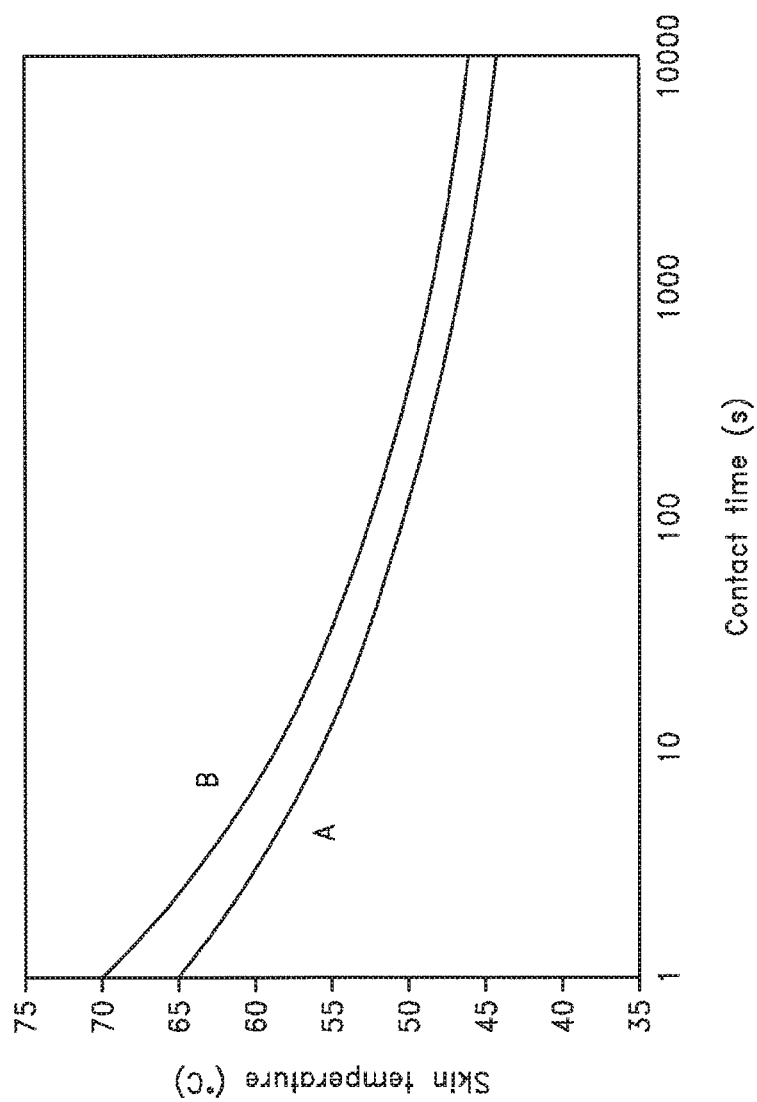
FIG. 10B shows a time-temperature curve illustrating the temperature at which a skin undergoing treatment would be expected to burn.

FIG. 10B above illustrates a time-temperature curve illustrating the skin temperature above which a burn would be expected (curve B) and below which no appreciable injury would occur (curve A). Therefore, it would be very desirable that during energy treatment the cooling system maintain the non-target skin surface temperature (which can be measured by the temperature sensing element as discussed elsewhere in the application) below curve B for a given treatment duration, as well as below curve A in some embodiments.

To further reduce the risk of pain and/or other uncomfortable sensations associated with thermal treatment, the cooling element 115 can further cool the superficial non-target tissue 103 to create a numbing effect. Depending on the type of thermal treatment employed and the associated need for complementary cooling, the cooling treatment and resulting cooling and/or numbing effect may be applied before, during and/or after the thermal treatment. Protective cooling may also be applied in an alternating fashion with the heating treatment to maximize energy delivery while minimizing adverse effects to non-target tissue 103, 104.

The cooling element 115 can take many forms. The cooling element 115 can be a passive heat sink that conductively cools the skin, such as a layer of static, chilled liquid (e.g., water, saline) or a solid coolant (e.g., ice, ceramic plate), a phase change liquid selected which turns into a gas, or some combination thereof (e.g., a cylinder filled with chilled water). The cooling element 115 can also provide active cooling in the form of a spray or stream of gas or liquid, or aerosol particles for convective cooling of the epidermis 102. A thermo-electric cooler (TEC) or Peltier element can also be an effective active cooling element 115. Alternatively, an active cooling element 115 can comprise a thermally conductive element with an adjacent circulating fluid to carry away heat.

The cooling element 115 can also be incorporated into the device as an internal cooling component for conductively cooling non-target tissue 103, 104. For example, an energy delivery device can couple a cooling component 115 to the energy applicator, where the cooling component 115 can actively or passively provide conductive cooling to adjacent tissue. When passive cooling is provided, the cooling component 115 may comprise a cold metal plate or block. When active cooling is provided, the cooling component 115 may comprise a thermally conductive element, wherein a chilled liquid (e.g., water, dry ice, alcohol, anti-freeze) is circulated through the element's internal structure. For example, in microwave energy delivery devices that include a dielectric, the dielectric itself can be a cooling component. In another example, the cooling component 115 can be incorporated into the antenna 120 such that it is adjacent to the dielectric.

Figure 11A:
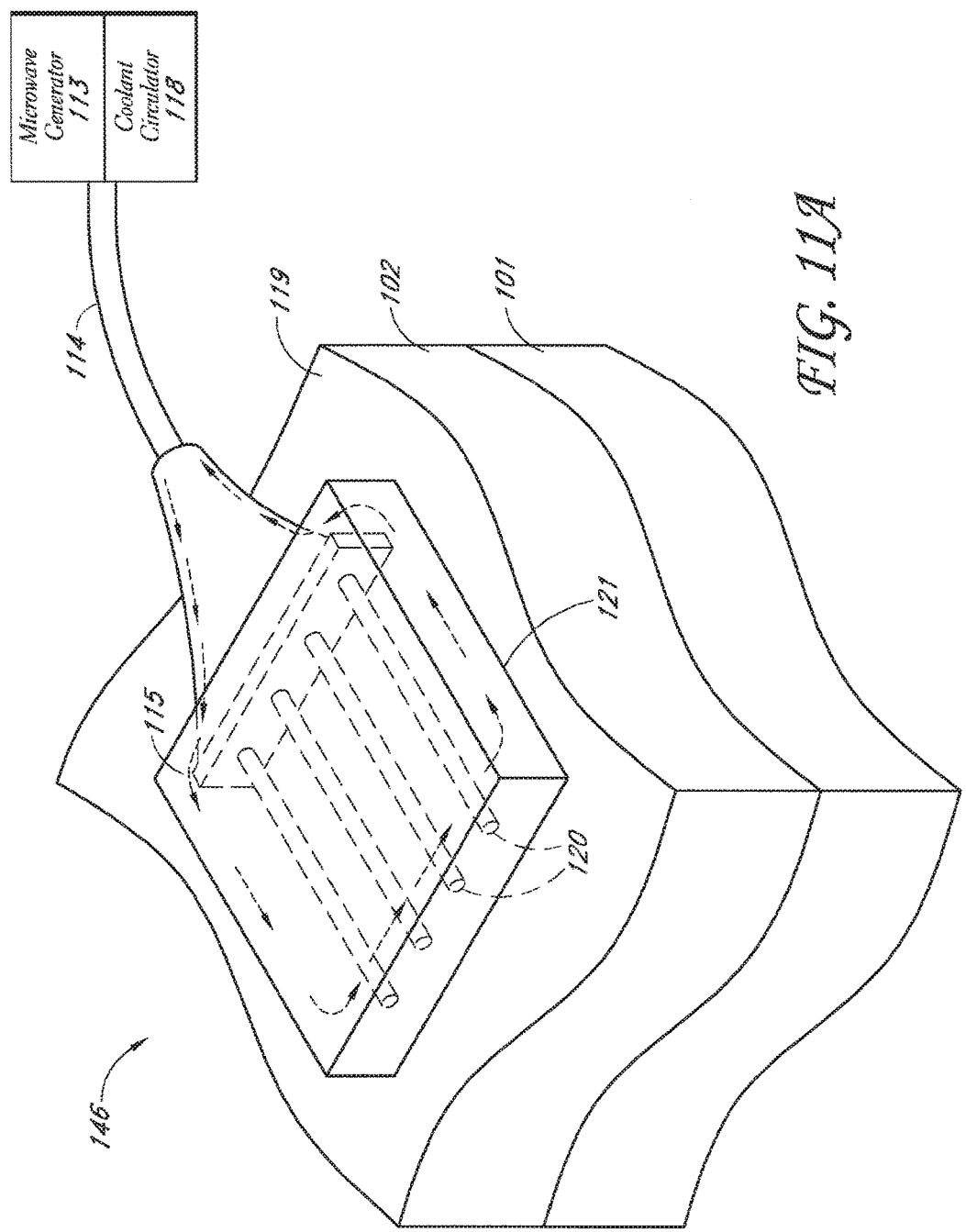
FIG. 11A shows an isometric view of a non-invasive energy delivery device comprising multiple microwave antennas electrically connected to a microwave generator according to one embodiment.
Figure 11B:
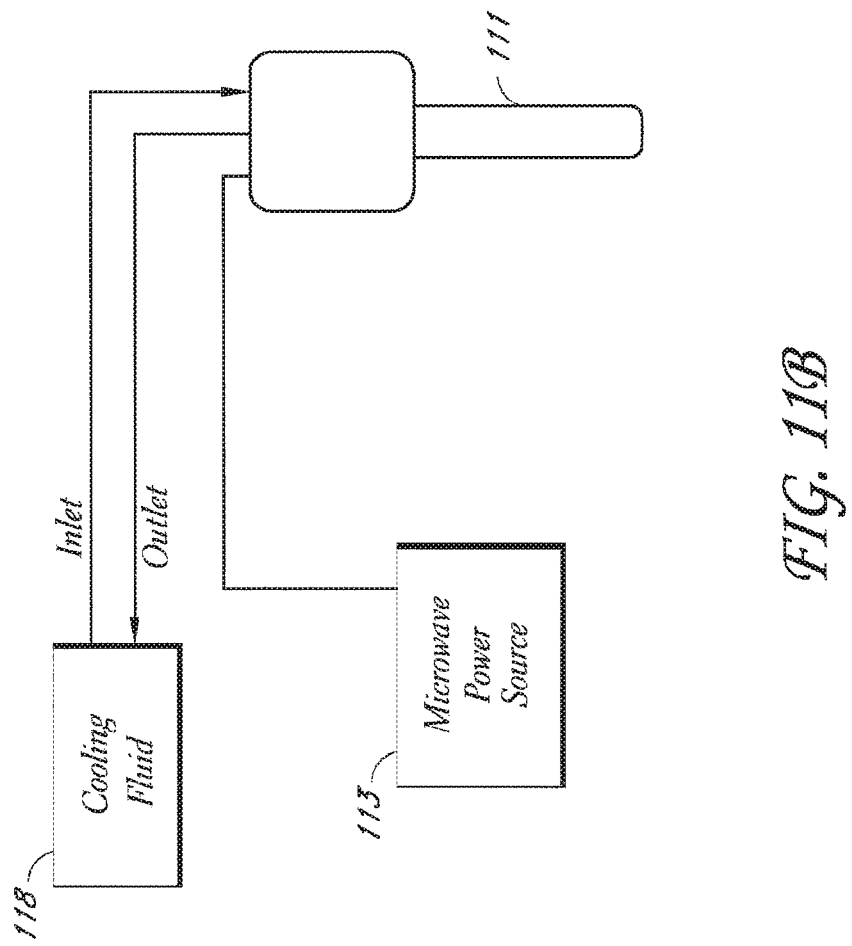
FIG. 11B shows a schematic view of a cooling source located remotely from an energy source and energy applicator according to one embodiment.

As shown in FIG. 11A, a cooling component 115 can be incorporated into an energy delivery device 146 comprising at least one microwave antenna 120, such as described above. In this embodiment, fluid is used to cool adjacent skin tissue 119. This convective cooling can be enhanced by a coolant circulator 118 that could optionally be integrated within, coupled to or located remotely from the energy generator 113. As shown in FIG. 11B, the cooling circulator 118 is located remote from both the energy source 113 and energy applicator 121. The properties and characteristics (e.g., medium, flow rate, temperature) of the circulating fluid (gas or liquid) can be selected and modified to achieve the desired cooling effect in light of the amount and rate of energy delivered to the target tissue.

Any type of chilled fluid or refrigerant may be used. In some embodiments, a system optimized for the delivery of microwave energy may avoid having ions in the coolant. Coolant with high ionic content generally has a high conductivity, leading to microwave absorption and heating, disrupting the microwave field and altering the energy delivery to the tissue. Some examples of low-loss coolant include deionized water and/or one or more of the following: vegetable oil, such as peanut, canola, sunflower, safflower, or olive oil, distilled water and alcohol, or isopropyl alcohol. In one embodiment, the coolant used is isopropyl alcohol, which advantageously allows for liquid cooling at lower temperatures because the freezing point of isopropyl alcohol is lower than that of water. While liquid coolants have been described, gas and solid coolants are also within the scope of the invention.

A cooling plate, in some embodiments, preferably includes one or more of the following functions: (1) it is thermally conductive, that is, it controls heat transfer rate between tissue and cooling fluid; (2) it is thin (e.g., less than about 1 mm, 0.75 mm, 0.5 mm, 0.25 mm, 0.20 mm or less in some embodiments) relative to the wavelength of the microwave signal and has low electrical conductivity (e.g., sigma of less than about 0.5, such as less than about 0.01 in some embodiments) in order to maximize the efficiency of power transfer into the tissue/thermal conductivity, to keep the waveguide 145 close to the skin and minimize standoff height; (3) it is of adequate stiffness to eliminate bowing while conforming to the skin, thereby maintaining consistent cooling (via constant contact with skin and uniform flow geometries (4) it is made of materials that are transparent to microwave energy (e.g., non-reflective). A cooling plate may be made of any suitable material, for example, glass or a ceramic composite including about 96% alumina, or a pyrolytic carbon in some embodiments.

Low-loss cooling plate materials that meet permittivity range are desirable. They can be solids or non-solids (e.g., water, oil). In some embodiments, ceramics such as alumina (K=10), zirconia, silica, aluminum silicate, or magnesia may be used. In other embodiments, polymers, such as silicone rubber (K=3), or a ceramic-polymer composite such as eccostock polymer can be utilized. Although specific materials have been described, one skilled in the art will appreciate that the application is not limited to those materials listed.

In some embodiments, the cooling plate is preferably sufficiently thin to minimize undesirable microwave reflection. For example, in some embodiments, the cooling plate may be no more than about 10 mm, 9 mm, 8 mm, 7 mm, 6 mm, 5 mm, 4 mm, 3 mm, 2 mm, 1 mm, 0.75 mm, 0.5 mm, or less in thickness.

The interface between waveguide 145 (outer wall) and filling, in some embodiments, has minimal air gaps, such as less than about 3 mm, 2 mm, 1.5 mm, 1 mm, 0.5 mm, or less to help avoid unwanted e-fields. Interface between the waveguide cooling element 115 and less housing or cooling chamber should have no air gaps.

Flow Manifold

In some embodiments, the flow chamber of a cooling system includes inlet and outlet reservoirs to achieve a consistent flow rate across the flow chamber. Reservoirs are located on either side of the flow chamber. The inlet reservoir allows for the accumulation of coolant such that the fluid can flow through the cooling chamber at nearly the same rate at any point in the cooling chamber. This constant flow rate allows for consistent cooling across the cooling plate, to provide a thermally conductive barrier. The reservoir at the outlet helps to advantageously prevent fluid backup that would inhibit flow across the flow chamber.

The cooling circuit also preferably includes a temperature control element to cool or heat fluid to the desired temperature, and a pump. The pump may be a conventional pump within the circuit, or alternatively a pump that functions outside of the cooling circuit, such as a roller pump.

The flow rate of the cooling fluid may be adjusted for any desired cooling. In some embodiments, the flow rate can be between about 100 and 1,500 ml/min, such as between about 200-600 ml/min, between about 200-400 mL/min, or about 600 mL/min in certain embodiments. The temperature of the cooling fluid across the cooling plate is preferably between about −5° C.-40° C., such as between 10° C.-37° C., or about 10° C. or 22° C. in certain embodiments. The geometry and surface area of the cooling plate is preferably proportional with respect to the surface area and geometry of the body surface to be treated.

Geometries

In many of the embodiments disclosed herein, treatment is administered topically and/or in a minimally-invasive fashion to achieve the desired treatment effect on target tissue. In some of these embodiments, the skin is depicted as a flat, multilayer plane of tissue, wherein treatment can be administered to target tissue in a manner that is substantially perpendicular to its planar surface. It should be understood that although a treatment may be disclosed with respect to a particular skin geometry (e.g., perpendicular topical delivery, perpendicular percutaneous insertion, etc.), such treatment may be administered with respect to any number or variety of geometries, including those discussed below.

Tissue Acquisition/Elevated Skin

In energy treatments involving the delivery of microwaves, for example, there is the risk that the delivered energy may penetrate too deeply into the body and cause harm to the deep non-target tissue 104, associated critical structures (e.g., blood vessels, lymph nodes, muscle tissue, etc.) and body organs. Therefore, it may be beneficial to elevate the target tissue comprising portion of the skin from the underlying tissue. Such elevation can be achieved through manual manipulation by the clinician or facilitated using any number of devices. For example, as illustrated in FIG. 12, a vacuum 147 can be used to pull and hold the skin 119, thereby elevating it for treatment. Optionally, a vacuum-suction device 147 can be incorporated into an energy delivery device such that suction and energy delivery can be applied in unison.

In another embodiment, a tool utilizing a sterile adhesive can effectively prop up the skin for treatment. More simply, however, a clinician can use any number of clamps, tongs or other devices to achieve and maintain skin elevation for and during treatment.

Folded Skin

In another skin geometry configuration, it may be beneficial to first pinch and fold the patient's skin prior to delivering energy to the target tissue. Following the optional administration of a local anesthetic such as lidocaine (topically or subdermally), the patient's skin can be grasped and pulled partially away such that the epidermis 102, dermis 101 and subcutaneous layer 100 are separated from the underlying skeletal muscle. Once separated, the skin could then be folded such that neighboring sections of the skin abut one another wherein the subcutaneous layer 100 of one side of the fold faces the subcutaneous layer 100 of the other side of the fold. Isolating these adjacent subcutaneous layers 100 results in a treatment zone that is dense with target tissue 152 and target 152 structures. FIG. 13 shows an example of a skin fold 148. The skin fold 148 comprises a top 149, two sides 150 (only one shown), two edges 151 (only one shown) and a zone of "sandwiched" target tissue 152 along the longitudinal length of the fold (e.g., treatment zone).

Focusing treatment on the target tissue 152 rich region within the skin fold 133 will allow for a more efficient procedure as two adjacent layers of target tissue can be treated in a single treatment. Additionally, treatment can be administered from one or more orientations (e.g., both sides of the fold), which can result in a more effective and reliable treatment. Also, since the skin is being pulled away from the body, damage to non-target structures 155 is minimized. Moreover, since the act of pinching or suctioning the skin fold 148 into position temporarily restricts blood flow to the folded tissue, there is less chance that the thermal energy delivered during treatment will be dissipated by blood flow. Additionally, the neural activity caused in the skin by the folded configuration may reduce the patient's pain sensation during treatment under the gate control theory of pain management (discussed below), which can be applicable for both vacuum lifting of the skin as well as manual "pinching" of the skin.

In one embodiment, as illustrated in FIG. 14, the skin fold 148 is treated from opposite sides by an energy delivery device comprising two energy delivery elements 154. The energy delivery elements 154 are configured to deliver energy to the treatment zone 148 in the middle of the fold. In the case of energy delivery devices that comprise one or more microwave antennas 120 connected to one or more microwave generators 113, for example, as shown in FIG. 5 above, the microwave energy 112 can cross the outer epidermal layers 102 from each side of the skin fold and penetrate deep into the treatment zone 152. To optimize the delivery of microwave energy 112 to previously target tissue 105, a dielectric can optionally be used in this treatment. Also as shown previously and described in connection with FIG. 5, cooling elements 115 can also be used on the skin surface to create a zone of protection 155 for non-target tissue. Additionally, the device 153 can be configured with a cooling element 115 and/or dielectric element on either side of the skin fold 148 to stabilize the fold during treatment.

Figure 15:
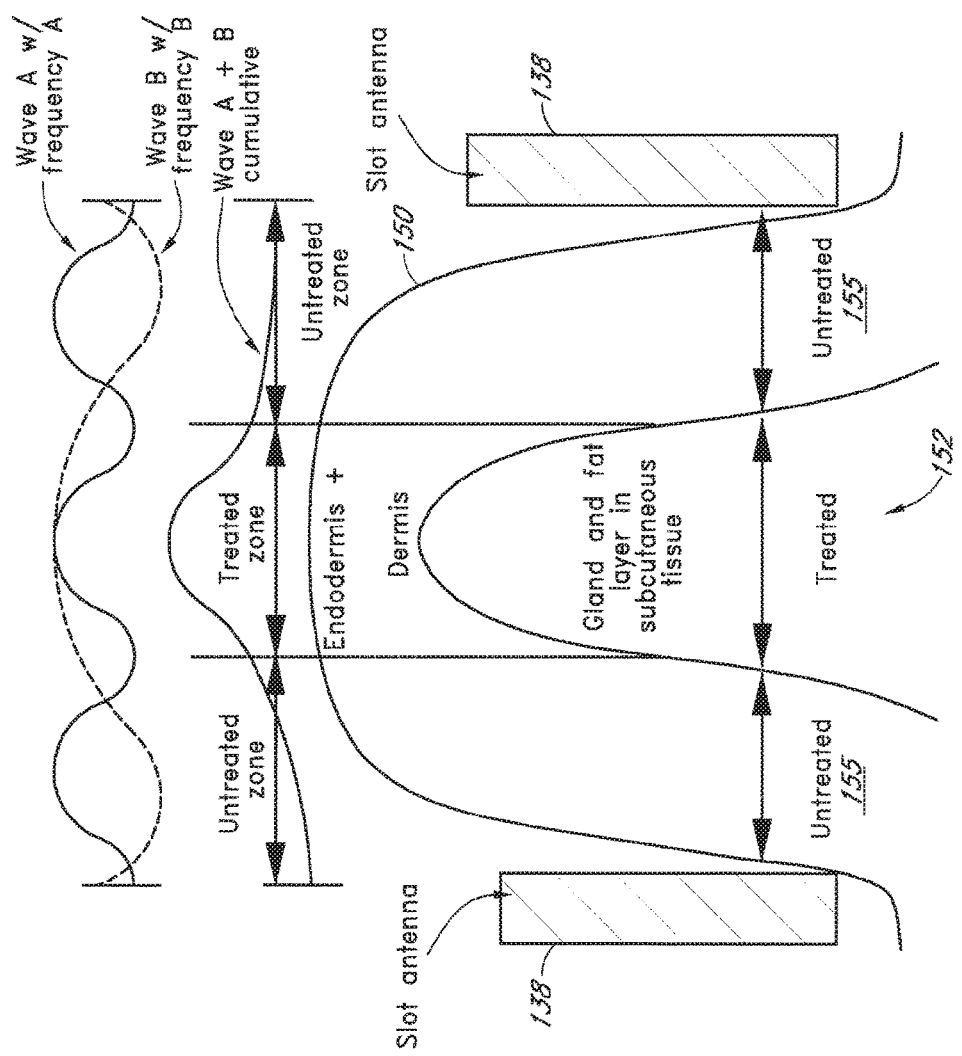
FIG. 15 shows a skin fold being treated by two slot antennas positioned on two sides of the skin fold according to one embodiment.

In another embodiment, treatment can be concentrated and localized at the target tissue 152 using the summation effect of two or more energy signals. As illustrated in FIG. 15, antennas such as the slot antennas 138 shown, can be positioned on either side (such as 139) of the skin fold 133 to deliver continuous microwave treatment from both sides of the skin fold. The energy waves from each antenna 138 can be phased such that the wave from a first antenna 138 can harmonize with the wave from a second antenna 138 and yield a cumulative treatment effect at the zone of target tissue 152. The waves can also be synchronized such that they cancel one another out in areas where treatment is not desired (i.e., non-target tissue). Accordingly, the optimal treatment would comprise antennas 138 configured and coordinated to deliver energy waves that are additive at the target tissue dense region but subtractive at other regions.

As mentioned with respect to many of the embodiments discussed above, it may be desirable to create the skin fold with the assistance of suction. For example, a suction-vacuum 147 cavity can be incorporated into any of the aforementioned devices. FIGS. 16A-B show perspective views of one embodiment of a suction system 147 comprising a housing 156, a suction chamber 157, a vacuum port (not shown) for connection to a vacuum source (not shown) and twin slot microwave antennas 138 operably connected to a power source via coaxial cables 133. Also shown are cooling flow inlet 134 and outlet 135 ports for each antenna 138. The vacuum source can be configured for providing sufficient vacuum force to grasp and hold the skin in a folded orientation within the tissue chamber 157. The device may utilize the suction 147 for simply grasping the skin at the beginning of the procedure or holding the skin in place for some or all of the treatment. This area of lower pressure or suction within the device will help adhere the device to the skin so as to bring the target tissue into closer apposition to the antenna 138 and reduce blood flow in the target tissue, thereby enabling more efficient heating of the tissue.

The use of suction has a number of additional benefits. For example, suction can be useful in orienting the skin in the desired geometry. As shown in the treatment configurations disclosed above, suction can help grasp and retain the skin in either the folded skin or elevated configurations. Also, by using suction to bring the skin in position for treatment, treatment variability can be minimized. Clinicians will not have to worry about maintaining consistent contact force since that will be regulated by the suction.

Furthermore, suctioning may allow for advantageous temporary occlusion of blood vessels superficial to or in the same plane as the target tissue, in embodiments where blood vessels are not preferentially targeted. By restricting flow through the vessels, the water content of the vessels would thus be decreased and prevent undesirable coagulation via microwave energy. This can also provide a heat-sink effect as microwave energy would be more efficiently directed to the target tissue rather than be directed to the non-target blood vessels.

However, in some embodiments it may be desirable to employ suction such that blood remains in the vessel such that the vessel preferentially absorbs microwave energy, such as, for example, to treat telangiectasias or varicose veins.

Additionally, suction may help to control pain by triggering stretch and pressure receptors in the skin, thereby blocking pain signals via the gate control theory of pain management. The gate control theory holds that an overabundance of nerve signals arriving at the dorsal root ganglion of the spinal cord will overwhelm the system, and mask or block the transmission of pain receptor signals to the brain. This mechanism of pain management is exploited by implantable electrical pain control units, TENS systems, the Optilase system and others.

In some embodiments, a suction system 147 includes a vacuum pump configured with sufficient pressure for the area of tissue acquisition desired. The pressure can be between about 450-700 mm Hg, and about 650 mm Hg in some embodiments. The geometry of the area covered by the chamber can be ovoid in some embodiments, or any other desired shape. In an embodiment with a 15 cm×25 cm rectangular waveguide 145 and cooling plate 115, the suction chamber 157 may have a 15 cm×25 cm central rectangular area with two lateral 7.5 cm radius arc regions. In some embodiments, the chamber depth is less than about 30 mm, 25 mm, 20 mm, 15 mm, 10 mm, 7.5 mm, 5 mm, or less. The chamber walls may, in some embodiments, be angled out from the base of the chamber 157, e.g., between about 5-30 degrees, such as about 20 degrees.

The depth of the suction chamber 157 controls the amount that the skin is elevated when acquired and treated, which, in turn, impacts the lesion formed within the skin tissue. When treated in its compressed and elevated state, a subdermal lesion is created in the compressed tissue. When the suction 147 is released and the skin is disengaged from the chamber 157 and its compressed state, the lesion is stretched out. The result is a thinner and wider subdermal lesion.

The suction system 147 also can include one or more suction ports, e.g., two ports, each connected via a suction channel to a suction zone. The suction zone defines a pattern to maximize suction area, which in turn maximizes suction force. The suction area also prevents tissue distortion. In embodiments, with a plurality of suction ports, the ports may be connected by a suction conduit that can split into distal branches to mate with each suction port.

The system 147 may also include a control element, such as a CPU, to control various parameters as noted above. In some embodiments, the preferred treatment sequence is (1) suction to acquire the desired tissue; (2) pre-cool the desired tissue; (3) deliver energy to the tissue; (4) post-cool the tissue; and (5) release the suction. Other tissue acquisition systems, devices, and methods that can be used with embodiments described herein are disclosed, for example, at pp. 69-71 of U.S. Provisional Application No. 61/045,937, previously incorporated by reference in its entirety.

The following Table 1 is a non-limiting listing of various parameters that can be altered to control the thickness of the lesion created by the delivered energy, as well as the depth of the protection zone created by the cooling system. Ranges listed are for certain embodiments only; other ranges or values outside the listed ranges are also within the scope of the invention.

TABLE 1

Effect of Varying Certain Parameters

| Parameter | Protection Zone Depth | Lesion Size | Range |
|---|---|---|---|
| ↑ Power | Decrease | Increase | 20-100 W, 40-70 W |
| ↑ Frequency | Decrease | Decrease | 2.4 GHz-9.2 GHz, 2.45 GHz, 5.8 GHz |
| ↑ Coolant Temp (hotter) | Decrease | Increase | −5 C.-40 C., 10-25 C., 10 C., 22 C. |
| ↑ Coolant flow rate | Increase | Decrease | 100-1500 ml/min, 300-600 ml/min, 600 mL/min |
| ↑ Depth of suction chamber | Decrease | Decrease | 1-20 mm, 7.5 mm |

TABLE 1-continued

Effect of Varying Certain Parameters

| Parameter | Protection Zone Depth | Lesion Size | Range |
|---|---|---|---|
| ↑ Duration of Energy delivery | Decrease | Increase | 0.1 sec-60 secs; 2-5 secs |
| ↑ Duration of pre-cooling | Increase | Decrease | 0-60 s, 0-5 s |
| ↑ Duration of post-cooling | Increase | Decrease | 0-60 s, 0-20 s |

In some embodiments, the system also includes one or more temperature sensors. The sensors may be a thermocouple (TC), a thermistor, or a fiber optic sensor (which advantageously will not interact with microwave energy if lacking metal). In some embodiments, the temperature sensor is a thermocouple sensor located at the interface between the skin surface and the cooling plate. Some embodiments may also optionally include a thermocouple sensor to measure the temperature of the coolant inflow and/or outflow reservoirs. The system may also include a feedback loop configured to adjust the energy delivered and/or coolant temperature, or alternatively shut off the system, for example, if a preset maximum skin or coolant temperature is identified. Other sensors such as pressure or distance sensors can be present to confirm skin contact and engagement.

Medications

In many of the treatments disclosed herein, the target tissue 105 is damaged to yield a treatment effect. However, non-target tissue 103, 104 may also be affected in some of these treatments. Such treatments may have complications such as pain, inflammation, infection, and scarring, which may occur both during and after treatment. Therefore, it may be beneficial to provide the patient with medications prior to, during and/or after the treatment to minimize the incidence and impact of these complications. The medications, which could be anesthetics for pain, such as lidocaine, ropivacaine, bupivacaine, tetracaine, and procaine; steroids or nonsteroidal agents for inflammation and antibiotics for infection, can be administered orally, topically, intravenously, or via local injection.

Controlled Delivery of Energy

With some of the treatments disclosed herein for delivering energy to target tissue 105, controlled delivery of energy may be helpful in avoiding unnecessary damage to target tissue 105 (e.g., desiccation, charring, etc.) and non-target tissue 103, 104 as a result of overheating. A controlled delivery of energy may also result in a more consistent, predictable and efficient overall treatment. Accordingly, it may be beneficial to incorporate into the energy delivery system a controller having programmed instructions for delivering energy to tissue. Additionally, these programmed instructions may comprise an algorithm for automating the controlled delivery of energy.

In an embodiment employing the controlled delivery of energy, the aforementioned controller can be incorporated into or coupled to a power generator, wherein the controller commands the power generator in accordance with a preset algorithm comprising temperature and/or power profiles. These profiles may define parameters that can be used in order to achieve the desired treatment effect in the target tissue. These parameters may include, but are not limited to, power and time increments, maximum allowable temperature, and ramp rate (i.e., the rate of temperature/power increase). Feedback signals comprising real-time or delayed physiological and diagnostic measurements can be used to modulate these parameters and the overall delivery of energy. Among the measurements that can be taken, temperature, impedance and/or reflected power at the treatment site and/or target tissue 105 can be particularly useful. These measurements may help monitor the effect that the energy delivery has at the treatment site and at the target tissue over the course of the treatment. The energy controller may have fixed coefficients or the controller coefficients may be varied depending upon the sensed tissue response to energy delivery. Additionally, an algorithm comprising a safety profile may be employed to limit energy delivery or to limit sensed tissue temperature. These algorithms could shut off energy delivery or modulate the energy delivery. Additionally, in treatments where thermal protection is employed, such as an active cooling element 115, the protective cooling can be modulated based on the monitored data.

By considering temperature measurements in the delivery of energy, treatment can be administered to achieve the necessary treatment effect while avoiding unnecessary complications of the treatment. For example, energy delivery to target tissue 105 can be steadily increased (i.e., ramped up) until the desired threshold temperature is reached for the target tissue, wherein the threshold temperature is that which is necessary to yield a treatment effect. By ceasing the power increase, or the delivery of energy altogether, once the threshold temperature is reached, harm to non-target tissue 103,104 resulting from additional and excessive heating can be avoided. In some embodiments, the temperature of the target tissue can be indirectly and noninvasively monitored by determining the temperature of a superficial non-target tissue 103, e.g., at the surface of the skin, and extrapolating from that temperature measurement the target tissue temperature. Adjustments can be made for the skin thickness of a particular patient. In some embodiments, it is desirable to maintain the superficial non-target tissue 103 temperature at less than about 45° C.

Temperature can be measured using any number of sensors, including thermocouples and thermistors, wherein such sensors can be incorporated into the energy delivery element 154, the energy delivery device and/or the energy delivery system. For example, a thermocouple can be imbedded in the energy applicator, positioned adjacent to the antenna as part of the energy delivery device or located separate from the device such that the thermocouple is wired directly to the generator. The temperature measured can be that of the tissue immediately adjacent the device, the target tissue or any other tissue that may provide useful temperature measurements. In cases where the energy delivery element is in thermal communication with the surrounding tissue (e.g., via conduction), a sensor that is incorporated into the energy delivery element may measure the temperature of the element itself.

Impedance can be measured by observing a tissue's response to electrical stimulation. This measurement is useful because it can help assess the extent of energy delivery to and through tissue. For example, energy that is directed to tissue having high impedance may have difficulty infiltrating deeper regions of tissue. This is particularly important in the case of skin tissue, as the impedance of skin can change over the course of treatment. As tissue is heated, it loses moisture and its conductivity drops and impedance increases. If the tissue is heated until it is desiccated, the resistivity of the tissue may impair energy delivery to surrounding tissue via electrical conduction. Employing impedance measurement feedback in the energy delivery system can optimize the delivery of energy to target tissue 105 while avoiding adverse consequences to both the target 105 and non-target tissue 103, 104.

Staged Treatment

Figure 17:
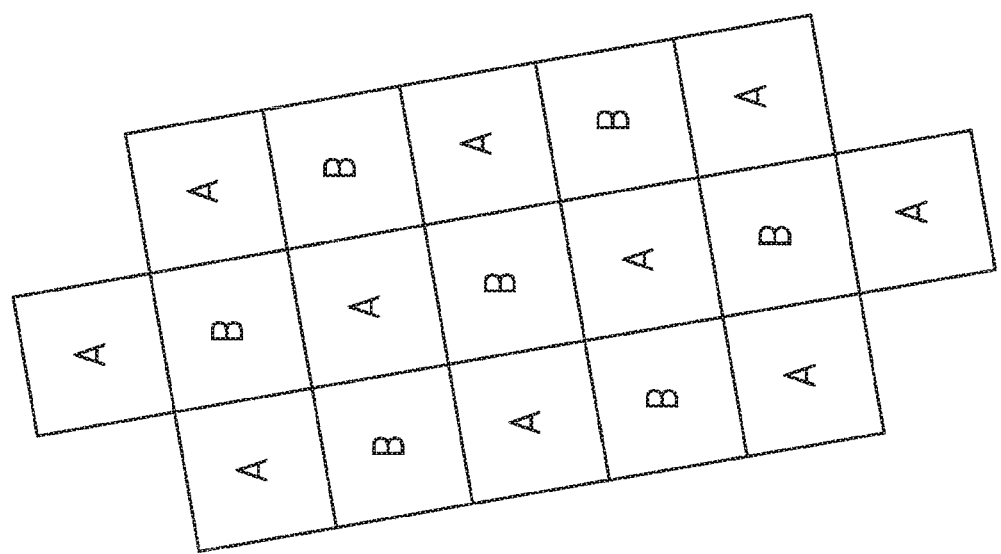
FIG. 17 shows one embodiment of a representative grid indicating target treatment sites "A" and target treatment sites "B" that could be used over a skin area to identify specific areas of treatment.

In many of the treatments disclosed in this specification, it may be desirable to perform the treatment in stages. Additionally, the treatment can be patterned such that sections of target tissue 105 are treated in the initial stage while other sections are treated in subsequent stages. For example, as illustrated in FIG. 17, a patient could have the regions marked "A" treated in a first stage and the regions marked "B" treated in a second stage. Additionally, the treatment could be broken down into further stages such as at least 3, 4, 5, 6, or more stages and additional regions. Optionally, treatment could be administered to the same regions in multiple stages such that each region receives treatment multiple times. In one embodiment, in subsequent stages the treatment to a particular region may vary, such as with an increased or decreased amount of energy, or with a different treatment type.

This approach has numerous potential benefits. First, a staged treatment gives the body the opportunity to heal between treatments. This is particularly important since treating or thermally damaging discrete regions of tissue over several sessions may have fewer and less severe complications compared to treating or thermally damaging a relatively large area of tissue in one session. Secondly, a patterned treatment having small regions of treatment may elicit a more favorable healing response. Since healing time is related to the distance that fibroblasts must migrate from surrounding tissue, smaller treatment areas may heal much faster than larger treatment areas. FIGS. 18A-E illustrate examples of various patterned treatments.

For the medical practitioner, a staged and patterned treatment may provide the opportunity to track the treatment's efficacy and provide follow-up treatments tailored to the patient's specific needs. For example, in the case of treatments for axillary hyperhidrosis, the clinician can have follow-up sessions where sweating is mapped (e.g., iodine staining) to (1) identify the remaining areas for treatment and (2) determine the overall reduction in sweating in the underarm area. For patients who do not necessarily desire 100% anhidrosis, a staged treatment may allow them to discontinue treatment at a particular point. For example, a patient suffering from a severe case of axillary hyperhidrosis may be satisfied with at least about 20%, 30%, 40%, 50%, 60%, 70%, 80%, 90% or more reduction in sweating and may only wish to participate in the number of treatments necessary for such reduction.

Additionally, a staged and patterned treatment can minimize the body's contracture response during the healing process. In a process called fibrosis (or scarring), fibroblasts lay down a mesh of collagen to facilitate the healing of tissue. As the density of the scar increases, the treated area contracts, thereby tightening the skin within that region. In the case of treatments for axillary hyperhidrosis, contracture could potentially impair the patient's full range of arm motion. A treatment can be patterned and staged to minimize contracture and/or its impact on the patient. For example, the slender treatment areas depicted in FIG. 18C would result in minimal axillary contracture and resulting impairment to range of arm motion.

Figure 19:
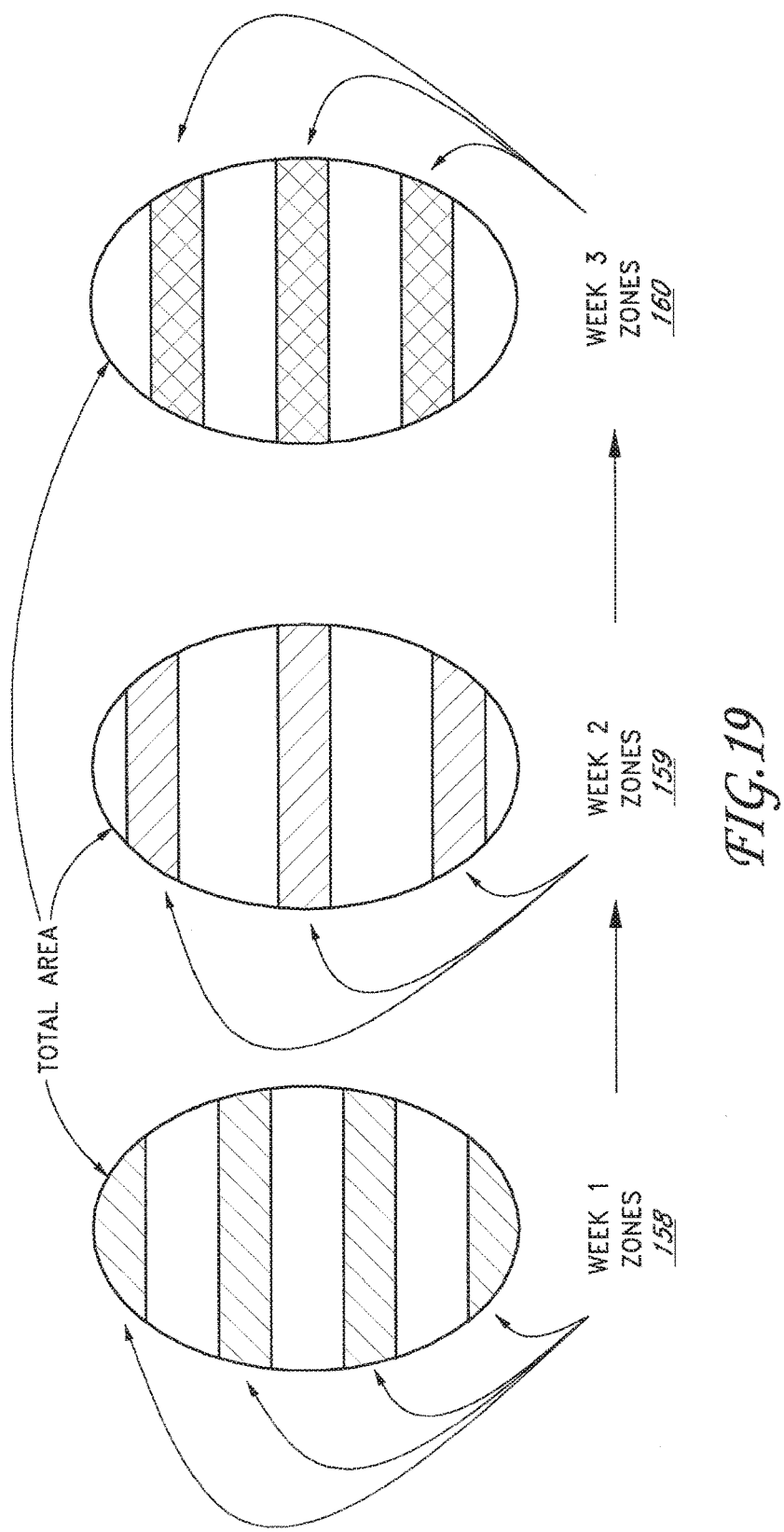
FIG. 19 shows three templates to be used in a staged treatment, wherein each template is configured to allow treatment to a different portion of the overall treatment area according to one embodiment.

A template can be used to facilitate the application of a staged and/or patterned treatment. FIG. 19 illustrates a staged treatment series comprising three templates 158, 159, 160 wherein each template is configured to allow treatment to a different portion of the overall treatment area. The templates 158, 159, 160 may be configured to engage an energy delivery device or one or more energy delivery elements (not shown) to facilitate the application of a staged and/or patterned treatment. The templates 158, 159, 160 can be comprised of a single frame made from an appropriate material such as, for example, wood, plastic or metal with removable or adjustable pieces to reflect the desired pattern and/or stage. Alternatively, the templates 158, 159, 160 may also be of one or more patterns that are drawn on the patient's skin using a temporary marker, tattoo or dye (e.g., henna) that will remain over the course of multiple staged treatments.

System Embodiments

In some embodiments, disclosed is a system and method for using microwave energy to thermally affect the sweat glands and surrounding tissue non-invasively. Such a system and method may be useful in treating, for example, excessive sweating, or hyperhidrosis. The system includes a microwave generator, a microwave applicator, a cooling component, and a tissue acquisition component.

The microwave applicator includes one or more microwave antennas that are placed against or adjacent the patient's skin and configured to deliver energy to a target layer at a designated depth of a patient's skin, specifically to the region of the dermis and hypodermis where sweat glands reside. Shielding is provided around the applicator in certain embodiments to localize the microwave energy to a targeted region of the patient's skin.

The cooling component includes a ceramic cooling plate (such as made of ceramic) configured to contact the skin of a patient and protectively cool a layer of skin above the target layer, e.g., the epidermis. The cooling component also includes a coolant flow circuit chamber adjacent to the cooling plate configured to receive a cooling fluid. The cooling component also includes a temperature regulating component to cool or heat the fluid and a pump to circulate the fluid.

The tissue acquisition component includes a suction chamber for elevating and receiving the skin to be treated, one or more suction ports in communication with a vacuum pump, and a thermocouple wire for measuring the temperature of the skin.

In some embodiments, a method of reducing sweat production involves identifying an area of skin to be treated; activating the vacuum pump to acquire the skin within a suction chamber; cooling a first layer of the skin via a cooling element; delivering microwave energy to a second layer of skin containing sweat glands while the first layer of the skin is protectively cooled, the second layer deeper than the first layer relative to the skin surface; and deactivating the vacuum pump to release the skin.

FIG. 20 illustrates schematically a microwave applicator system 161 for treating various skin features, according to one embodiment of the application. The system includes a waveguide antenna 145 operably connected to a coaxial cable (not shown), which is in turn connected to a microwave generator 113 (not shown).

The microwave generator 113 preferably includes a generator head, a power supply, and an isolator. The generator 113 may be configured to have a frequency of between about 915 MHz to 15 GHz, more preferably between about 2.4 GHz to 9.2 GHz, such as about 2.45 GHz and 5.8 GHz, and have an output power maximum, in some embodiments, of no more than about 300 W, 200 W, 100 W, 75 W, or less. Various medical microwave generators that may be adapted for use with the disclosed embodiments include, for example, those from Microsulis Medical Ltd., (9.2 GHz MEA Treatment System) (Denmaed, Hants, UK); Flex 2 or Flex 4 2.45 GHz MW ablation system from AFx, Inc., Fremont, Calif.; the Targis and Prostatron 915 MHz Systems from Urologix, Minneapolis, Minn.); and the BSD-500 hyperthermia system from BSD Medical, Salt Lake City, Utah.

The antenna 145 preferably has a frequency of between about 915 MHz to 15 GHz, more preferably between about 2.4 GHz to 9.2 GHz, such as about 2.45 GHz and 5.8 GHz.

The waveguide antenna 145 preferably has a cross-sectional size configured to the desired operational frequency and field configuration of the waveguide. Generally, lowest-order Transverse Electric (TE) modes are utilized (e.g., $TE_{10}$), although others are possible, such as Transverse Magnetic (TM), Transverse ElectroMagnetic (TEM), effervescent, or a hybrid mode. For example, the width and height (rectangular) or diameter (circular) waveguide geometry correlate with the operational frequency and field configuration of the waveguide 145.

The length of the waveguide 145 is preferably adjusted such that the physical length of the waveguide 145 corresponds to an electrical length that is a half-wavelength multiple of the guided wavelength at the desired operational frequency.

The waveguide 145 can have any cross-sectional geometry depending on the desired clinical objective and geometry of the particular anatomical area to be treated. In some embodiments, the waveguide 145 has a rectangular, circular, elliptical, or hexagonal cross-sectional geometry.

In some embodiments, the coaxial feed (not shown) can be placed between about 1 mm to 10 mm from the (inner) back wall of the waveguide 145, with an insertion depth of 1 mm to 7 mm. The placement is most preferably optimized for efficient transfer of power from coaxial feed to waveguide 145.

Figure 22:
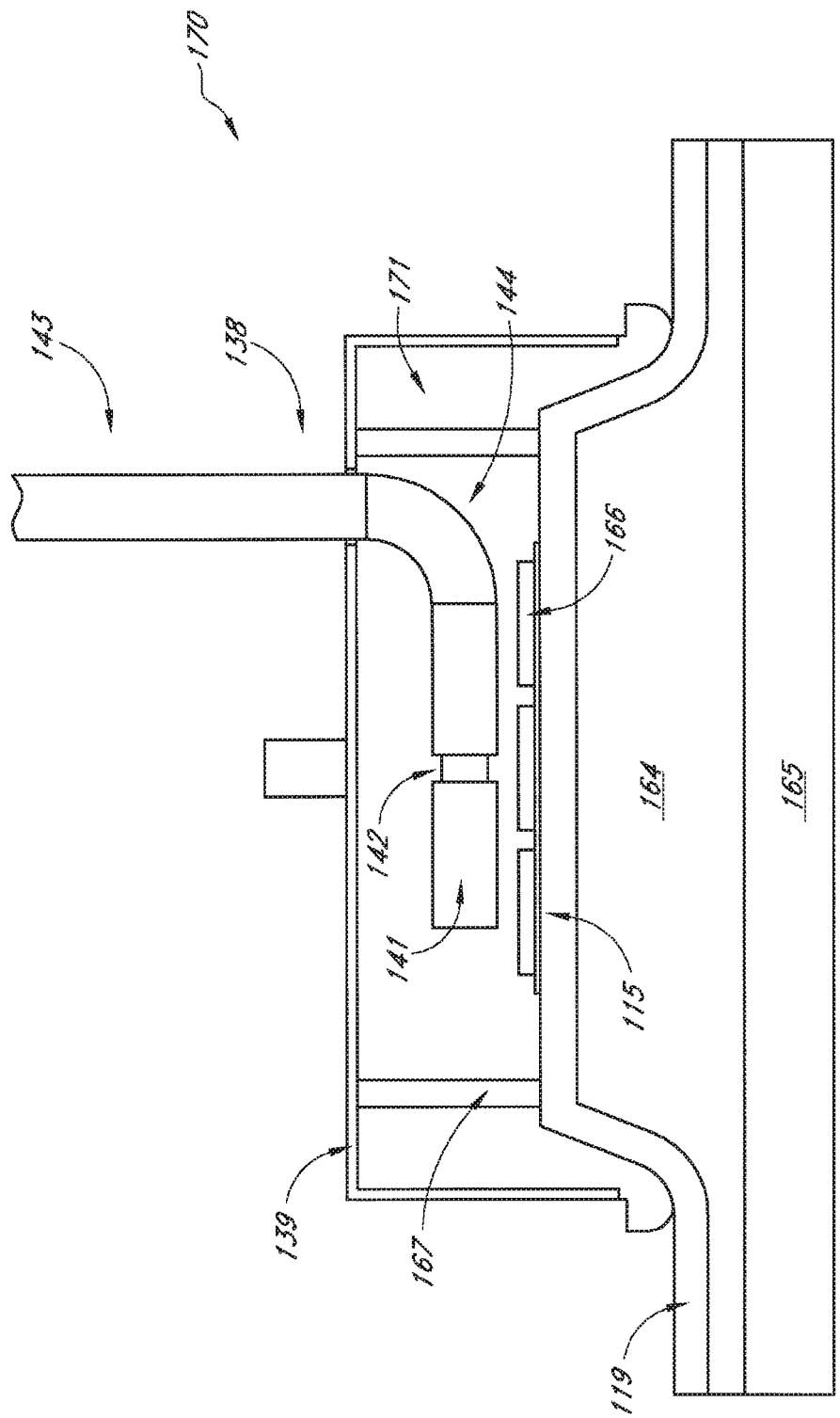
FIG. 22 shows a schematic of a microwave applicator system including a slot antenna according to one embodiment.
Figure 22A:
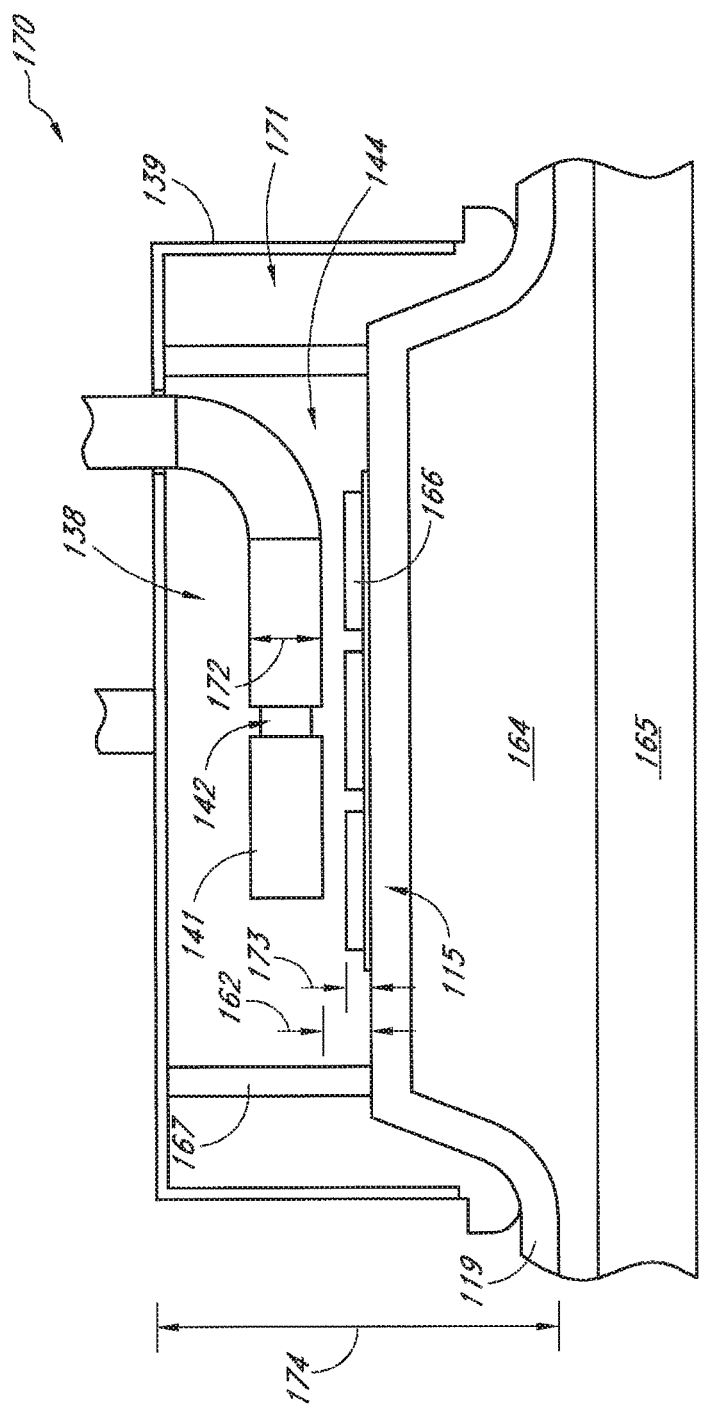
FIG. 22A shows a schematic of a microwave applicator system including a slot antenna and various adjustable dimensional parameters according to one embodiment.

To have the desired energy density in the region of target tissue, it is preferred that the antenna 145 be within 0.5-5 mm of the epidermis 102 (e.g., between about 1.5-2 mm, such as about 1.75 mm). This distance may be referred to herein as the antenna standoff height 162, as shown in FIG. 22A, which shows an alternative embodiment of a slot antenna configuration. Variation of the standoff height 162 affects the spread of the microwave radiation. With a very large standoff height 162, a reduced energy density over a larger volume is achieved. Conversely, with little to no standoff height 162 the energy density is generally much higher over a smaller volume. To achieve therapeutic energy density levels with a large standoff height 162, significantly increased input power levels are necessary. The absorption pattern of the microwave energy at depth in tissue, strongly influenced by the standoff 162, directly influences the relative safety margin between target and non-target (deep) tissues. Finally, standoff height 162 causes large variation in the loading conditions for the waveguide 145, with reflected power levels observed by the antenna changing with standoff changes.

Distal end of the waveguide 145 can be operably connected to the cooling system, which includes a cooling fluid circuit 163 at least partially superimposed on a cooling plate 166, which preferably directly contacts the skin 119 to be treated. Underlying fat 164 and muscle layers 165 are also schematically shown. In one embodiment with a rectangular waveguide, the cooling plate has a rectangular geometry and dimensions of 15 mm×25 mm. The thickness of the flow chamber is preferably less than about 3 mm, 2 mm, 1.5 mm, 1 mm, 0.75 mm, or 0.5 mm.

Also illustrated in FIG. 20 are one or more vacuum ports that are operably connected to a source of vacuum, as previously described. The applicator, cooling components, and vacuum ports are preferably all connected into a self-contained housing 168 as shown.

FIG. 21 illustrates schematically the underside of the waveguide applicator system 161 of FIG. 20. Shown is the waveguide 145, which is operably connected distally to the cooling fluid circuit running over cooling plate 166 (rectangular area as shown), and two vacuum ports 167 each lateral to the cooling plate 166. All elements are preferably contained within housing 168 to facilitate efficient energy delivery, cooling, and suction to the specific area to be treated.

Figure 21B:
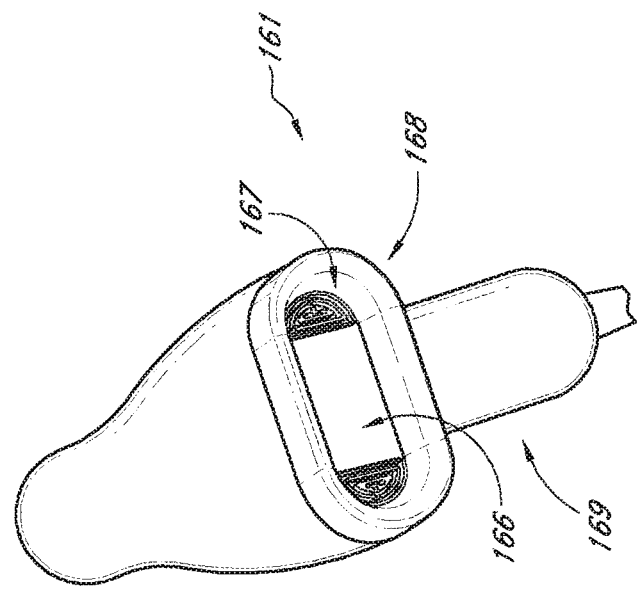
FIG. 21B shows an alternate perspective view of the microwave applicator of FIG. 21A including a handle and housing.
Figure 21A:
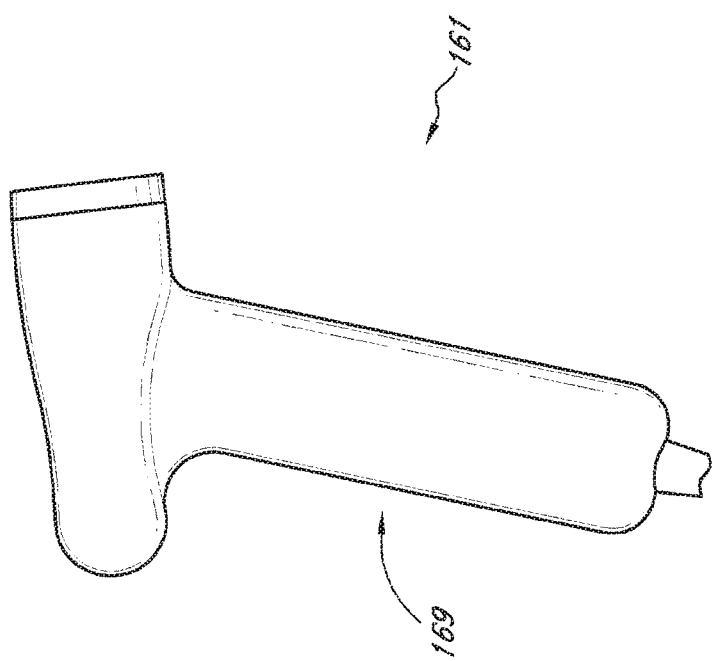
FIG. 21A shows a side perspective view of a microwave applicator including a handle according to one embodiment.

FIG. 21A illustrates a side perspective view of a microwave applicator 161 including handle 169 for a waveguide antenna system, according to one embodiment of the application. FIG. 21B illustrates another view of the waveguide applicator handle 169 of FIG. 21A, also illustrating the housing 168 (e.g., the suction chamber), vacuum port 167, and cooling plate 166.

Single Slot Embodiment

In some embodiments, a microwave applicator system 170 includes a slot antenna 138. The slot antenna 138 includes a proximal portion 143, a bent portion 144, a slot 142, and a distal tip portion 141 as shown in FIG. 22. The diameter of the slot coaxial cable (not shown) within the slot antenna 138, is preferably large enough to handle the desired microwave power, which may be no more than about 200 watts, 150 watts, 100 watts or less in some embodiments. The diameter of the slot antenna 138 can also be varied to introduce changes to the radiation characteristics of the antenna. In some embodiments, the slot 138 diameter is between about 0.047" to 0.500", such as between about 0.085" to 0.25" in some embodiments, or such as about 0.085" or 0.141" in certain embodiments.

The slot 142 width, in some embodiments, can be between about 0.5 mm to 5 mm, such as between about 1 mm to 2 mm, such as about 1.5 mm in some embodiments. In general, the slot 142 width has a strong influence on both the operational frequency as well as the "depth of resonance" (in other words, the amount of coupling into the tissue at the optimal frequency). While the slot 142 is preferably circumferential, non-circumferential slots 142 are also within the scope of the application.

The distal antenna tip portion 141, which is the portion 141 distal to the slot 142 as shown, can have a length in some embodiments of about 0.5 mm-15 mm, such as between about 1 mm-10 mm, such as about 8 mm. The length of the tip portion 141 can influence the operational frequency of the antenna. For example, a longer distal tip portion 141 will result in a lower frequency.

The slot 142 width and the length of the distal antenna tip 141 portion are primary variables that affect the relative power deposition (Specific Absorption Rate) characteristics at depth in tissue, as well as the efficiency of power transfer from the antenna into tissue at the desired frequency.

The slot antenna 138, in some embodiments, includes a bent portion 144 between the proximal slot antenna 143 and the slot 142. The bent portion 144 can have any appropriate angle of curvature, such as at least about 15, 30, 45, 60, 75, 90, 105, 120, 135 degrees, or more. As shown, the bent portion 144 has an angle of curvature of approximately 90 degrees. A bent portion 144 of a slot antenna 138 can have several advantages. Slot antennas 138 which are fed by an unbalanced coaxial line, have back currents that cause back-radiated fields to travel proximally up the outer conductor of the cable back towards the power source. The bend 144 is introduced into the cable at a point before the first standing wave caused by the back fields. This ensures there are no unwanted tissue ablation areas that can occur at locations along the cable where the outer shielding of the cable is in close proximity to the tissue. The bend 144 location also affects power transfer characteristics from the antenna into tissue and ensures greater consistency across treatments.

With respect to the antenna stand-off height 162 as previously described, to obtain a desired energy density in the region of target tissue, it is preferred that the antenna be within 0.5-5 mm of the skin (e.g., between about 1.5-2 mm, such as about 1.75 mm).

FIG. 22A illustrates various dimensional parameters of a single slot antenna 138 according to one embodiment that can be adjusted depending on the energy delivered and the skin surface area to be treated. Shown is the antenna stand-off height 162, antenna diameter 172, cooling chamber thickness 173, and shielding/body height 174. While the variables are illustrated with a single slot antenna configuration, it will be appreciated that the parameters can be adjusted for other antenna embodiments as well.

As shown in the schematic drawing of FIG. 22A, a slot antenna system 170 (as opposed to a waveguide antenna system), in some embodiments, includes a microwave shielding element 139 due to the omnidirectional nature of energy delivery of the slot antenna 138. Shielding elements 139 can be advantageous for one or more of the following reasons: (1) shielding may increase efficiency and therefore increase overall power; (2) by preventing parts of the field from straying, the shielding may allow for greater consistency and reliability across multiple treatments; (3) shielding may choke off proximally traveling currents down the outer conductor, thereby eliminating the back-radiated fields; (4) shielding may remove the inherently omni-directional radiation characteristic of the antenna, redirecting the energy back towards the target tissue; and (5) the geometry of the shielding may be used as an additional tool to achieve an optimal power deposition characteristic in tissue, as well as allow for efficient power transfer.

The shielding 139 may be solid or mesh in some embodiments, and may have absorptive and/or reflective shielding properties. For example, graphite can be used if absorptive shielding is desired. Metal shieldings are generally reflective without being absorptive. If reflective mesh shielding is used, the pore size used is generally related to the wavelength (i.e., larger wavelength allows for larger openings). Mesh shielding advantageously allows for visualization of tissue acquisition and, accordingly, confirmation of tissue engagement by the operator.

The shielding 139 is preferably located at an optimal distance away from the slot antenna 138. When the shielding 139 is too close to the slot antenna 138, the antenna field may couple to part of the shielding 139 (usually an edge) and the coupled portion will begin to radiate at unwanted locations, creating what is known as a "hot spot" effect. Therefore, in some embodiments, the lateral shielding 139 is kept at a distance, such as at least about 5 mm, 7 mm, 10 mm, or more, away from the antenna 138 so as to sufficiently limit or ideally, eliminate the hot spot effect. Additionally, if some coupling exists at the shield edge, the shielding may be lifted such that it is not in direct contact with the skin, thus reducing or removing any tissue absorption in this location. The proximal back wall of shielding is preferably kept at an appropriate distance from the coaxial cable so as to prevent back radiation of the field and further focus the field toward a target wavelength. The shielding may extend adjacent to and parallel with the skin surface to protect the skin. As it may be advantageous to have shielding spaced laterally at least a certain distance from the antenna, shielding portions of the skin surface may be desirable in order to create a treatment window of defined width. The geometry of the shielding element can be determined depending on the geometry of the treatment area and the desired clinical result. Some examples of shielding element geometries are, for example, cylindrical, hemispherical, and rectangular.

The cooling components, such as cooling fluid (not shown) and plate 115, as well as tissue acquisition components and their respective parameters may be as previously described. The control system may also be as previously described, however, operation parameters can be varied without undue experimentation in order to achieve a result similar to that of the waveguide embodiments.

Figure 23:
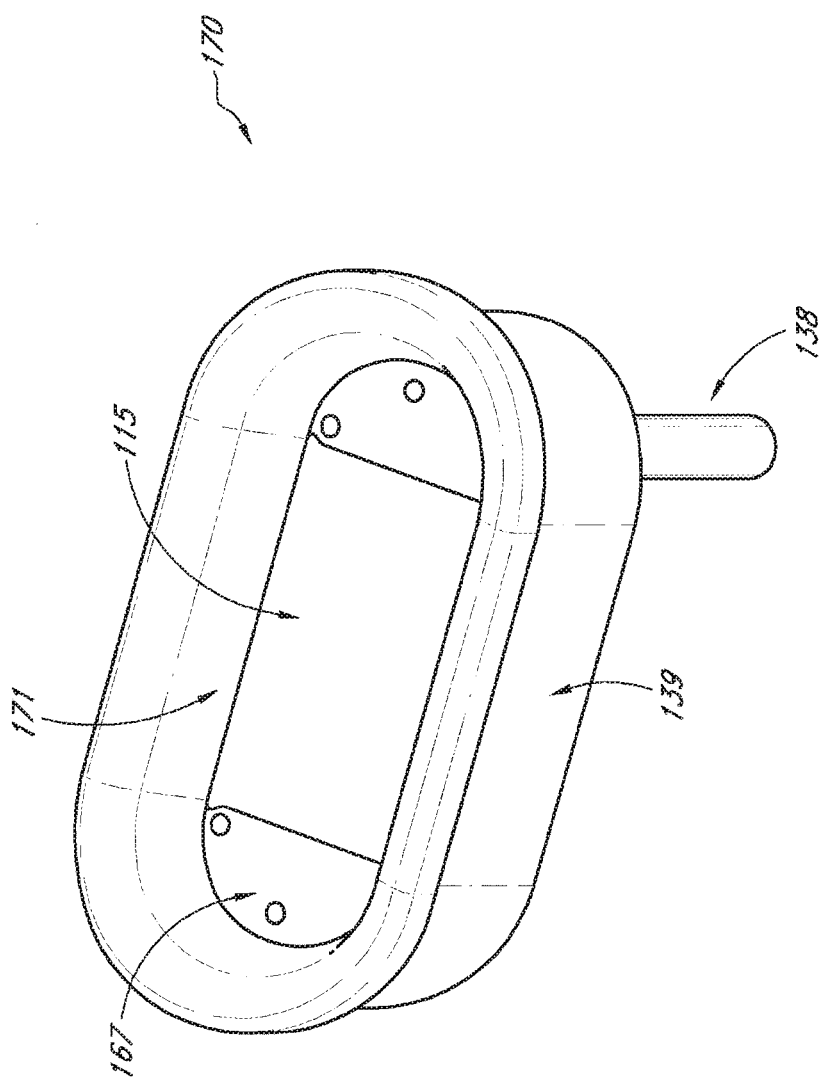
FIG. 23 shows a schematic of an underside of a waveguide applicator system including slot antenna and tissue capture according to one embodiment.

FIG. 23 illustrates schematically the underside of the slot applicator system 170 of FIG. 22. Shown is the slot antenna 138, which is operably connected distally to the cooling fluid circuit running over cooling plate 115, and two vacuum ports 167 each lateral to the cooling plate 115. Shielding 139 preferably surrounds at least a part of the housing 171 to prevent unwanted energy delivery outside the desired treatment area.

Twin Slot

Figure 24:
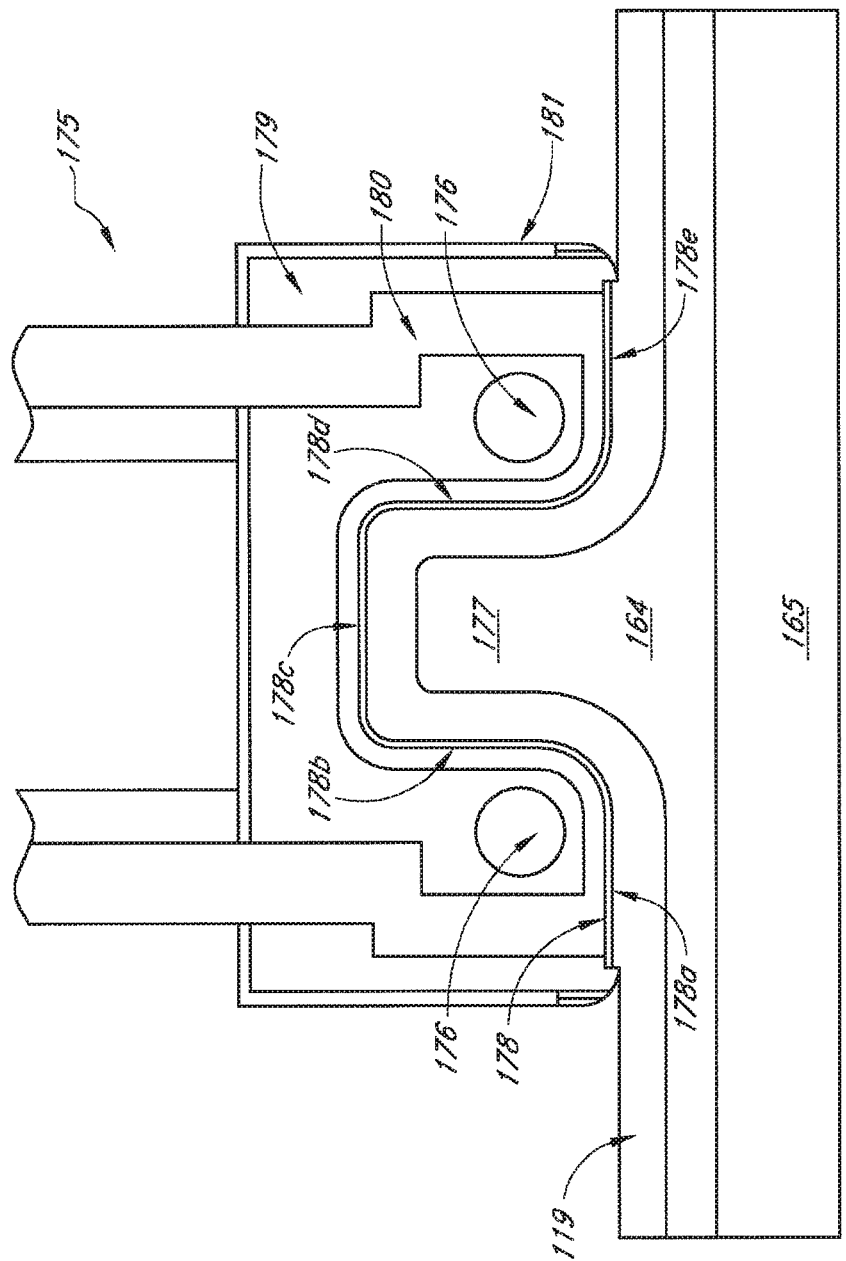
FIG. 24 shows a schematic of a microwave applicator system including a plurality of slot antennas and tissue capture according to one embodiment.

In some embodiments, the microwave applicator system 175 includes a plurality of slot antennas 176, as illustrated schematically in FIG. 24 above. In such configurations, two or more coaxial slot antennas 176 operate as a phased array. The spacing of antennas 176, the alignment of tissue pinch 177 with the antennas 176, and the phase relationship between the inputs to the two antennas 176 may be additional variables that can be altered by one skilled in the art depending on the desired clinical result.

The interaction between the e-fields created by each antenna 176 may vary depending on the spacing of the antennas 176 with respect to each other. Care must be taken not to space the antennas 176 too closely together, which can lead to large power coupling from one antenna into the other that travels back into the microwave generator (not shown). Antennas 176 can be spaced from 0 mm to 10 mm away from the cooling fluid in a "side of the pinch" configuration, and can be spaced at a distance of approximately 8 mm to 30 mm apart from each other in an "above the pinch" configuration.

The relative alignment of tissue pinch acquisition with antennas 176 can also be altered depending on the desired clinical result. Two configurations have been shown to lead to advantageous power deposition patterns in tissue—either alignment of the twin antennas 176 on either side of the "pinch" 177 as shown or in other embodiments, alignment of the twin antennas 176 above the "pinch" 177. In both cases the antenna pinch 177 alignment can be adjusted such that areas of high e-field can be focused in the treatment site while reducing fields in the non-target tissue.

The antennas 176 can be configured for phased operation. Driving the antennas 176 in-phase results in a focused e-field pattern, with constructive interference between the two antennas 176 occurring in the target region and destructive interference occurring in the non-target region. Such focusing, in combination with the geometry of the tissue pinch 177 configuration, leads to a higher potential for lower-frequency drive signals to be utilized than in a single-antenna system as previously described.

In some embodiments, in addition to in-phase operation, the relative spatial position of the peak e-field region between the two antennas 176 can be varied by introducing a phase difference between the input signals to the antennas 176 depending on the desired clinical result. This allows the treatment region to be directed to different locations with great accuracy by a process known as "beam steering." For example, the treatment region can be re-directed from a region laying exactly in-between the two antennas 176 (with in-phase operation), to a bifurcated treatment region that has dual treatment areas in the tissue regions that lay in closest proximity to each antenna (with anti-phase operation). FIG. 24A illustrates a simulation of the two antennas with an in-phase drive operation.

FIG. 24B illustrates a simulation of the two antennas in anti-phase drive (103 degree phase shift between drive signals of the first antenna and the second antenna).

Figure 24C:
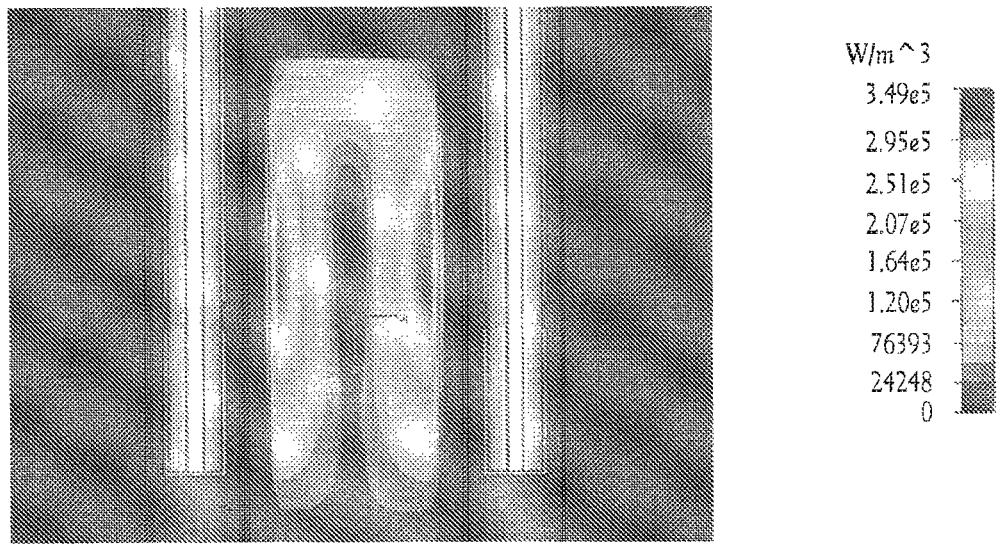
FIG. 24C shows a computer generated image created by simulating of two antennas having an in-phase drive operation with a 170 degree phase shift between drive signals of a first antenna and a second antenna.

FIG. 24C illustrates a simulation of the two antennas with a 170 degree phase shift between drive signals of the first antenna and the second antenna.

Figure 24D:
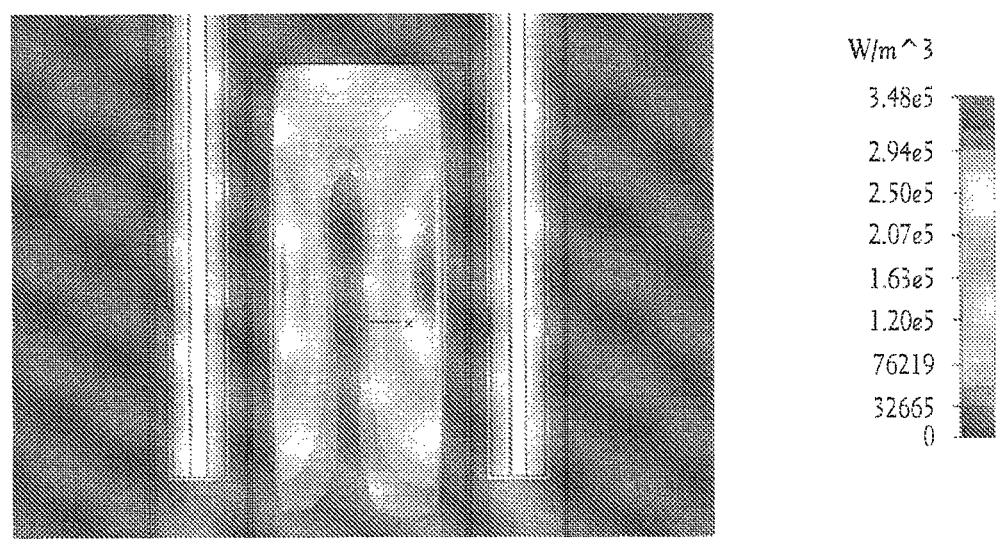
FIG. 24D shows a computer generated image created by simulating two antennas having an in-phase drive operation with a 155 degree phase shift between drive signals of a first antenna and a second antenna.

FIG. 24D illustrates a simulation of the two antennas with a 155 degree phase shift between drive signals of the first antenna and the second antenna.

In the dual slot embodiments, shielding 1208 is preferably present to minimize energy distribution outside of the treatment area and can be as previously described.

The cooling components and parameters of a multi-slot antenna system 175 can be similar to those described with respect to the waveguide embodiments, however there are some geometric changes. In one exemplifying embodiment, with the dual-slot antenna configuration 175 shown, the cooling chamber has five distinct cooling faces (178*a*, 178*b*, 178*c*, 178*d*, 178*e*), or surfaces: one surface 178*c* at the top of the tissue pinch 177 (measuring about 9 mm×27 mm of cooling plate surface); two surfaces 178*b*, 178*d* at the sides of the pinch extending generally vertically (measuring about 10 mm×27 mm of cooling plate surface each); and two lateral surfaces 178*a*, 178*e* at the bottom of the pinch 177 extending generally horizontally (measuring about 10 mm×27 mm of cooling plate surface each). In some embodiments, the cooling chamber optionally includes a thin polyamide sheet which is used to connect the ceramic cooling plates 178*a-e*.

The tissue acquisition components (not shown), e.g., suction components, may be similar to those previously described, with the following additional considerations. By pinching the skin, the dermis and the hypodermis layers may, in essence, be isolated from the muscle layer. This enables the device to deliver a very controlled amount of energy to the dermis while protecting the muscle layer. The vacuum pump may have a suction pressure, in some embodiments, of about 400-700 mmHg, such as about 650 mmHg. The suction chamber may have any desired geometry. For example, in one embodiment, the suction chamber may have a central rectangular portion of about 10 mm in height×40 mm in length and a thickness of 9 mm. The material of the suction chamber housing is preferably transparent or translucent to enable visual confirmation of skin engagement.

The control system may also be as previously described, however, operation parameters can be varied without undue experimentation in order to achieve a result similar to that of the waveguide embodiments.

Figure 25:
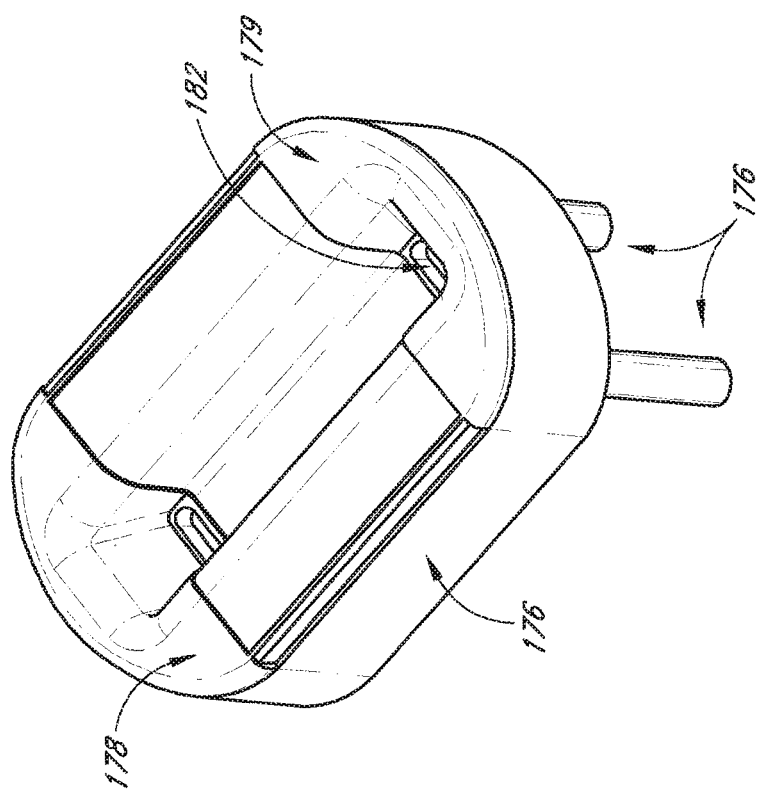
FIG. 25 shows a schematic of an underside of a waveguide applicator system including a dual slot antenna and tissue capture according to one embodiment.

FIG. 25 above illustrates schematically the underside of the dual slot applicator system 175 of FIG. 24. Shown are dual slot antennas 176, which are operably connected distally to the cooling fluid circuit running over cooling plate 178, and two vacuum ports 182 each lateral to the cooling plate 178. Shielding 181 preferably is present around at least a part of the housing 179 to prevent unwanted energy delivery outside the desired treatment area.

Figure 26:
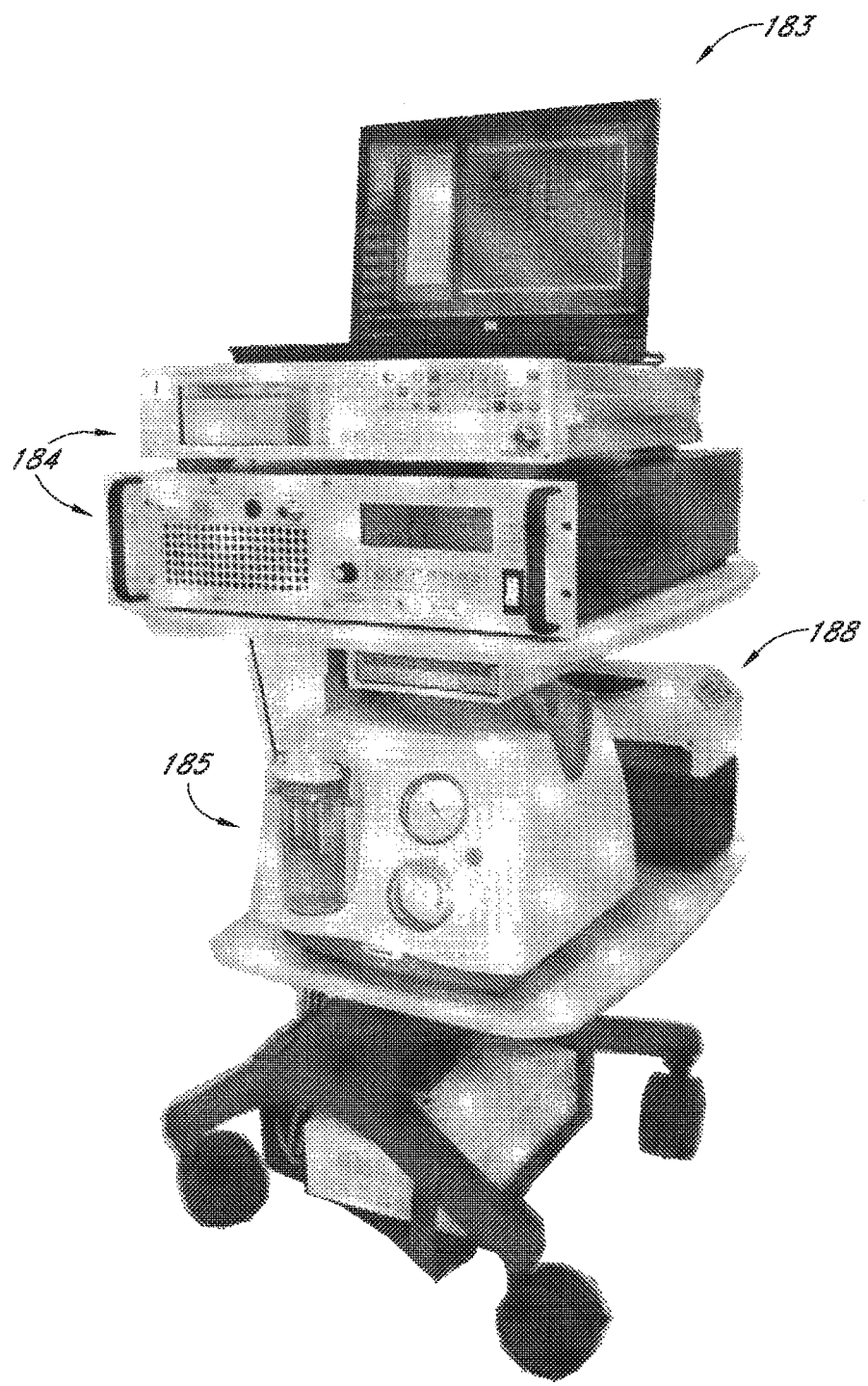
FIG. 26 shows a schematic of a microwave treatment system according to one embodiment.

FIG. 26 below illustrates one example of a microwave treatment system, including a computer 183 for data collection, a microwave signal generator and amplifier 184, a vacuum pump 185 for tissue acquisition, a temperature control unit (which may be a chiller in some embodiments) and circulating pump 188.

Figure 27A:
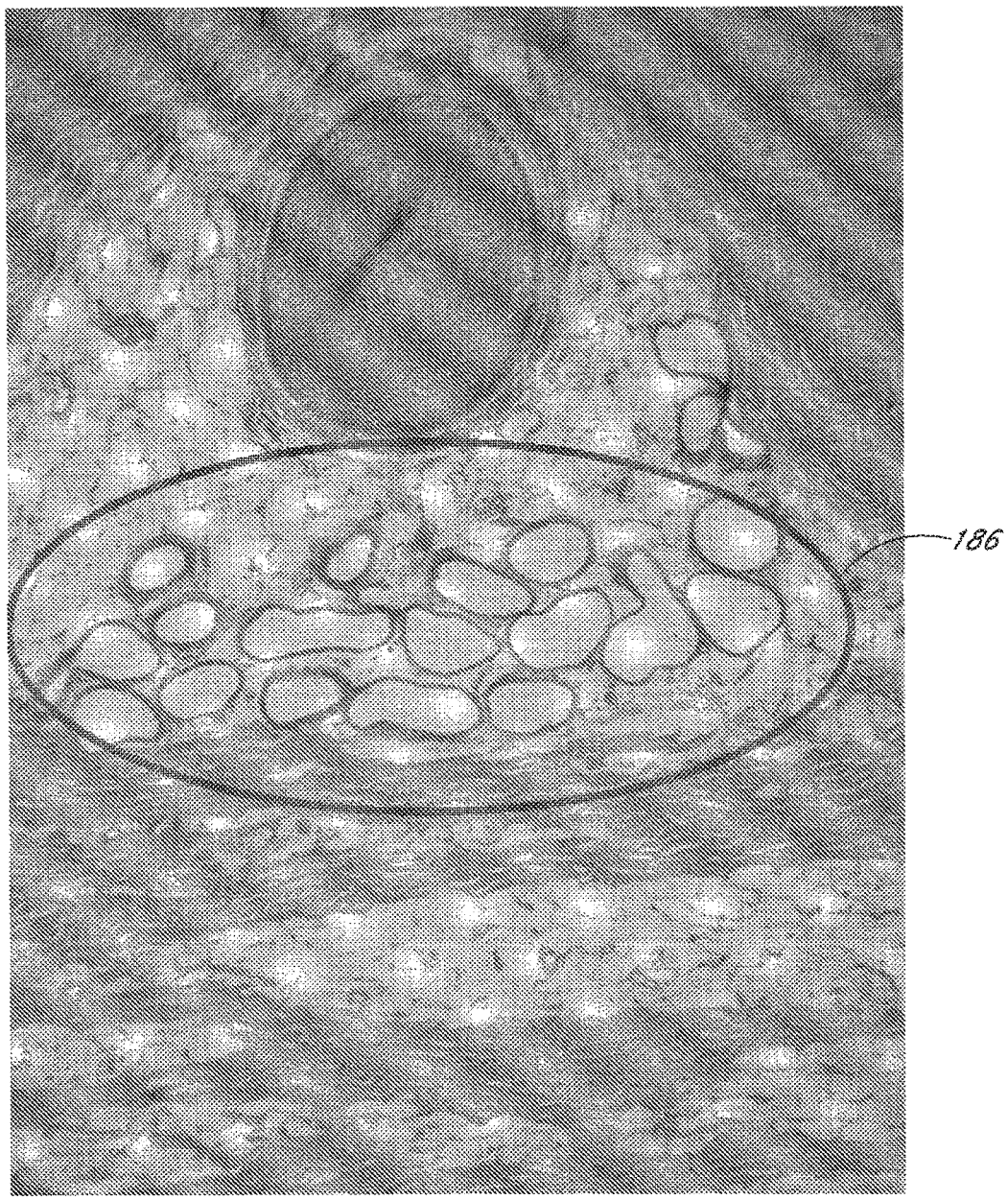
FIG. 27A shows a histological cross-section of a normal porcine apocrine gland at the dermal/hypodermal interface.

FIG. 27A below is a histologic cross-section of a normal porcine apocrine gland 186 (circled) that is in the dermal/hypodermal interface.

Figure 27B:
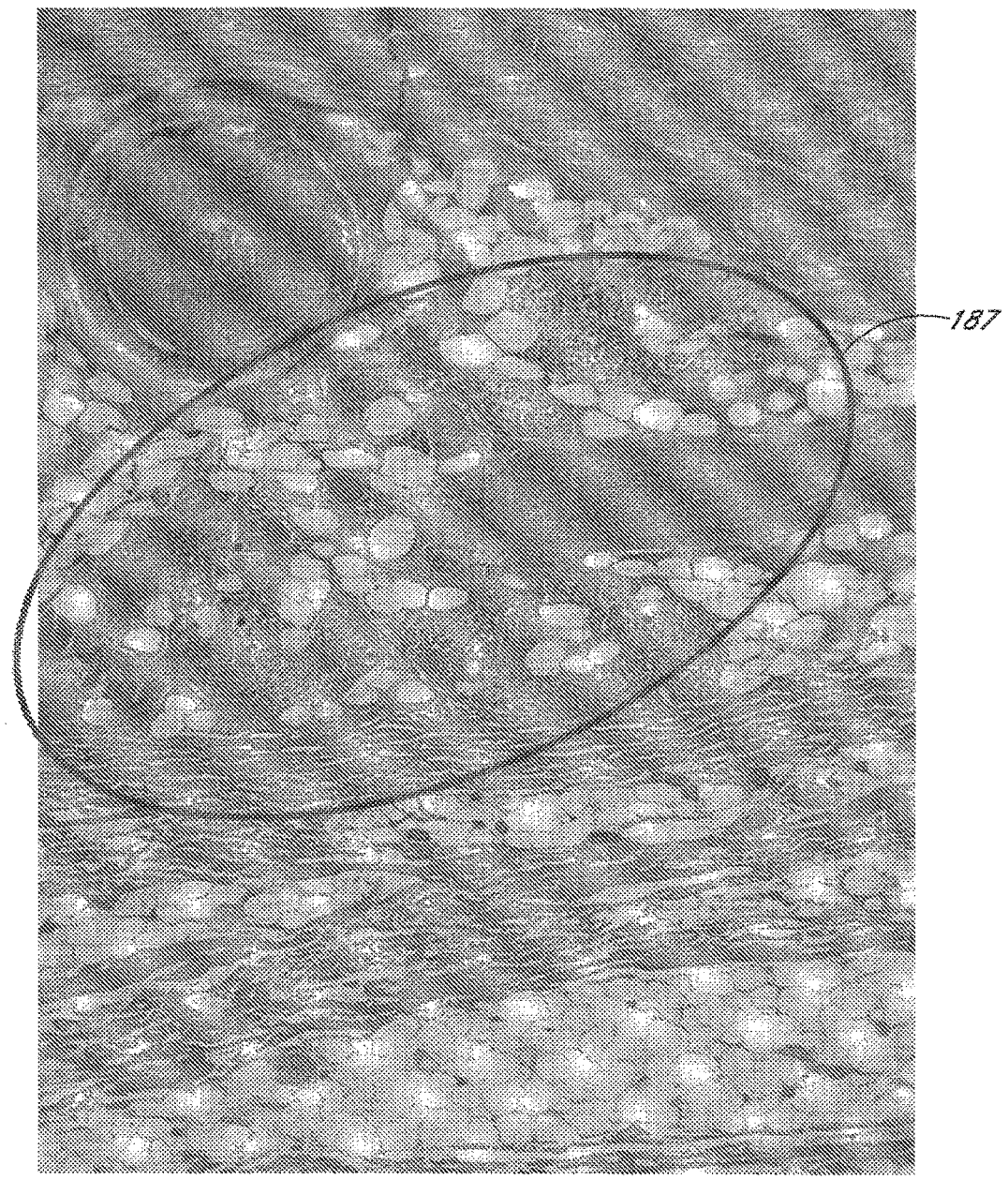
FIG. 27B shows a histological cross-section of a porcine sweat gland one week after microwave therapy.

FIG. 27B below is a histologic cross-section of a porcine sweat gland 187 (circled) one week status-post microwave therapy, illustrating gland disorganization and leukocytic infiltration related to the post-treatment inflammatory response. This histology demonstrates the selective nature of the microwave application. This type of result can be achieved with several different carefully selected combinations of antenna design and energy/cooling algorithms. One such combination is a 5.8 GHz waveguide antenna used at 55-60 W, with 3 seconds of energy application and a cooling of 22° C. for both during and 20 sec after energy application. This combination has been shown to provide positive results for both animals and humans.

Overview of Certain Methods, Systems and Other Embodiments

In one embodiment, the present application provides a method for treating a skin tissue of a patient comprising positioning a microwave energy delivery applicator over the skin tissue, securing the skin tissue proximate to the microwave energy delivery applicator, cooling the surface of the skin tissue; and delivering energy via the microwave energy delivery applicator to the skin tissue sufficient to create a thermal effect in a target tissue within the skin tissue.

In some embodiments, positioning a microwave energy delivery applicator over the skin tissue may further comprise positioning over the skin tissue a microwave antenna selected from the group consisting of single slot, multiple slot, waveguide, horn, printed slot, helical, patch, Vivaldi and combinations thereof.

In some embodiments, securing the skin tissue proximate to the microwave energy delivery applicator may further comprise applying suction to the skin tissue. In one embodiment, applying suction to the skin tissue may further comprise at least partially acquiring the skin tissue within a suction chamber adjacent to the energy delivery applicator.

In some embodiments, securing the skin tissue may further comprise elevating the skin tissue.

In some embodiments, cooling the surface of the skin tissue may further comprise positioning a cooling element in contact with the skin surface.

In some embodiments, cooling the surface of the skin tissue may further comprise conductively cooling the skin surface.

In some embodiments, cooling the surface of the skin tissue may further comprise convectively cooling the skin surface.

In some embodiments, cooling the surface of the skin tissue may further comprise conductively and convectively cooling the skin surface.

In some embodiments, the target tissue within the skin tissue may be selected from the group consisting of collagen, hair follicles, cellulite, eccrine glands, apocrine glands, sebaceous glands, spider veins and combinations thereof.

In some embodiments, the target tissue within the skin tissue may comprise the interface between the dermal layer and subcutaneous layer of the skin tissue.

In some embodiments, the thermal effect in the target tissue may comprise thermal alteration of at least one sweat gland.

In some embodiments, the thermal effect in the target tissue comprises ablation of at least one sweat gland.

In one embodiment, the method may further comprise monitoring a diagnostic parameter of the skin tissue. The diagnostic parameter may be selected from the group consisting of impedance, temperature, and reflected power.

In one embodiment, the method may further comprise administering to the patient a medication selected from the group consisting of anesthetics, steroids, and antibiotics. Administering medication to the patient may further comprise administering the medication orally, topically or via injection.

In one embodiment, the present application provides a system related to treating a skin tissue of a patient comprising a microwave energy generator; a microwave antenna configured for placement proximate to the skin tissue of the patient; a cooling element configured for placement in contact with the skin tissue of the patient; and a suction element configured for elevating the skin tissue and placing the skin tissue in contact with the cooling element; wherein the microwave antenna is operatively coupled to the microwave energy generator, and wherein the microwave antenna is configured to deliver energy to the skin tissue sufficient to create a thermal effect in a target tissue within the skin tissue.

In some embodiments, the microwave antenna may be selected from the group consisting of single slot, multiple slot, waveguide, horn, printed slot, patch, Vivaldi and combinations thereof.

In some embodiments, the microwave antenna may be a waveguide antenna. In one embodiment, the waveguide antenna may comprise an array of waveguide antennas.

In some embodiments, the microwave antenna may be a single slot antenna.

In some embodiments, the microwave antenna may be a dual slot antenna.

In some embodiments, the microwave energy generator may be configured to deliver microwave energy at a frequency of about 2.45 GHz.

In some embodiments, the microwave energy generator may be configured to deliver microwave energy at a frequency of about 5.8 GHz.

In some embodiments, the cooling element may be selected from the group consisting of a solid coolant, liquid spray, gaseous spray, cooling plate, thermo-electric cooler and combinations thereof.

In some embodiments, the cooling element may comprise a thermally-conductive plate. The thermally-conductive plate may be substantially transparent to microwave energy. In one embodiment, the cooling element may further comprise a flow chamber adjacent to the thermally-conductive plate, wherein the flow chamber is configured to retain a liquid coolant. In one embodiment, the liquid coolant may be configured to flow through the flow chamber, thereby cooling the thermally-conductive plate. The liquid coolant may be selected from the group consisting of water, deionized water, alcohol, oil and combinations thereof. In one embodiment, the liquid coolant may comprise deionized water. In one embodiment, the liquid coolant may comprise deionized water and alcohol.

In some embodiments, the thermally-conductive plate may comprise a ceramic.

In some embodiments, the suction element may comprise a suction chamber configured to acquire at lease a portion of the skin tissue. The suction element may be operatively coupled to a vacuum source. In one embodiment, the suction chamber may be further configured with at least one tapered wall.

In one embodiment, the system further comprises a temperature sensor. The temperature sensor may comprise a thermocouple configured for monitoring the temperature of the skin tissue.

In one embodiment, the present application provides a microwave energy delivery apparatus related to non-invasively treating a skin tissue of a patient comprising a thermally-conductive plate adjacent to the microwave antenna; and a suction chamber; wherein the thermally-conductive plate is configured to contact the skin tissue, cool the skin tissue and physically separate the skin tissue from the microwave antenna, and wherein the suction chamber is configured to at least partially acquire the skin tissue and bring the skin tissue in contact with the cooling plate.

In one embodiment, the microwave energy delivery apparatus may further comprise a shield configured for containing excess energy fields. In one embodiment, the shield may be comprised of a reflective material. In one embodiment, the shield may be comprised of an energy absorbent material.

In one embodiment, the present application provides a method related to creating a subdermal lesion in a skin tissue of a patient comprising delivering microwave energy to the skin tissue and applying a cooling element to the skin tissue, wherein the microwave energy is delivered at a power, frequency and duration and the cooling element is applied at a temperature and a duration sufficient to create a lesion at the interface between the dermis layer and subcutaneous layer in the skin tissue while minimizing thermal alteration to non-target tissue in the epidermis and dermis layers of the skin tissue.

In one embodiment, the present application provides a method related to reducing sweat production in a patient comprising identifying an area of skin to be treated, activating a vacuum pump to acquire the skin within a suction chamber, cooling a first layer of the skin via a cooling element, delivering microwave energy to a second layer of skin containing sweat glands sufficient to thermally alter the sweat glands while the first layer of skin is protectively cooled, the second layer deeper than the first layer relative to the skin surface and deactivating the vacuum pump to release the skin.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. When the claims use the word "or" in reference to a list of two or more items, that word covers all of the following interpretations of the word: any of the items in the list, all of the items in the list, and any combination of the items in the list.

The above detailed descriptions of embodiments of the invention are not intended to be exhaustive or to limit the invention to the precise form disclosed above. Although specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can also be combined to provide further embodiments.

Related methods, apparatuses and systems utilizing microwave and other types of therapy, including other forms of electromagnetic radiation, and further details on treatments that may be made with such therapies, are described in the above-referenced provisional applications to which this application claims priority, the entireties of each of which are hereby incorporated by reference: U.S. Provisional Patent Application No. 60/912,889, entitled "Methods and Apparatus for Reducing Sweat Production," filed Apr. 19, 2007, U.S. Provisional Patent Application No. 61/013,274, entitled "Methods, Delivery and Systems for Non-Invasive Delivery of Microwave Therapy," filed Dec. 12, 2007, and U.S. Provisional Patent Application No. 61/045,937, entitled "Systems and Methods for Creating an Effect Using Microwave Energy in Specified Tissue," filed Apr. 17, 2008. While the above-listed applications may have been incorporated by reference for particular subject matter as described earlier in this application, Applicants intend the entire disclosures of the above-identified applications to be incorporated by reference into the present application, in that any and all of the disclosures in these incorporated by reference applications may be combined and incorporated with the embodiments described in the present application. Specific non-limiting examples of embodiments that may be utilized with systems, apparatuses and methods described herein include embodiments seen for example, in FIGS. 2-25 and pp. 9-18 and 56-69 of Application No. 61/045,937, previously incorporated by reference in its entirety.

In general, the terms used in the following claims should not be construed to limit the invention to the specific embodiments disclosed in the specification, unless the above detailed description explicitly defines such terms. While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

What is claimed is:

1. A system for treating a skin tissue of a patient comprising:
    a microwave energy generator, the microwave energy generator being configured to deliver microwave energy at a frequency of about 5.8 GHz;
    an array of waveguide antennas configured for placement proximate to the skin tissue, the array of waveguide antennas being configured for simultaneous or sequential treatment of multiple sections of skin tissue and being configured to radiate electromagnetic radiation in the lowest-order Transverse Electric modes;
    a cooling plate configured for placement in contact with the skin tissue;
    a cooling fluid circuit at least partially superimposed on the cooling plate and configured to retain a liquid coolant between the cooling plate and the array of microwave antennas;
    a suction element configured for elevating the skin tissue and placing the skin tissue in contact with the cooling plate;
    wherein the array of microwave antennas are operatively coupled to the microwave energy generator, and wherein the array of microwave antennas are configured to deliver energy to the skin tissue sufficient to create a thermal effect in a target tissue within a skin tissue.

2. The system of claim 1, wherein the cooling plate comprises a thermally-conductive cooling plate.

3. The system of claim 2, wherein the thermally-conductive cooling plate is substantially transparent to microwave energy.

4. The system of claim 1, wherein the cooling plate is configured to cool the skin tissue and physically separate the skin tissue from the array of microwave antennas.

5. The system of claim 1, wherein the thermally-conductive cooling plate comprises a ceramic plate.

6. The system of claim 1, wherein the liquid coolant is selected from the group consisting of water, deionized water, alcohol, and oil.

7. The system of claim 1, wherein the suction element comprises a suction chamber configured for elevating target tissue comprising a portion of the skin tissue from underlying tissue.

8. The system of claim 1, further comprising a temperature sensor comprising a thermocouple configured for monitoring the temperature of the skin tissue.

* * * * *